(12) United States Patent
Tsuchiya et al.

(10) Patent No.: US 7,479,543 B2
(45) Date of Patent: Jan. 20, 2009

(54) RESHAPED HUMAN ANTIBODY TO HUMAN INTERLEUKIN-6 RECEPTOR

(75) Inventors: Masayuki Tsuchiya, Gotenba (JP); Koh Sato, Gotenba (JP); Mary Margaret Bendig, West Hampstead (GB); Steven Tarran Jones, Radlett (GB); Jose William Saldanha, Enfield (GB)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 443 days.

(21) Appl. No.: 10/837,904

(22) Filed: May 4, 2004

(65) Prior Publication Data

US 2005/0142635 A1 Jun. 30, 2005

Related U.S. Application Data

(60) Continuation of application No. 09/114,285, filed on Jul. 13, 1998, now abandoned, which is a division of application No. 08/436,717, filed on May 8, 1995, now Pat. No. 5,817,790, which is a division of application No. 08/137,117, filed as application No. PCT/JP92/00544 on Apr. 24, 1992, now Pat. No. 5,795,965.

(30) Foreign Application Priority Data

Apr. 25, 1991 (JP) ..................................... 3-95476
Feb. 19, 1992 (JP) ..................................... 4-32084

(51) Int. Cl.
 *C07K 16/00* (2006.01)
(52) U.S. Cl. .................................................. 530/387.1
(58) Field of Classification Search ........................ None
See application file for complete search history.

(56) References Cited

FOREIGN PATENT DOCUMENTS

| EP | 2 409 607 | 1/1991 |
|----|-----------|--------|
| EP | 2 413 908 | 2/1991 |
| JP | 61-47500 | 3/1986 |
| JP | 62-500352 | 2/1987 |
| JP | 62-296890 | 12/1987 |
| WO | WO 9 007 860 | 7/1990 |
| WO | WO 9 109 967 | 7/1991 |
| WO | WO 91/09967 | * 7/1991 |

OTHER PUBLICATIONS

Rudikoff et al (Proc Natl Acad Sci USA 1982 vol. 79 p. 1979).*
Panka et al (Proc Natl Acad Sci USA vol. 85 3080-3084 May 1988).*
"Reshaping Human Antibodies for Therapy", Nature, vol. 332, London, GB, pp. 323-327,Mar. 24, 1988.
Oi et al., Biotechniques, vol. No. 3, p. 214 (1986).
Kitani et al., clin exp. Immunol., 88:75-83 (1992).
Sukui et al., Immunology, Letters 30:17-22.
Morrison, Hospital Practice p. 15 (Oct. 15, 1989).
Boulianne, Nature, vol. 321, p. 522-525 (1986).
Jones et al., Proc. Natl's. Acad. Sci., vol. 72, p. 3961-3965 (1075).

* cited by examiner

Primary Examiner—Christopher H Yaen
(74) Attorney, Agent, or Firm—Foley & Lardner LLP

(57) ABSTRACT

A reshaped human antibody to the human IL-6R, comprising:
 (A) an L chain comprising,
  (1) a human L chain C region, and
  (2) an L chain V region comprising human L chain framework regions (FRs), and mouse L chain complementary determination regions (CDRs) of a momoclonal antibody to the IL-6 receptor (IL-6R); and
 (B) an H chain comprising,
  (1) a human H chain C region, and
  (2) an H chain V region comprising human H chain FRS, and mouse H chain CDRs of a monoclonal antibody to the IL-6R.

Since major portion of the reshaped human antibody is derived from a human antibody and the mouse CDRs which are less immunogenic, the present reshaped human antibody is less immunogenic to human, and therefor is promised for therapeutic uses.

1 Claim, 24 Drawing Sheets

RESHAPED HUMAN ANTIBODY TO HUMAN INTERLEUKIN-6 RECEPTOR

This application is a continuation of U.S. application Ser. No. 09/114,285, filed Jul. 13, 1998, which is a divisional of U.S. application Ser. No. 08/436,717, filed May 8, 1995, now U.S. Pat. No. 5,817,790, which is a divisional of U.S. application Ser. No. 08/137,117, filed Dec. 20, 1993, now U.S. Pat. No. 5,795,965, which is a National Stage of PCT/JP92/00544, filed Apr. 24, 2992, which claims priority to Japanese patent application numbers JP 3-95476, filed Apr. 25, 1991 and JP 4-32084, filed Feb. 19, 1992.

TECHNICAL FIELD

The present invention relates to variable regions (V region) of a mouse monoclonal antibody to the human interleukin-6 receptor (IL-6R), human/mouse chimeric antibody to the human IL-6R, and reshaped human antibody comprising a human antibody wherein the complementarity determining regions (CDRS) of the human light chain (L chain) V region and of the human heavy chain (H chain) V region are grafted with the CDRs of a mouse monoclonal antibody to the human IL-6R. Moreover, the present invention provides DNA coding for the above-mentioned antibodies or part thereof. The present invention further provides vectors, especially expression vectors comprising said DNA, and host cells transformed or transfected with said vector. The present invention still more provides a process for production of a chimeric antibody to the human IL-6R, and process for production of a reshaped human antibody to the human IL-6R.

BACKGROUND ART

Interleukin-6 (IL-6) is a multi-function cytokine that is produced by a range of cells. It regulates immune responses, acute phase reactions, and hematopoiesis, and may play a central role in host defense mechanisms. It acts on a wide range of tissues, exerting growth-inducing, growth inhibitory, and differentiation-inducing effects, depending on the nature of the target cells. The specific receptor for IL-6 (IL-6R) is expressed on lymphoid as well as non-lymphoid cells in accordance with the multifunctional properties of IL-6. Abnormal expression of the IL-6 gene has been suggested to be involved in the pathogenesis of a variety of diseases, especially autoimmune diseases, mesangial proliferative glomerulonephritis, and plasmacytoma/myeloma (see review by Hirano et al., Immunol. Today 11, 443-449, 1990). Human myeloma cells are observed to produce IL-6 and express IL-6R. In experiments, antibody against IL-6 inhibited the in vitro growth of myeloma cells thus indicating that an autocrine regulatory loop is operating in oncogenesis of human myelomas (Kawano et al., Nature, 332, 83, 1988).

The IL-6R is present on the surface of various animal cells, and specifically binds to IL-6, and the number of IL-6R molecules on the cell surface has been reported (Taga et al., J. Exp. Med. 196, 967, 1987). Further, cDNA coding for a human IL-6R was cloned and a primary structure of the IL-6R was reported (Yamasaki et al., Science, 241, 825, 1988).

Mouse antibodies are highly immunogenic in humans and, for this reason, their therapeutic value in humans is limited. The half-life of mouse antibodies in vivo in human is relatively short. In addition, mouse antibodies can not be administered in multiple doses without generating an immune response which not only interferes with the planned efficacy but also risks an adverse allergic response in the patient.

To resolve these problems methods of producing humanized mouse antibodies were developed. Mouse antibodies can be humanized in two ways. The more simple method is to construct chimeric antibodies where the V regions are derived from the original mouse monoclonal antibody and the C regions are derived from suitable human antibodies. The resulting chimeric antibody contains the entire V domains of the original mouse antibody and can be expected to bind antigen with the same specificity as the original mouse antibody. In addition, chimeric antibodies have a substantial reduction in the percent of the protein sequence derived from a non-human source and, therefore, are expected to be less immunogenic than the original mouse antibody. Although chimeric antibodies are predicted to bind antigen well and to be less immunogenic, an immune response to the mouse V regions can still occur (LoBuglio et al., Proc. Natl. Acad. Sci. USA 84, 4220-4224, 1989).

The second method for humanizing mouse antibodies is more complicated but more extensively reduces the potential immunogenicity of the mouse antibody. In this method, the complementarity determining regions (CDRs) from the V regions of the mouse antibody are grafted into human V regions to create "reshaped" human V regions. These reshaped human V regions are then joined to human C regions. The only portions of the final reshaped human antibody derived from non-human protein sequences are the CDRS. CDRs consist of highly variable protein sequences. They do not show species-specific sequences. For these reasons, a reshaped human antibody carrying murine CDRs should not be any more immunogenic than a natural human antibody containing human CDRs.

As seen from the above, it is supposed that reshaped human antibodies are useful for therapeutic purposes, but reshaped human antibodies to the human IL-6R are not known. Moreover, there is no process for construction of a reshaped human antibodies, universally applicable to any particular antibody. Therefore to construct a fully active reshaped human antibody to a particular antigen, various devices are necessary. Even though mouse monoclonal antibodies to the human IL-6R, i.e., PM1 and MT18, were prepared (Japanese Patent Application No. 2-189420), and the present inventors prepared mouse monoclonal antibodies to the human IL-6R, i.e., AUK12-20, AUK64-7 and AUK146-15, the present inventors are not aware of publications which suggest construction of reshaped human antibodies to the human IL-6R.

The present inventors also found that, when the mouse monoclonal antibodies to the human IL-6R were injected into nude mice transplanted with a human myeloma cell line, the growth of the tumor was remarkably inhibited. This suggests that the anti-human IL-6 receptor antibody is useful as a therapeutic agent for the treatment of myeloma.

DISCLOSURE OF INVENTION

Therefore, the present invention is intended to provide a less immunogenic antibody to the human IL-6R. Accordingly, the present invention provides reshaped human antibodies to the human IL-6R. The present invention also provides human/mouse chimeric antibodies useful during the construction of the reshaped human antibody. The present invention further provides a part of reshaped human antibody, as well as the expression systems for production of the reshaped human antibody and a part thereof, and of the chimeric antibody.

More specifically, the present invention provides L chain V region of mouse monoclonal antibody to the human IL-6R; and H chain V region of a mouse monoclonal antibody to the human IL-6R.

The present invention also provides a chimeric antibody to the human IL-6R, comprising:
(1) an L chain comprising a human L chain C region and an L chain V region of a mouse monoclonal antibody to the IL-6R; and
(2) an H chain comprising a human H chain C region and an H chain V region of a mouse monoclonal antibody to the human IL-6R.

The present invention also provides CDR of an L chain V region of a mouse monoclonal antibody to the human IL-6R; and CDR of an H chain V region of a mouse monoclonal antibody to the human IL-6R.

The present invention moreover provides a reshaped human L chain V region of an antibody to the human IL-6R, comprising:
(1) framework regions (FRs) of a human L chain V region, and
(2) CDRs of an L chain V region of a mouse monoclonal antibody to the human IL-6R; and
a reshaped human H chain V region of an antibody to the human IL-6R comprising:
(1) FRs of a human H chain V region, and
(2) CDRs of an H chain V region of a mouse monoclonal antibody to the human IL-6R.

The present invention also provides a reshaped human L chain of an antibody to the human IL-6R, comprising:
(1) a human L chain C region; and
(2) an L chain V region comprising human FRs, and CDRs of a mouse monoclonal antibody to the human IL-6R; and
a reshaped human H chain of an antibody to the human IL-6R, comprising:
(1) a human H chain C region, and
(2) an H chain V region comprising a human FRs, and CDRs of a mouse monoclonal antibody to the human IL-6R.

The present invention still more provides a reshaped human antibody to the human IL-6R, comprising:
(A) an L chain comprising,
(1) a human L chain C region, and
(2) an L chain V region comprising human L chain FRs, and L chain CDRs of a mouse monoclonal antibody to the human IL-6R; and
(B) an H chain comprising,
(1) a human H chain C region, and
(2) an H chain V region comprising human H chain FRs, and H chain CDRs of a mouse monoclonal antibody to the human IL-6R.

The present invention further provides DNA coding for any one of the above-mentioned antibody polypeptides or parts thereof.

The present invention also provides vectors, for example, expression vectors comprising said DNA.

The present invention further provides host cells transformed or transfected with the said vector.

The present invention still more provide a process for production of a chimeric antibody to the human IL-6R, and a process for production of reshaped human antibody to the human IL-6R.

BEST MODE FOR CARRYING OUT THE INVENTION

Figure 1:
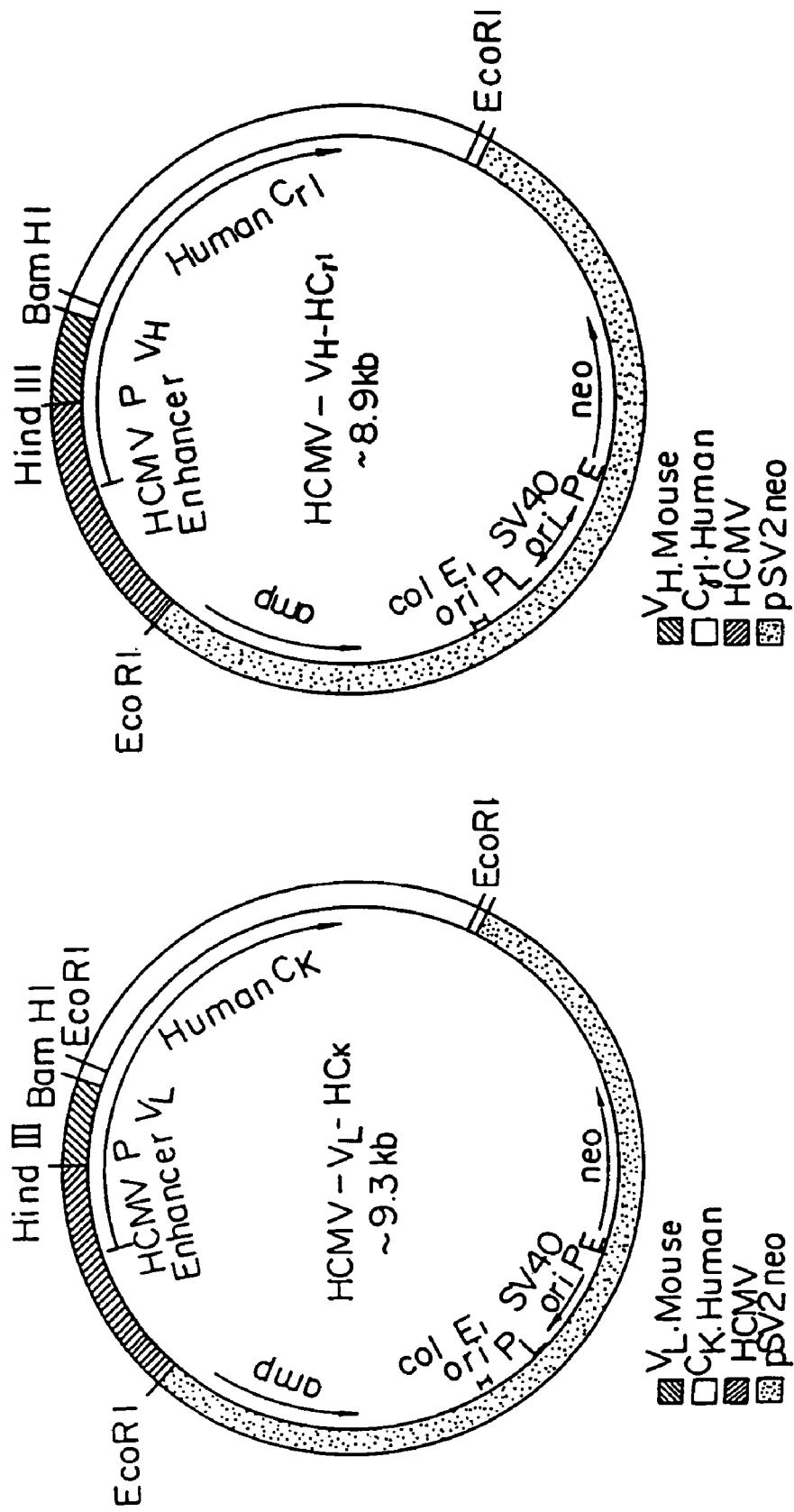
FIG. 1 represents expression vectors comprising human cytomegalo virus (HCMV) promoter/enhancer system, useful for the expression of the present antibody peptide.

Cloning of DNA Coding for Mouse V Regions

More specifically, to clone DNA coding for V regions of a mouse monoclonal antibody to a human IL-6R, the construction of hybridoma, which produces a monoclonal antibody to the human IL-6R, is necessary as a gene source. As such a hybridoma, Japanese Patent Application No. 2-189420 describes a mouse hybridoma PM-1 which produces a monoclonal antibody PM1 and the properties thereof. Reference Examples 1 and 2 of the present specification describe the construction process of the hybridoma PM1. The present inventors have constructed hybridomas AUK12-20, AUK64-7, and AUK146-15, each producing a mouse monoclonal antibody to the human IL-6R. The construction process of these hybridomas is described in the Reference Examples 3 of this specification.

To clone desired DNAs coding for V regions, of a mouse monoclonal antibody, hybridoma cells are homogenized and a total RNA is obtained according to a conventional procedure described by Chirgwin et al., Biochemistry 18, 5294, 1977. Next, the total RNA is used to synthesize single-stranded cDNAs according to the method described by J. W. Larrick et al., Biotechnology, 7, 934, 1989.

Next, a specific amplification of a relevant portion of the cDNA is carried out by a polymerase chain reaction (PCR) method. For amplification of a κ L chain V region of a mouse monoclonal antibody, 11 groups of oligonucleotide primers (Mouse Kappa Variable; MKV) represented in SEQ ID NO: 1 to 11, and an oligonucleotide primer (Mouse Kappa Constant; MKC) represented in SEQ ID NO: 12 are used as 5'-terminal primers and a 3'-terminal primer respectively. The MKV primers hybridize with the DNA sequence coding for the mouse κ L chain leader sequence, and the MKC primer hybridizes with the DNA sequence coding for the mouse κ L chain constant region. For amplification of the H chain V region of a mouse monoclonal antibody, 10 groups of oligonucleotide primers (Mouse Heavy Variable; MHV) represented in SEQ ID NO: 13 to 22, and a oligonucleotide primer (Mouse Heavy Constant MHC) represented in SEQ ID NO: 23 are used as 5'-terminal primers and a 3'-terminal primer, respectively.

Note, the 5'-terminal primers contain the nucleotide sequence GTCGAC near the 5'-end thereof, which sequence provides a restriction enzyme Sal I cleavage site; and the 3'-terminal primer contains the nucleotide sequence CCCGGG near the 5-end thereof, which sequence provides a restriction enzyme Xma I cleavage site. These restriction enzyme cleavage sites are used to subclone the DNA fragments coding for a variable region into cloning vectors.

Next, the amplification product is cleaved with restriction enzymes Sal I and Xma I to obtain a DNA fragment coding for a desired V region of a mouse monoclonal antibody. On the other hand, an appropriate cloning vector such as plasmid pUC19 is cleaved with the same restriction enzymes Sal I and Xma I and the above DNA fragment is ligated with the cleaved pUC19 to obtain a plasmid incorporating a DNA fragment coding for a desired V region of a mouse monoclonal antibody.

The sequencing of the cloned DNA can be carried out by any conventional procedure.

The cloning of the desired DNA, and the sequencing thereof, are described in detail in Examples 1 to 3.

Complementarity Determining Regions (CDRs)

The present invention provides hypervariable or complementarity determining regions (CDRs) of each V region of the present invention. The V domains of each pair of L and H chains from the antigen binding site. The domains on the L and H chains have the same general structure and each domain comprises four framework regions (FRs), whose sequences are relatively conserved, connected by three CDRs (see Kabat, E. A., Wu, T. T., Bilofsky, H., Reid-Miller, M. and Perry, H., in "Sequences of Proteins of Immunological Interest", US Dept. Health and Human Services 1983). The four FRs largely adopt a β-sheet conformation and the CDRs form loops connecting FRs, and in some cases forming part of, the β-sheet structure. The CDRs are held in close proximity by FRs and, with the CDRs from the other domain, contribute to the formation of the antigen binding site. The CDRs are described in Example 4.

Construction of Chimeric Antibody

Prior to designing reshaped human V regions of an antibody to the human IL-6R, it is necessary to confirm that the CDRs to be used actually form an effective antigen binding region. For this purpose, chimeric antibodies were constructed. In addition the amino acid sequences of V regions of mouse anti human IL-6R antibodies predicted from the nucleotide sequences of cloned DNAs of the 4 mouse monoclonal antibodies described in Example 1 and 2 were compared to each other and to V regions from known mouse and human antibodies. For each of the 4 mouse monoclonal antibodies, a set of typical, functional mouse L and H chain V regions had been cloned. All four mouse anti-IL-6R antibodies, however, had relatively distinct V regions. The 4 antibodies were not simply minor variations of each other. Using the cloned mouse V regions, 4 chimeric anti-IL-6R antibodies were constructed.

The basic method for constructing chimeric antibodies comprises joining the mouse leader and V region sequences, as found in the PCR-cloned cDNAs, to human C regions-coding sequence already present in mammalian cell expression vectors. Among said 4 monoclonal antibodies, construction of a chimeric antibody from the monoclonal antibody AUK12-20 is described in Example 5.

Construction of a chimeric antibody from the monoclonal antibody PM-1 is described in Example 6. The cDNA coding for the mouse PM-1 κ L chain leader and V region was PCR-subcloned into an expression vector containing a genomic DNA coding for the human kappa C region. The cDNA coding for the mouse PM-1 H chain leader and V regions was PCR-subcloned into an expression vector containing a genomic DNA coding for the human gamma-1 C region. Using specially designed PCR primers, the cDNA coding for the mouse PM-1 V region were adapted at their 5'- and 3'-ends (1) so that they would be easy to insert into the expression vectors and (2) so that they would function properly in these expression vectors. The PCR-modified mouse PM-1 V regions were then inserted into HCMV expression vectors already containing the desired human C regions (FIG. 1). These vectors are suitable for either transient or stable expression of genetically-engineered antibodies in a variety of mammalian cell lines.

In addition to constructing a chimeric PM-1 antibody with V regions identical to the V regions present in mouse PM-1 antibody (version a), a second version of chimeric PM-1 antibody was constructed (version b). In chimeric PM-1 antibody (version b), the amino acid at position 107 in the L chain V region was changed from asparagine to lysine. In comparing the L chain V region from mouse PM-1 antibody to other mouse L chain V regions, it was noticed that the occurrence of an asparagine at position 107 was an unusual event. In mouse κ L chain V regions, the most typical amino acid at position 107 is a lysine. In order to evaluate the importance of having the atypical amino acid asparagine at position 107 in the L chain V region of mouse PM-1 antibody, position 107 was changed to the typical amino acid lysine at this position. This change was achieved using a PCR-mutagenesis method (M. Kamman et al., Nucl. Acids Res. (1989) 17: 5404) to make the necessary changes in the DNA sequences coding for the L chain V region.

The chimeric PM-1 antibody version (a) exhibited an activity to bind to the human IL-6R. The chimeric MP-1 antibody version (b) also binds to the human IL-6R as well as version (a). Similarly, from other 2 monoclonal antibodies AUK64-7 and AUK146-15, chimeric antibodies were constructed. All 4 chimeric antibodies bound well to the human IL-6R thus indicating in a functional assay that the correct mouse V regions had been cloned and sequenced.

From the 4 mouse anti-IL-6R antibodies, PM-1 antibody was selected as the first candidate for the design and construction of a reshaped human antibody to the human IL-6R. The selection of mouse PM-1 antibody was based largely on results obtained studying the effect of the mouse anti-IL-6R antibodies on human myeloma tumor cells transplanted into nude mice. Of the 4 mouse anti-IL-6R antibodies, PM-1 antibody showed the strongest anti-tumor cell activity.

Comparison of the V Regions from Mouse Monoclonal Antibody PM-1 to V Regions from Known Mouse and Human Antibodies To construct a reshaped human antibody wherein the CDRs of a mouse monoclonal antibody are grafted into a human monoclonal antibody, it is desired that there is high homology between FRs of the mouse monoclonal antibody and FRs of the human monoclonal antibody. Therefore, the amino acid sequences of the L and H chain V regions from mouse PM-1 antibody were compared to all known mouse and mouse V regions as found in the OWL (or Leeds) database of protein sequences.

With respect to V regions from mouse antibodies, the L chain V region of PM-1 antibody was most similar to the L chain V region of mouse antibody musigkcko (Chen, H.-T. et al., J. Biol. Chem. (1987) 262:13579-13583) with a 93.5% identity. The H chain V region of PM-1 antibody was most similar to the H chain V region of mouse antibody musigvhr2 (F. J. Grant et al., Nucl. Acids Res. (1987) 15:5496) with a 84.0% identity. The mouse PM-1 V regions show high percents of identity to known mouse V regions thus indicating that the mouse PM-1 V regions are typical mouse V regions. This provides further indirect evidence that the cloned DNA sequences are correct. There is generally a higher percent identity between the L chain V regions than between the H chain V regions. This is probably due to the lower amount of diversity generally observed in L chain V regions as compared to H chain V regions.

With respect to V regions from human antibodies, the L chain V region of PM-1 antibody was most similar to the L chain V region of human antibody klhure, also referred to as REI (W. Palm et al., Physiol. Chem. (1975) 356:167-191) with a 72.2% identity. The H chain V region of PM-1 antibody was most similar to the H chain V region of human antibody humighvap (VAP) (H. W. Schroeder et al., Science (1987) 238:791-793) with a 71.8% identity. The comparisons to human V regions are most important for considering how to design reshaped human antibodies from mouse PM-1 antibody. The percent identities to human V regions are less than the percent identities to mouse V regions. This is indirect evidence that the mouse PM-1 V regions do look like mouse V regions and not like human V regions. This evidence also indicates that it will be best to humanize mouse PM-1 V regions in order to avoid problems of immunogenicity in human patients.

The V regions from mouse PM-1 antibody were also compared to the consensus sequences for the different subgroups of human V regions as defined by E. A. Kabat et al. ((1987) Sequences of Proteins of Immunological Interest, Forth Edition, U.S. Department of Health and Human servides, U.S. Government Printing is Office). The comparisons were made between the FRs of the V regions. The results are shown in Table 1.

TABLE 1

Percent identities between the FRs from the mouse PM-1 V regions and the FRs from the consensus sequences[1] for the different subgroups of human V regions.

| A. FRs in the L chain V regions | | | |
|---|---|---|---|
| HSGI | HSGII | HSGIII | HSGIV |
| 70.1 | 53.3 | 60.7 | 59.8 |

| B. FRs in the H chain V regions | | |
|---|---|---|
| HSGI | HSGII | HSGIII |
| 44.1 | 52.9 | 49.2 |

[1]The consensus sequences were taken from the subgroups of human V regions as described in Kabat et al., (1987).

The FRs of mouse PM-1 L chain V region are most similar to the FRs from the consensus sequence for subgroup I (HSGI) of human L chain V regions with 70.1% identity. The FRs of mouse PM-1H chain V region are most similar to the FRs from the consensus sequence for subgroup II (HSGII) of human H chain V regions with 52.9% identity. These results support the results obtained from the comparisons to known human antibodies. The L chain V region in human REI belongs to subgroup I of human L chain V regions and the H chain V region in human VAP belongs to subgroup II of human H chain V regions.

From these comparisons to the V regions in human antibodies, it is possible to select human V regions that will be the basis for the design of reshaped human PM-1 V regions. It would be best to use a human L chain V region that belongs to subgroup I (SGII) for the design of reshaped human PM-1 L chain V region and a human H chain V region that belongs to subgroup II (SGII) for the design of reshaped human PM-1 H chain V region.

Design of Reshaped Human PM-1 Variable Regions

The first step in designing the reshaped human PM-1 V regions was to select the human V regions that would be the basis of the design. The FRs in the mouse PM-1 L chain V region were most similar to the FRs in human L chain V regions belonging to subgroup I (Table 1). As discussed above, in comparing the mouse PM-1 L chain V region to known human L chain V regions, it was most similar to the human L chain V region REI, a member of subgroup I of human L chain V regions. In designing reshaped human PM-1 L chain V regions, the FRs from REI were used. Moreover the REI FRs were used as starting material for the construction of reshaped human PM-1 L chain V region.

In these human FRs based on REI, there were five differences from the FRs in the original human REI (positions 39, 71, 104, 105, and 107 according to Kabat et al., 1987; see Table 2). The three changes in FR4 (positions 104, 105, and 107) were based on a J region from another human kappa L chain and, therefore, do not constitute a deviation from human (L. Riechmann et al., Nature (1988) 322:21-25). The two changes at positions 39 and 71 were changes back to the amino acids that occurred in the FRs of rat CAMPATH-1 L chain V region (Riechmann et al., 1988).

Two versions of reshaped human PM-1 L chain V region were designed. In the first version (version "a"), the human FRs were identical to the REI-based FRs present in reshaped human CAMPATH-1H (Riechmann et al., 1988) and the mouse CDRs were identical to the CDRs in mouse PM-1 L chain V region. The second version (version "b") was based on version "a" with only one amino acid change at position 71 in human FR3. Residue 71 is part of the canonical structure for CDR1 of the L chain V region as defined by C. Chothia et al., (J. Mol. Biol. (1987) 196:901-917). The amino acid at this position is predicted to directly influence the structure of the CDR1 loop of the L chain V region and, therefore, may well influence antigen binding. In the mouse PM-1 L chain V region, position 71 is a tyrosine. In the modified REI FRs used in the design of version "a" of reshaped human PM-1 L chain V region, position 71 was a phenylalanine. In version "b" of reshaped human PM-1 L chain V region, the phenylalanine at position 71 was changed to a tyrosine as found in mouse PM-1 L chain V region. Table 2 shows the amino acid sequences of mouse PM-1 L chain V region, the FRs of REI as modified for use in reshaped human CAMPATH-1H antibody (Riechmann et al., 1988), and the two versions of reshaped human PM-1 L chain V region.

TABLE 2

Design of two different
versions of reshaped human
PM-1 L chain V region.

```
                    FR1                              CDR1

1          2                             3

12345678901234567890123               45678901234

V_LPM-1  DIQMTQTTSSLSASLGDRVTISC               RASQDISSYLN
(Residues
1-107
of
SEQ ID
NO:
29)

REI      DIQMTQSPSSLSASVGDRVTITC
(SEQ
ID
NO:
114)

RV_La    DIQMTQSPSSLSASVGDRVTITC               RASQDISSYLN
(Residues
1-107
of
SEQ ID
NO:
64)

RV_Lb    ----------------------                -----------
(SEQ
ID
NO:
115)

FR2                              CDR2

4                                        5

567890123456789                          0123456

V_LPM-1  WYQQKPDGTIKLLIY                          YTSRLHS

REI      WYQQKPGKAPKLLIY

RV_La    WYQQKPGKAPKLLIY                          YTSRLHS

RV_Lb    ---------------                          -------

FR3                              CDR3

6       7         8                         9

78901234567890123456789012345678       901234567
        z

V_LPM-1  GVPSRFSGSGSGTDYSLTINNLEQEDIATYFC       QQGNTLPYT

REI      GVPSRFSGSGSGTDFTFTISSLQPEDIATYYC

RV_La    GVPSRFSGSGSGTDFTFTISSLQPEDIATYYC       QQGNTLPYT

RV_Lb    --------------Y-----------------       ---------

FR4

10

8901234567

V_LPM-1  FGGGTKLEIN

REI      FGQGTKVEIK

RV_La    FGQGTKVEIK

RV_Lb    ----------
```

Note: The FRs given for REI are those found in the reshaped human CAMPATH-1H antibody (Riechmann et al., 1988). The five underlined amino acid residues in the REI FRs are those that differ from the amino acid sequence of human REI (Palm et al., 1975; O. Epp et al., Biochemistry (1975) 14: 4943-4952).

The FRs in the mouse PM-1 H chain V region were most similar to the FRs in human H chain V regions belonging to subgroup II (Table 1). As discussed above, in comparing the mouse PM-1 H chain V region to known human H chain V regions, it was most similar to the human H chain V region VAP, a member of subgroup II of human H chain V regions. DNA sequences coding for the FRs in human H chain V region NEW, another member of subgroup II of human H chain V regions, were used as starting material for the construction of reshaped human PM-1 H chain V region, and as a base for designing the reshaped human PM-1 H chain V region.

Six versions of reshaped human PM-1 H chain V region were designed. In all six versions, the human FRs were based on the NEW FRs present in reshaped human CAMPATH-1H (Riechmann et al., 1988) and the mouse CDRs were identical to the CDRs in mouse PM-1 H chain V region. Seven amino acid residues in the human FRs (positions 1, 27, 28, 29, 30, 48, and 71, see Table 3) were identified as having a possible adverse influence on antigen binding. In the model of mouse PM-1 V regions, residue 1 in the H chain V region is a surface residue that is located close to the CDR loops. Residues 27, 28, 29, and 30 are either part of the canonical structure for CDR1 of the H chain V region, as predicted by C. Chothia et al., Nature (1989) 34:877-883, and/or are observed in the model of the mouse PM-1 V regions to form part of the first structural loop of the H chain V region (Chothia, 1987). Residue 48 was observed in the model of the mouse PM-1 V regions to be a buried residue. Changes in a buried residue can disrupt the overall structure of the V region and its antigen-binding site. Residue 71 is part of the canonical structure for CDR2 of the H chain V region as predicted by Chothia et al., (1989). The six versions of reshaped human PM-1 antibody incorporate different combinations of amino acid changes at these seven positions in the human NEW FRs (see Table 3).

TABLE 3

Design of six different versions of reshaped human PM-1 H chain V region.

```
                              FR1                          CDR1

1         2         3
                    1234567890123456789012345 67890       123455
                                                               A

V_HPM-1             DVQLQESGPVLVKPSQSLSLTCTVTGYSIT         SDHAWS
(Residues
1-119 of
SEQ ID
NO: 31)

NEW                 QVQLQESGPGLVRPSQTLSLTCTVSGSTFS
(SEQ ID
NO: 116)

RV_Ha               QVQLQESGPGLVRPSQTLSLTCTVSGYTFT         SDHAWS
(SEQ ID
NO: 117)

RV_Hb               -------------------------Y--T          ------
(SEQ ID
NO: 118)

RV_Hc               D------------------------Y--T          ------
(SEQ ID
NO: 119)

RV_Hd               -------------------------Y--T          ------
(SEQ ID
NO: 120)

RV_He               D------------------------Y--T          ------
(SEQ ID
NO: 121)

RV_Hf               -------------------------YSIT          ------
(SEQ ID
NO: 122)

FR2                          CDR2

4                           5         6

67890123456789                 01223456789012345
                                                               A

V_HPM-1             WIRQFPGNKLEWMG                  YIS-YSGITTYNPSLKS

NEW                 WVRQPPGRGLEWIG
```

TABLE 3-continued

Design of six different versions of reshaped human PM-1 H chain V region.

| | | |
|---|---|---|
| RV$_H$a | WVRQPPGRGLEWIG | YIS-YSGITTYNPSLKS |
| RV$_H$b | -------------- | ----------------- |
| RV$_H$c | -------------- | ----------------- |
| RV$_H$d | ------------M- | ----------------- |
| RV$_H$e | ------------M- | ----------------- |
| RV$_H$f | -------------- | ----------------- |

```
              FR3
        7       8       9
   67890123456789012222345678901234
                   ABC
```

| | |
|---|---|
| V$_H$PM-1 | RISITRDTSKNQFFLQLNSVTTGDTSTYYCAR |
| NEW | RVTMLVDTSKNQFSLRLSSVTAADTAVYYCAR |
| RV$_H$a | RVTMLVDTSKNQFSLRLSSVTAADTAVYYCAR |
| RV$_H$b | -----R------------------------- |
| RV$_H$c | -----R------------------------- |
| RV$_H$d | -----R------------------------- |
| RV$_H$e | -----R------------------------- |
| RV$_H$f | -----R------------------------- |

```
      CDR3              FR4
       10                11
   5678900012        34567890123
       AB
```

| | | |
|---|---|---|
| V$_H$PM-1 | SLARTTAMDY | WGQGTSVTVSS |
| NEW | | WGQGSLVTVSS |
| RV$_H$a | SLARTTAMDY | WGQGSLVTVSS |
| RV$_H$b | ---------- | ----------- |
| RV$_H$c | ---------- | ----------- |
| RV$_H$e | ---------- | ----------- |
| RV$_H$e | ---------- | ----------- |
| RV$_H$f | ---------- | ----------- |

Note: The FRs given for NEW are those found in the first version of reshaped human CAMPATH-1H antibody (Riechmann et al., 1988).

Construction of Reshaped Human PM-1 V Regions

The first versions of the reshaped human PM-1 L and H chain V regions were each constructed using a novel PCR-based method. Essentially, a plasmid DNA coding for reshaped human V region that already contained suitable human FRs was modified using PCR primers to replace the CDRs present in the starting reshaped human V region with the CDRs from mouse PM-1 antibody. The starting material for the construction of the reshaped human PM-1 L chain V region was a plasmid DNA containing the reshaped human D1.3 L chain V region. The reshaped human D1.3 L chain V region was constructed based on the FRs present in the human L chain V region of REI. The starting material for the construction of the reshaped human PM-1 H chain V region was a plasmid DNA containing the reshaped human D1.3 H chain V region. The reshaped human D1.3 H chain V region was constructed based on the FRs present in the human H chain V region of NEW (M. Verhoeyen et al., Science (1988) 239: 1534-1536).

Once the starting plasmid DNAs containing the desired human FRS were selected, PCR primers were designed to enable the substitution of the mouse PM-1 CDRs in place of the mouse D1.3 CDRs. For each reshaped human PM-1 V region, three primers containing the DNA sequences coding for the mouse PM-1 CDRs and two primers flanking the entire DNA sequence coding for the reshaped human V region were designated and synthesized. Using the five PCR primers in a series of PCR reactions yielded a PCR product that consisted of the human FRs present in the starting reshaped human V region and the CDRs present in mouse PM-1 V region (see Example 7, and FIGS. 7 and 8). The PCR products were cloned and sequenced to ensure that the entire DNA sequence of version "a" of reshaped human PM-1 L and H chain V region coded for correct amino acid sequence (SEQ ID NO: 64).

The remaining versions of the reshaped human PM-1 V regions were constructed using slight modifications of published PCR-mutagenesis techniques (Kamman et al., 1989) As described for the design of the reshaped human PM-1 V regions, one additional version (version "b") of the reshaped human PM-1 L chain V region was constructed and five additional versions (versions "b", "c", "d", "e", and "f") of the reshaped human PM-1 H chain V region were constructed. These additional versions contain a series of minor changes from the first versions. These minor changes in the amino acid sequences were achieved using PCR mutagenesis to make minor changes in the DNA sequences. PCR primers were designed that would introduce the necessary changes into the DNA sequence. Following a series of PCR reactions, a PCR product was cloned and sequenced to ensure that the changes in the DNA sequence had occurred as planned. Sequence of the reshaped human PM-1 antibody H chain V region version "f" is shown in SEQ ID NO: 62).

Once the DNA sequences of the different versions of reshaped human PM-1 V regions were confirmed by sequencing, the reshaped human PM-1 V regions were subcloned into mammalian cell expression vectors already containing human C regions. Reshaped human PM-1 L chain V regions were joined to DNA sequences coding for human κ C region. Reshaped human PM-1 H chain V regions were joined to DNA sequences coding for human gamma-1 C region. In order to achieve higher levels of expression of the reshaped human PM-1 antibodies, the HCMV expression vectors, as shown in FIG. 1, were modified to replace the HCMV promoter-enhancer region with the human elongation factor (HEF-1α) promoter-enhancer (see FIG. 15).

Next, all combinations of the reshaped human L chain versions (a) and (b) with the H chain V region versions (a) to (f) were tested for biding to human IL-6R, and as a result, a reshaped human antibody comprising the L chain version (a) and the H chain version (f) exhibited an ability to bind to IL-6R at a same level as that of chimeric PM-1 (a) (FIG. 13) as described in detail in Example 11.

Modifications in the DNA Sequences Coding for the Reshaped Human PM-1 V Regions to Improve the Levels of Expression.

In reviewing the levels of reshaped human PM-1 antibodies being produced in cos cells, it became apparent that the levels of expression of the reshaped human H chains were always approximately 10-fold lower than the levels of expression of the reshaped human L chains or of the chimeric L or H chains. It appeared that there was a problem in DNA coding for the reshaped human H chain V region that caused low levels of expression. In order to identify whether the lower levels of protein expression were the result of lower levels of transcription, RNA was prepared from cos cells co-transfected with vectors expressing reshaped human PM-1 L and H chains. First-strand cDNA was synthesized as described for the PCR cloning of the mouse PM-1 V regions. Using PCR primers designed to flank the ends of DNA coding for the reshaped human L or H chain V regions, PCR products were generated from the cDNAs that corresponded to reshaped human L chain V region or to reshaped human H chain V region.

For the reshaped human L chain V region, there were two PCR products, one 408 bp long, as expected, and a shorter PCR product 299 bp long. The correct size PCR product made up approximately 90% of the total yield of PCR product and the shorter PCR product made up approximately 10% of the total yield. For the reshaped human H chain V region, there were also two PCR products, one 444 bp long, as expected, and a shorter PCR product 370 bp long. In this case, however, the incorrect, shorter PCR product made up the majority of the total yield of PCR product, approximately 90%. The correct size PCR product made up only approximately 10% of the total yield of PCR product. These results indicated that some of the RNAs coding for the reshaped human V regions contained deletions.

In order to determine which sequences were being deleted, the shorter PCR products were cloned and sequenced. From the DNA sequences, it became clear that for both the L and H chain V regions specific sections of DNA were being deleted. Examination of the DNA sequences flanking the deleted sequences revealed that these sequences corresponded to the consensus sequences for splice donor-acceptor sequences (Breathnach, R. et al., Ann. Rev. Biochem (1981) 50:349-383). The explanation for the low levels of expression of the reshaped human H chains was that the design of the reshaped human H chain V regions had inadvertently created a rather efficient set of splice donor-acceptor sites. It also appeared that the design of the reshaped human L chain V regions had inadvertently created a rather inefficient set of splice donor-acceptor sites. In order to remove the splice donor-acceptor sites, minor modifications in the DNA sequences coding for versions "a" and "f", respectively, of the reshaped human PM-1 L and H chain V regions were made using the PCR-mutagenesis methods described earlier.

Another possible cause of reduced levels of expression was thought to be the presence of introns in the leader sequences in both the reshaped human L and H chain V regions (SEQ ID NOs: 61 and 63). These introns were originally deived from a mouse mu H chain leader sequence (M.S. Neuberger et al., Nature 1985 314:268-270) that was used in the construction of reshaped human D1.3 and V regions (Verhoeyen et al., 1988). Since the reshaped human D1.3 was expressed in a mammalian cell vector that employed a mouse immunoglobulin promoter, the presence of the mouse leader intron was important. The leader intron contains sequences that are important for expression from immunoglobulin promoters but not from viral promoters like HCMV (M.S. Neuberger et al., Nucl. Acids Res. (1988) 16:6713-6724). Where the reshaped human PM-1 L and H chains were being expressed in vectors employing non-immunoglobulin promoters, the introns in the leader sequences were deleted by PCR cloning cDNAs coding for the reshaped human V regions (see Example 12).

Another possible cause of reduced levels of expression was thought to be the presence of a stretch of approximately 190 bp of non-functional DNA within the intron between the reshaped human PM-1 H chain V region and the human gamma-1 C region. The reshaped human PM-1 H chain V region was constructed from DNA sequences derived originally from reshaped human B1-8 H chain V region (P. T. Jones et al., Nature (1986) 321:522-525). This first reshaped human V region was constructed from the mouse NP H chain V region (M. S. Neuberger et al., Nature (1985); M. S. Neuberger et al., EMBO J. (1983) 2:1373-1378). This stretch of approximately 190 bp occurring in the intron between the reshaped human. H chain V region and the BamHI site for joining of the reshaped human V regions to the expression vector was removed during the PCR cloning of cDNAs coding for the reshaped human V regions.

The DNA and amino acid sequences of the final versions of reshaped human PM-1 L and H chain V regions, as altered to improve expression levels, are shown in SEQ ID NOs: 67 and 68, and SEQ ID NOs: 65 and 66. These DNA sequences code for version "a" of the reshaped human PM-1 L chain V region as shown in Table 2 and version "f" of the reshaped human PM-1 H chain V region as shown in Table 3. When inserted into the HEF-1α expression vectors (FIG. 15), these vectors transiently produce approximately 2 μ/ml of antibody in transfected cos cells. In order to stably produce larger amounts of reshaped human PM-1 antibody, a new HEF-1α expression vector incorporating the dhfr gene was constructed (see Example 10, FIG. 11). The "crippled" dhfr gene was introduced into the HEF-1α vector expressing human gamma-1 H chains as was described for the HCMV vector expressing human gamma-1 H chains. The HEF-1α vector expressing reshaped human PM-1 L chains and the HEF-1α-dhfr vector expressing reshaped human PM-1 H chains were co-transfected into CHO dhfr(−) cells. Stably transformed CHO cell lines were selected in Alpha-Minimum Essential Medium (α-MEM) without nucleosides and with 10% FCS and 500 μg/ml of G418. Prior to any gene amplification steps, CHO cell lines were observed that produced up to 10 μg/$10^6$ cells/day of reshaped human PM-1 antibody.

Comparison of V Regions from Mouse Monoclonal Antibody AUK 12-20 to V Regions from Known Human Antibodies The homology of FRs of KL chain V region of the mouse monoclonal antibody AUK 12-20 with FRs of human KL chain V region subgroup (HSG) I to IV, and the homology of FRs of H chain V region of the mouse monoclonal antibody AUK 12-20 will FRs of human H chain V regions subgroup (HSG) I to III are shown in Table 4.

TABLE 4

Percent identities between FRs from the mouse AUK 12-20 V regions and FRs from the consensus sequence for the different subgroups of human V regions

| FRs in the L chain V regions | | | |
|---|---|---|---|
| HSG1 | HSG2 | HSG3 | HSG4 |
| 65.8 | 64.0 | 67.6 | 67.6 |

| FRs in the H chain V regions | | |
|---|---|---|
| HSGI | HSGII | HSGIII |
| 58.6 | 53.6 | 49.1 |

As seen from Table 4, the KL chain V region of the mouse monoclonal antibody AUK 12-20 is homologous in a similar extent (64 to 68%) with the human κL chain V region subgroups (HSG) I to IV. In a search of the Data base "LEEDS" for protein, L chain V region of human antibody Len (M. Schneider et al., Physiol. Chem. (1975) 366:507-557) belonging to the HSG-IV exhibits the highest homology 68%. On the other hand, the human antibody REI, used for construction of a reshaped human antibody from the mouse monoclonal antibody PM-1 belongs to the HSG I, exhibits a 62% homology with L chain V region of the mouse monoclonal antibody AUK 12-20. In addition, the CDRs in the AUK 12-20 antibody L chain V region particularly CDR2, corresponded better to canonical structures of the CDRs in REI rather than those in LEN.

Considering the above, it is not necessary to choose a human antibody used for humanization of the mouse monoclonal antibody AUK 12-20 L chain V region from those antibodies belonging to the HSG IV. Therefore, as in the case of the humanization of the mouse monoclonal antibody PM-1 L chain V region, the FRs of REI are used for humanization of the mouse monoclonal antibody AUK 12-20 L chain V region.

As shown in Table 4, H chain V region of the antibody AUK 12-20 exhibits the highest homology with the HSG I. Moreover, in a search of Data base "LEEDS", human antibody HAX (Stollar, B. O. et al., J. Immunol. (1987) 139:2496-2501) also belonging to the HSG I exhibits an about 66% homology with the AUK 12-20 antibody H chain V region. Accordingly, to design reshaped human AUK 12-20 antibody H chain V region, the FRs of the human antibody HAX belonging to the HSG I, and FRs of humanized 425 antibody H chain V region which has FRs consisting of HSGI consensus sequence (Ketteborough C. A. et al., Protein Engineering (1991) 4:773-783) are used. Note, the AUK 12-20 antibody H chain V region exhibits an about 64% homology with version "a" of the humanized 425 antibody H chain V region.

Design of Reshaped Human AUK 12-20 Antibody L Chain V Regions

According to the above reason, reshaped human AUK 12-20 antibody L chain V regions is designed as shown in Table 5 using FRs of the REI.

TABLE 5

| | FR1 | CDR1 |
|---|---|---|
| | 1            2 | 3 |
| | 12345678901234567890123 | 45677778901234 |
| | | ABCD |
| $V_L$AUK 12-20 (Residues 1-111 of SEQ ID NO: 25) | DIVLTQSPASLGVSLGQRATISC | RASKSVSTSGYSYMI |

TABLE 5-continued

| | | |
|---|---|---|
| REI (SEQ ID NO: 123) | DIQMTQSPSSLSASVGDRVTITC | |
| RV$_L$ (SEQ ID NO: 124) | DIQMTQSPSSLSASVGDRVTITC | RASKSVSTSGYSYMI |
| | FR2 | CDR2 |
| | 4 | 5 |
| | 567890123456789 | 0123456 |
| V$_L$AUK 12-20 | WYQQKPGQTPKLLIY | ASNLES |
| REI | WYQQTPGKAPKLLIY | |
| RV$_L$ | WYQQKPGKAPKLLIY | ASNLES |
| | FR3 | CDR3 |
| | 6  7  8 | 9 |
| | 78901234567890123456789012345678 | 901234567 |
| V$_L$AUK 12-20 | GVPARFSGSGSGTDFTLNIHPVEEEDAATYYC | QHSRENPYT |
| REI | GVPSRFSGSGSGTDYTFTISSLQPEDIATYYC | |
| RV$_L$ | GVPSRFSGSGSGTD<u>F</u>TFTISSLQPEDIATYYC | QHSRENPYT |
| | FR4 | |
| | 10 | |
| | 8901234567 | |
| V$_L$AUK 12-20 | FGGGTKLEIk | |
| REI | FGQGTKLQIT | |
| RV$_L$ | FGQGTK<u>VEIK</u> | |

Note: 5 underlined nucleotides are those changed in the design of CAMPATH-1H antibody (see the note of Table 2).

Design of Reshaped Human AUK 12-20 Antibody H Chain V Regions

According to the above reason, reshaped human AUK 12-20 antibody H chain V regions are designed using FRs of the reshaped human VHa 425. It is found, however, that nucleotide sequence of DNA coding for reshaped human AUK 12-20 antibody H chain V region thus designed has a sequence well conforming to a splicing donor sequence. Therefore, as in the case of reshaped human PM-1 antibody there is a possibility of an abnormal splicing in the reshaped human AUK 12-20 antibody. Therefore, the nucleotide sequence was partially modified to eliminate the splicing donor-like sequence. The modified sequence is designated as version "a".

In addition, version "b" to "d" of the reshaped human AUK 12-20 antibody H chain V region were designed. Amino acid sequences of the versions "a" to "d" are shown in Table 6.

TABLE 6

| | FR1 | CDR1 |
|---|---|---|
| | 1  2  3 | |
| | 12345678901234567890123456789012345 | 12345 |
| V$_H$AUK 12-20 (Residues 1-116 of SEQ ID NO: 27) | EIQLQQSGPELMKPGASVKISCKASGYSFT | SYYIH |
| SGI (SEQ ID NO: 125) | ZVQLVQSGAEVKKPGXSVXVSCKASGYTFS | |

TABLE 6-continued

| | | |
|---|---|---|
| RV$_H$a (SEQ ID NO: 126) | QVQLVQSGAEVKKPGASVKVSCKASGY<u>SFT</u> | SYYIH |
| RV$_H$b (SEQ ID NO: 127) | ---------------------------- | ------ |
| RV$_H$c (SEQ ID NO: 128) | ---------------------------- | ------ |
| RV$_H$d (SEQ ID NO: 129) | ---------------------------- | ------ |

```
                    FR2                              CDR2

4                            5         6

67890123456789               01223456789012345
                                                     A

V_H AUK 12-20   WVKQSHGKSLEWIG                 YIDPFNGGTSYNQKFKG

SGI             WVRQAPGXGLEWVG

RV_H a          WVRQAPGQGLEWVG                 YIDPFNGGTSYNQKFKG

RV_H b          --------------                 -----------------

RV_H c          ------------I-                 -----------------

RV_H d          ------------I-                 -----------------

FR3

7         8         9

67890123456789012222345678901234
                                    ABC

V_H AUK 12-20   KATLTVDKSSSTAYMHLSSLTSEDSAVYYCAR

SGI             RVTXTXDXSXNTAYMELSSLRSEDTAVYYCAR

RV_H a          RVTMTLDTSTNTAYMELSSLRSEDTAVYYCAR

RV_H b          K----V--------------------------

RV_H c          --------------------------------

RV_H d          K----V--------------------------

CDR3                          FR4

10                            11

5678900012                    34567890123
                        AB

V_H AUK 12-20   GGN-RF--AY                    WGQGTLVTVSA

SGI                                           WGQGTLVTVSS

RV_H a          GGN-RF--AY                    WGQGTLVTVSS

RV_H b          ----------                    -----------
```

TABLE 6-continued

| | | |
|---|---|---|
| RV$_H$c | ---------- | ---------- |
| RV$_H$d | ---------- | ---------- |

Note: The position where one common amino acid residue is not identified in the HSG I V$_H$ regions (SGI) is shown as "X". Two under lined amino acid residues are different from those in SGI consensus sequence. For RV$_H$b, RV$_H$c and RV$_H$d, only amino acid residues different from those of RV$_H$a are shown.

Figure 4:
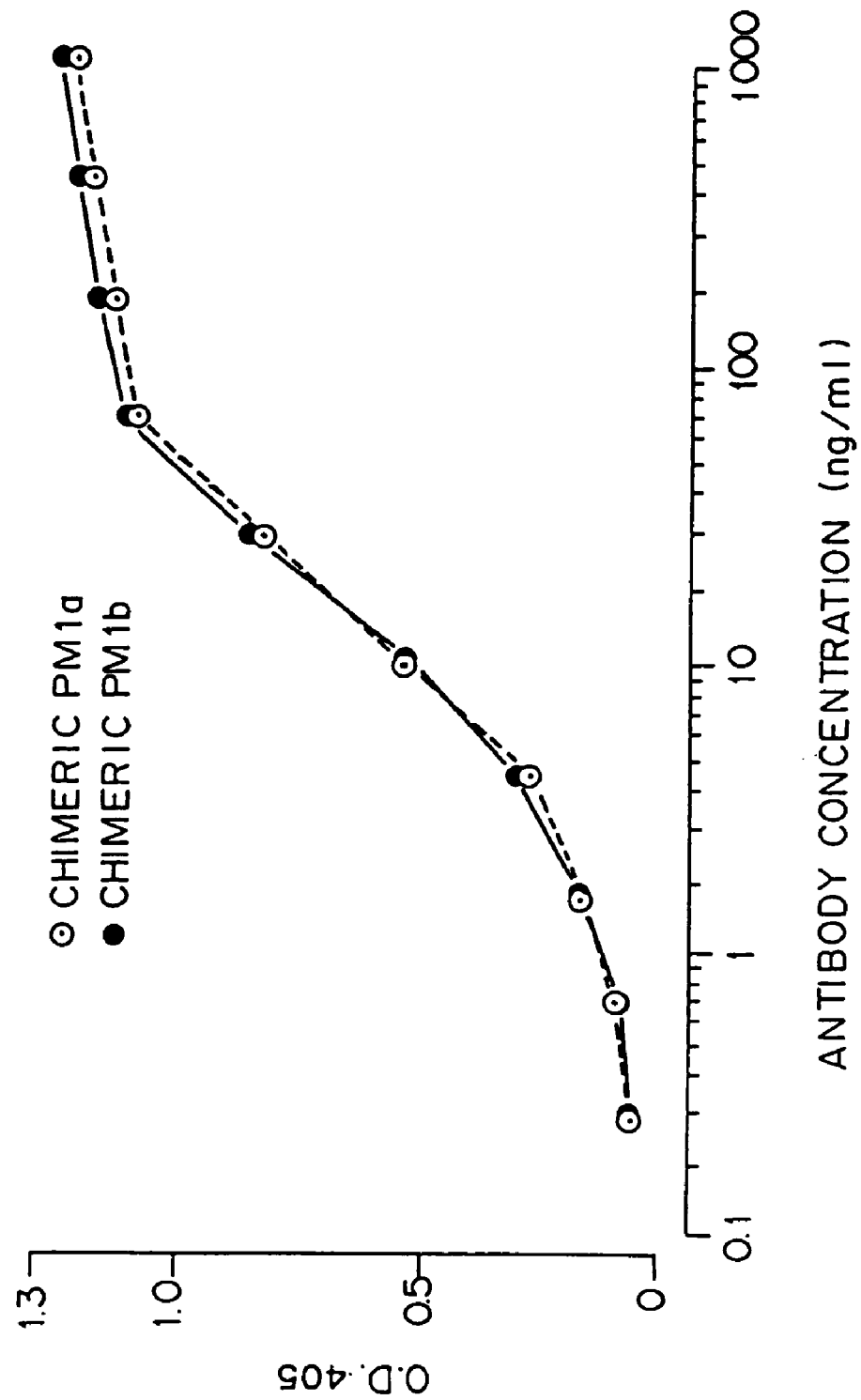
FIG. 4 is a graph showing a result of ELISA for binding of the present chimeric antibodies PM1a and PM1b to human IL-6R.
Figure 6:
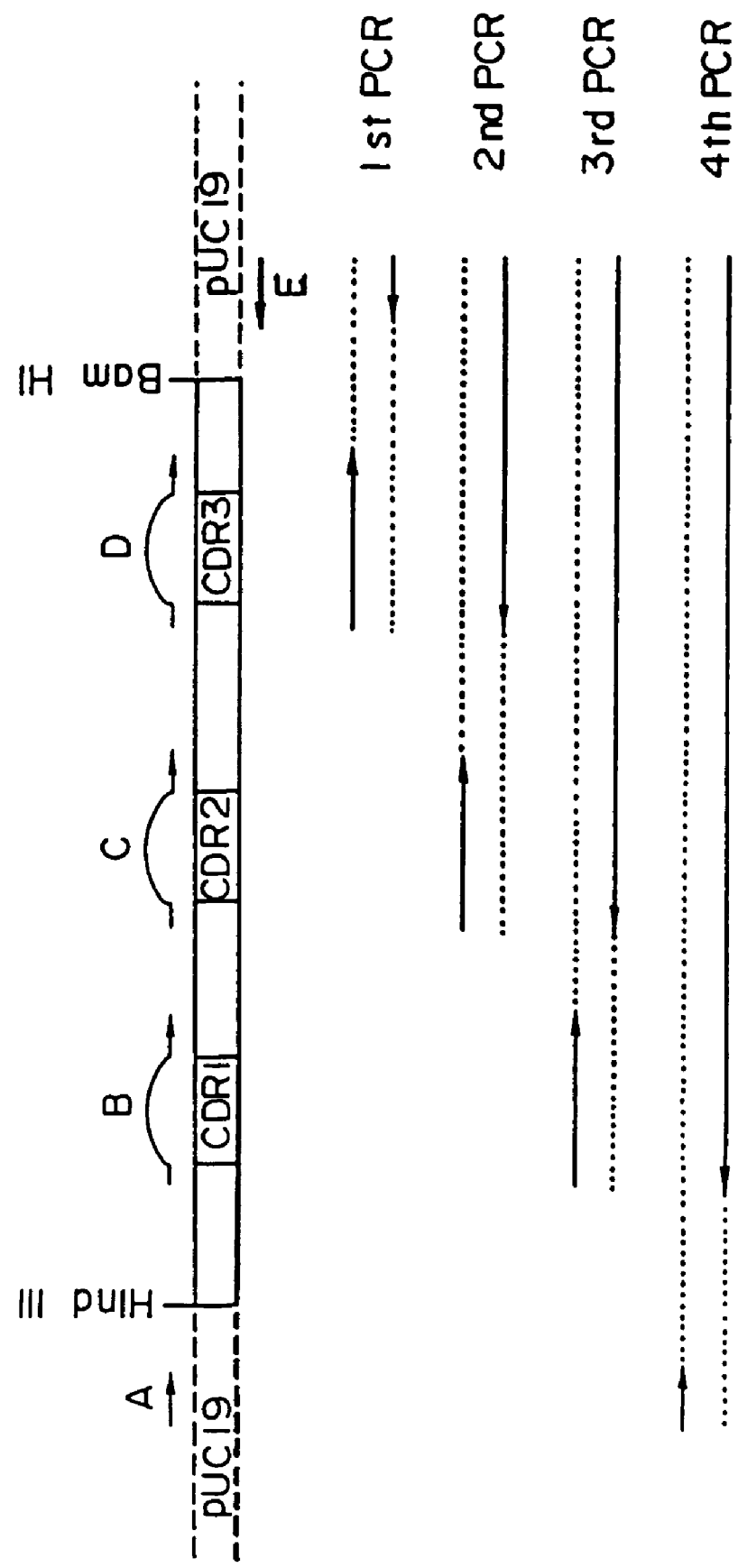
FIG. 6 is a diagram of the construction of the first version of a reshaped human PM-1 H chain V region.

Moreover, version "a" to "d" of reshaped human AUK 12-20 antibody H chain V region are designed as shown in Table 7, using FRs of the human antibody HAX (J. Immunology (1987) 139:2496-2501; an antibody produced by hybridoma 21/28 cells derived from B cells of a SLE patient; its amino acid sequence is described in FIG. 6 and nucleotide sequence of DNA coding for the amino acid sequence is shown in. FIGS. 4 and 6, of this literatures.

TABLE 7

| | FR1 | CDR1 |
|---|---|---|
| | 1         2         3 | |
| | 123456789012345678901234567890 | 12345 |
| V$_H$AUK 12-20 (Residues 1-116 of SEQ ID NO: 27) | EIQLQQSGPELMKPGASVKISCKASGYSFT | SYYIH |
| HAX (SEQ ID NO: 130) | QVQLVQSGAEVKKPGASVKVSCKASGYTFT | |
| Sle: | | |
| 1220Ha (SEQ ID NO: 131) | QVQLVQSGAEVKKPGASVKVSCKASGY<u>S</u>FT | SYYIH |
| 1220Hb (SEQ ID NO: 132) | --------------------------S-- | |
| 1220Hc (SEQ ID NO: 133) | --------------------------S-- | |
| 1220Hd (SEQ ID NO: 134) | --------------------------S-- | |
| | FR2 | CDR2 |
| | 4 | 5         6 |
| | 67890123456789 | 0122223456789012345 |
| | | ABC |
| V$_H$AUK 12-20 | WVKQSHGKSLEWIG | YIDP--FNGGTSYNQKFKG |
| HAX | WVRQAPGQRLEWMG | |
| sle: | | |
| 1220Ha | WVRQAPGQRLEWMG | YIDP--FNGGTSYNQKFKG |
| 1220Hb | ------------I- | ------------------- |

TABLE 7-continued

```
1220Hc       --------------             -------------------

1220Hd       ------------I-             -------------------
                           FR3
                      7         8         9
                 67890123456789012222345678901234
                                 ABC

V_HAUK 12-20 KATLTVDKSSSTAYMHLSSLTSEDSAVYYCAR

HAX          RVTITRDTSASTAYMELSSLRSEDTAVYYCAR sle:

1220Ha       RVTITVDTSASTAYMELSSLRSEDTAVYYCAR
                  ‾
1220Hb       -----V--------------------------

1220Hc       K----V--------------------------

1220Hd       K----V--------------------------

CDR3                      FR4
                    10                        11
                 5678900012               34567890123
                     AB

V_HAUK 12-20 GGN-RF--AY                WGQGTLVTVSA

HAX                                    WGQGTLVTVSS sle:

1220Ha       GGN-RF--AY                WGQGTLVTVSS

1220Hb       ----------                -----------

1220Hc       ----------                -----------

1220Hd       ----------                -----------
```

Note: The two underlined residues in sle1220Ha are changes from the HAX FRs. For sle1220Hb, sle1220Hc, and sle1220Hd, only the anino acids in the FRs that differ from those in the HAX FRs are shown.

For the production of the present chimeric or reshaped human antibodies to the human IL-6R, any expression system, including eucaryotic cells, for example, animal cells, such as established mammalian cell lines, fungal cells, and yeast cells, as well as procaryotic cells, for example, bacterial cells such as *E. coli* cells, may be used. Preferably the present chimeric or reshaped human antibodies are expressed in mammalian cells such as cos cells or CHO cells.

In such cases, a conventional promoter useful for the expression in mammalian cells can be used. For example, viral expression system such as human cytomegalovirus immediate early (HCMV) promoter is preferably used. Examples of the expression vector containing the HCMV promoter include HCMV-VB-HCγl, HCMV-$V_L$-$HC_K$, HCMV-12h-gγl, HCMV-12k-gk and the like derived from pSV2neo, as shown in FIG. 1.

Figure 15:
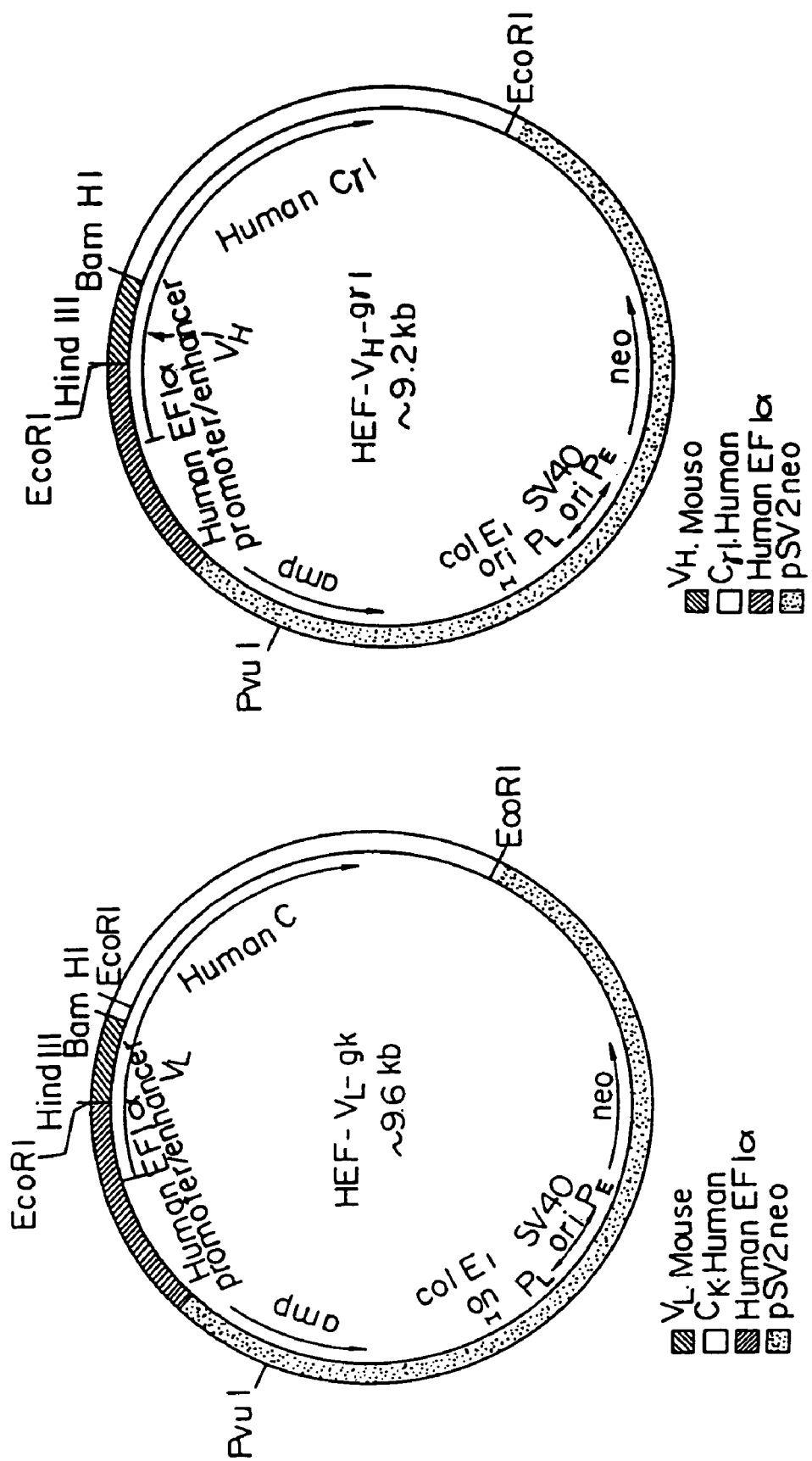
FIG. 15 represents expression plasmids HEF-$V_L$-gk and HEF-$V_H$-gγ1 comprising a human EF1-α promoter/enhancer, useful for expression of an L chain and H chain respectively.

Another embodiment of promoter useful for the present invention is the human elongation factor 1α (HEF-1α) promoter. Expression vectors containing this promotor include HEF-12h-gγl and HEF-12h-gκ (FIGS. 8 and 9), as well as HEF-VB-gγl and HEF-$V_L$-gκ (FIG. 15).

For gene amplification dhfr in a host cell line, an expression vector may contain a dhfr gene. Expression vectors containing the dhfr gene, are for example, DHFR-ΔE-PMh-gγl (FIG. 10), DHFR-ΔE-RVh-PM1-f (FIG. 11) and the like.

In summary, the present invention first provides an L chain V region and an H chain V region of a mouse monoclonal antibody to the human IL-6R, as well as DNA coding for the L chain V region and DNA coding for the H chain V region. These are useful for the construction of a human/mouse chimeric antibody and reshaped human antibody to the human IL-6R. The monoclonel antibodies are, for example, AUK12-20, PM-1, AUK64-7 and AUK146-15. The L chain V region has an amino acid sequence shown in, for example, SEQ ID NOs: 25, 29, 33 or 37; and the H chain V region has an amino acid sequence shown in SEQ ID NOs: 27, 31, 35 or 39. These amino acid sequences are encoded by nucleotide sequences, for example, shown in SEQ ID NOs: 24, 26, 28, 30, 32, 34, 36 and 38.

The present invention also relates to a chimeric antibody to the human IL-6R, comprising:
(1) an L chain comprising a human L chain C region and a mouse L chain V region; and
(2) an H chain comprising a human H chain C region and a mouse H chain V region. The mouse L chain V region and the mouse H chain V region and DNA encoding them are as described above. The human L chain C region may be any human L chain C region, and for example, is human $C_\kappa$. The human H chain C region may be any human H chain C region, and for example human $C_{\gamma l}$.

For the production of the chimeric antibody, two expression vectors, i.e., one comprising a DNA coding for a mouse L chain V region and a human L chain C region under the control of an expression control region such as an enhancer/promoter system, and another comprising a DNA coding for a mouse H chain V region and a human H chain C region under the expression control region such as an enhancer/promotor system, are constructed. Next, the expression vectors are co-transfected to host cells such as mammalian cells, and the transfected cells are cultured in vitro or in vivo to produce a chimeric antibody.

Alternatively, a DNA coding for a mouse L chain V region and a human L chain C region and a DNA coding for a mouse H chain V region and a human H chain C region are introduced into a single expression vector, and the vector is used to transfect host cells, which are then cultured in-vivo or in-vitro to produce a desired chimeric antibody.

The present invention further provides a reshaped antibody to the human IL-6R, comprising:
(A) an L chain comprising,
(1) a human L chain C region, and
(2) an L chain V region comprising a human L chain FRs, and L chain CDRs of a mouse monoclonal antibody to the human IL-6R; and
(B) an H chain comprising,
(1) a human H chain C region, and
(2) an H chain V region comprising human H chain FRs, and H chain CDRs of a mouse monoclonal antibody to the IL-6R.

In a preferred embodiment, the L chain CDRs have amino acid sequences shown in any one of SEQ ID NOs: 25, 29, 33 and 37 wherein the stretches of the amino acid sequences are defined in Table 9; the H chain CDRs have amino acid sequences shown in any one of SEQ ID NOs: 27, 31, 35 and 39 wherein the stretches of the amino acid sequences are defined in Table 9; human L chain FRs are derived from the RET; and human H chain FRs are derived from the NEW or HAX.

In the preferred embodiment, the L chain V region has an amino acid sequence shown in Table 2 as $RV_L a$; and the H chain V region has an amino acid sequence shown in Table 3 as $RV_H a$, $RV_H b$, $RV_H C$, $RV_H D$, $RV_H e$ or $RV_H f$. The amino acid sequence $RV_H f$ is most preferable.

For the production of the reshaped human antibody, two expression vectors, i.e., one comprising a DNA coding for the reshaped L chain as defined above under the control of an expression control region such as an enhancer/promoter system, and another comprising a DNA coding for the reshaped human H chain as defined above under the expression control region such as an enhancer/promoter system, are constructed. Next, the expression vectors are co-transfected to host cells such as mammalian cells, and the transfected cells are cultured in vitro or in-vivo to produce a reshaped human antibody.

Alternatively, a DNA coding for the reshaped human L chain and a DNA coding for the reshaped H chain are introduced into a single expression vector, and the vector is used to transfect host cells, which are then cultured in vivo or in vitro to produce a desired reshaped human antibody.

A chimeric antibody of a reshaped human antibody thus produced can be isolated and purified be a conventional processes such as Protein A affinity chromatography, ion exchange chromatography, gel filtration and the like.

The present chimeric L chain or reshaped human L chain can be combined with an H chain to construct a whole antibody. Similarly, the present chimeric H chain or reshaped human H chain can be combined with an L chain to construct a whole antibody.

The present mouse L chain V region, reshaped human L chain V region, mouse H chain V region and reshaped human H chain V region are intrinsically a region which binds to an antigen, human IL-6R, and therefore considered to be useful as such or as a fused protein with other protein, for preparing pharmacenticals or diagnostic agents.

Moreover, the present L chain V region CDRs and H chain V region CDRs are intrinsically regions which bind to an antigen, human IL-6R, and therefore considered to be useful as such or as a fused protein with other protein, for preparing pharmacenticals or diagnostic agents.

DNA coding for a mouse L chain V region of the present invention is useful for construction of a DNA coding for a chimeric L chain or a DNA coding for a reshaped human L chain.

Similarly, DNA coding for a mouse H chain V region of the present invention is useful for construction of a DNA coding for a chimeric H chain or a DNA coding for a reshaped human H chain. Moreover, DNA coding for L chain V region CDR of the present invention is useful for construction of a DNA coding for a reshaped human L chain V region and a DNA coding for a reshaped human L chain. Similarly, DNA coding for H chain V region CDR of the present invention is useful for construction of a DNA coding for a reshaped human H chain V region and a DNA coding for a reshaped human H chain.

EXAMPLES

The present invention will be further illustrated by, but is by no means limited to, the following Examples.

Example 1

Cloning of DNA Coding for V Region of Mouse Monoclonal Antibody to Human IL-6R (1)

A DNA coding for the V region of a mouse monoclonal antibody to a human IL-6R was cloned as follows.

1. Preparation of Total RNA

Total RNA from hybridoma AUK12-20 was prepared according to a procedure described by Chirgwin et al., Biochemistry 18, 5294 (1979). Namely, $2.1 \times 10^8$ cells of the hybridoma AUK12-20 were completely homogenized in 20 ml of 4 M guanidine thiocyanate (Fulka). The homogenate was layered over a 5.3 M cesium chloride solution layer in a centrifuge tube, which was then centrifuged in a Beckman SW40 rotor at 31000 rpm at 20° C. for 24 hours to precipitate RNA. The RNA precipitate was washed with 80% ethanol and dissolved in 150 μl of 10 mM Tris-HCl (pH 7.5) containing 1 mM EDTA and 0.5% SDS, and after adding Protenase (Boehringer) thereon to 0.5 mg/ml, incubated at 37° C. for 20 minutes. The mixture was extracted with phenol and chloroform, and RNA was precipitated with ethanol. Next, the RNA precipitate was dissolved in 200 µl of 10 mM Tris-HCl (pH 7.5) containing 1 mM EDTA.

2. Synthesis of Single Stranded cDNA

To synthesize single stranded cDNA according to a procedure described by J. W. Larrick et al., Biotechnology, 7, 934 (1989), about 5 µg of the total RNA prepared as described above was dissolved in 10 µl of 50 mM Tris-HCl (pH 8.3) buffer solution containing 40 mM KCl, 6 mM MgCl$_2$, 10 mM dithiothreitol, 0.5 mM dATP, 0.5 mM dGTP, 0.5 mM dCTP, 0.5 mM dTTP, 35 µM oligo dT primer (Amersham), 48 units of RAV-2 reverse transcriptase (RAV-2: Rous associated virus 2; Amersham) and 25 units of human placenta ribonuclease inhibitor (Amersham), and the reaction mixture was incubated at 37° C. for 60 minutes and directly used for the subsequent polymerase chain reaction (PCR) method.

3. Amplification of cDNA Coding for Antibody V Region by PCR Method

The PCR method was carried out using a Thermal Cycler Model PHC-2 (Techne).

(1) Amplification of cDNA Coding for Mouse κ Light (κ L) Chain Variable Region

The primers used for the PCR method were MKV (Mouse Kappa Variable) primers represented in SEQ ID NO: 1 to 11, which hybridize with a mouse κ L chain reader sequence (S. T. Jones et al., Biotechnology, 9, 88, 1991), and an MKC (Mouse Kappa Constant) primer represented in SEQ ID NO: 12, which hybridizes with a mouse κ L chain C region (S. T. Jones et al., Biotechnology, 9, 88, 1991).

First, 100 µl of a PCR solution comprising 10 mM Tris-HCl (pH 8.3), 50-mM KCl, 0.1 mM DATP, 0.1 mM dGTP, 0.1 mM dCTP, 0.1 mM dTTP, 1.5 mM MgCl, 2.5 units of DNA polymerase Ampli Taq (Perkin Elmer Cetus), 0.25 µM of each group of MKV primer, 3 µM MKC primer and 1 µl of the reaction mixture of the single-stranded cDNA synthesis was heated at an initial temperature of 94° C. for 1.5 minutes, and then at 94° C. for 1 minute, 50° C. for 1 minute and 72° C. for 1 minute, in this order. After this temperature cycle was repeated 25 times, the reaction mixture was further incubated at 72° C. for 10 minutes.

(2) Amplification of cDNA Coding for Mouse H Chain V Region

As primers for the PCR, MHV (Mouse Heavy Variable) primers 1 to 10 represented in SEQ ID NO: 13 to 22 (S. T. Jones et al., Biotechnology, 9, 88, 1991), and an MHC (Mouse Heavy Constant) primer represented in SEQ ID NO: 23 (S. T. Jones et al., Biotechnology, 9, 88, 1991) were used. Amplification was carried out according to the same procedure as described for the amplification of the κ L chain V region gene in section 3. (1).

4. Purification and Digestion of PCR Product

The DNA fragments amplified by the PCR as described above were purified using a QIAGEN PCR product purification kit (QIAGEN Inc. US), and digested with 10 units of restriction enzyme Sal I (GIBCO BRL) in 100 mM Tris-HCl (pH 7.6) containing 10 MM MgCl$_2$ and 150 mM NaCl, at 37° C. for three hours. The digestion mixture was extracted with phenol and chloroform, and the DNA was recovered by ethanol precipitation. Next, the DNA precipitate was digested with 10 units of restriction enzyme Xma I (New England Biolabs), at 37° C. for two hours, and resulting DNA fragments were separated by agarose gel electrophoresis using low melting agarose (FMC Bio Products USA).

An agarose piece containing DNA fragments of about 450 bp in length was excised and melted at 65° C. for 5 minutes, and an equal volume of 20 mM Tris-HCl (pH 7.5) containing 2 mM EDTA and 200 mM NaCl was added thereon. The mixture was extracted with phenol and chloroform, and the DNA fragment was recovered by ethanol precipitation and dissolved in 10 µl of 10 mM Tris-HCl (pH 7.5) containing 1 mM EDTA. In this manner, a DNA fragment comprising a gene coding for a mouse κ L chain V region, and a DNA fragment comprising a gene coding for a mouse H chain V region were obtained. Both of the above DNA fragments had a Sal I cohesive end at the 5'-end thereof and an Xma I cohesive end at the 3'-end thereof.

5. Ligation and Transformation

About 0.3 µg of the Sal I-Xma I DNA fragment comprising a gene coding for a mouse κ L chain V region, prepared as described above, was ligated with about 0.1 µg of a pUC19 vector prepared by digesting plasmid pUC19 by Sal I and Xma I, in a reaction mixture comprising 50 mM Tris-HCl (pH 7.4), 10 mM MgCl$_2$, 10 mM dithiothreitol, 1 mM spermidine, 1 mM dATP, 0.1 µg/ml of bovine serum albumin and 2 units of T4 DNA ligase (New England Biolabs), at 16° C. for 16 hours.

Next, 7 µl of the above ligation mixture was added to 200 µl of competent cells of *E. coli* DH5α, and the cells were incubated for 30 minutes on ice, for one minute at 42° C., and again for one minute on ice. After adding 800 µl of SOC medium (*Mlecular Cloning: A Laboratory Manual*, Sambrook et al., Cold Spring Habor Laboratory Press, 1989), the cell suspension was incubated at 37° C. for one hour, and inoculated onto an 2xYT agar plate (*Molecular Cloning: A Laboratory Manual*, Sambrook et al., Cold Spring Habor Laboratory Press, 1989), which was then incubated at 37° C. overnight to obtain an *E. coli* transformant. The transformant was cultured in 5 ml of 2xYT medium containing 50 µg/ml ampicillin, at 37° C. overnight, and a plasmid DNA was prepared from the culture according to an alkaline method (*Molecular Cloning: A Laboratory Manual*, Sambrook et al., Cold Spring Habor Laboratory Press, 1989). The thus-obtained plasmid containing a gene coding for a mouse κ L chain V region derived from the hybridoma AUK12-20, was designated-p12-k2.

According to the same procedure as described above, a plasmid containing a gene coding for a mouse H chain V region derived from the hybridoma AUK12-20 was constructed from the Sal I-Xma I DNA fragment, and designated p12-h2.

Example 2

Cloning of DNA Coding for V Region of Mouse Monoclonal Antibody (2)

Substantially the same procedure as described in Example 1 was applied to the hybridoma PM1, AUK64-7, and AUK146-15, to obtain the following plasmids:

a plasmid pPM-k3 containing a gene coding for a κ L chain V region derived from the hybridoma PM1;

a plasmid pPM-h1 containing a gene coding for an H chain V region derived from the hybridoma PM1:

a plasmid p64-k4 containing a gene coding for a κ L chain V region derived from the hybridoma AUK64-7;

a plasmid p64-h2 containing a gene coding for an H chain V region derived from the hybridoma AUK64-7;

a plasmid p146-k3 containing a gene coding for a κ L chain V region derived from the hybridoma AUK146-15; and a plasmid p146-h1 containing a gene coding for an H chain V region derived from the hybridoma AUK146-15.

Note E. coli strains containing the above-mentioned plasmid were deposited with the National Collections of Industrial and Marine Bacteria Limited under the Budapest Treaty on Feb. 11, 1991, and were given the accession number shown in Table 8.

TABLE 8

| Plasmid | SEQ ID NO | Accession No. |
| --- | --- | --- |
| p12-k2 | 24 | NCIMB 40367 |
| p12-h2 | 26 | NCIMB 40363 |
| pPM-k3 | 28 | NCIMB 40366 |
| pPM-h1 | 30 | NCIMB 40362 |
| p64-k4 | 32 | NCIMB 40368 |
| p64-h2 | 34 | NCIMB 40364 |
| p146-k3 | 36 | NCIMB 40369 |
| p146-h1 | 38 | NCIMB 40365 |

Example 3

Sequencing of DNA

Nucleotide sequences of a cDNA coding region in the above-mentioned plasmids were determined using a kit, Sequenase(™) Version 2.0 (U.S. Biochemical Corp. USA).

First, about 3 μg of plasmid DNA obtained as described above was denatured with 0.2 N NaOH, annealed with a sequencing primer, and labeled with $^{35}$S-dATP according to a protocol of the supplier. Next, the labeled DNA was applied to 6% polyacrylamide gel containing 8 M urea, and, after electrophoresis, the gel was fixed with 10% methanol and 10% acetic acid, dried, and subjected to autoradiography to determine the nucleotide sequence.

The nucleotide sequence of cDNA coding region in each plasmid is shown in SEQ ID NOs: 24, 26, 28, 30, 32, 34, 36 and 38.

Example 4

Determination of CDRs

General structures of L chain and H chain V regions are similar each other, wherein 4 frame works (FRs) are linked through 3 super variable regions, i.e., complementarity determining regions (CDRs). While amino acid sequences in the FRs are relatively well conserved, amino acid sequences in CDRs are very highly variable (Kabat, E. A. et al., "Sequences of Proteins of Immunological Interest", US Dept. Heath and Human Services 1983).

On the basis of the above-determined amino acid sequences of V regions of mouse monoclonal antibodies to human IL-6R, and according to Kabat, E. A. et al., "Sequences of Proteins of Immunological Interest", US Dept. Health and Human Services 1983, CDRs of each V region of mouse monoclonal antibodies to the human IL-6R were determined as shown in Table 9.

TABLE 9

| plasmid | SEQ ID NO | CDR(1) | CDR(2) | CDR(3) |
| --- | --- | --- | --- | --- |
| | | (Amino acid No.) | | |
| p12-K2 | 24 | 24-38 | 54-60 | 93-101 |
| p12-h2 | 26 | 31-35 | 50-66 | 99-105 |
| pPM-k3 | 28 | 24-34 | 50-56 | 89-97 |

TABLE 9-continued

| plasmid | SEQ ID NO | CDR(1) | CDR(2) | CDR(3) |
| --- | --- | --- | --- | --- |
| | | (Amino acid No.) | | |
| pPM-h1 | 30 | 31-36 | 51-66 | 99-108 |
| p64-k4 | 32 | 24-38 | 54-60 | 93-101 |
| p64-h2 | 34 | 31-35 | 50-66 | 99-109 |
| p146-k3 | 36 | 24-34 | 50-56 | 89-97 |
| p146-h1 | 38 | 31-35 | 50-66 | 99-106 |

Example 5

Confirmation of Expression of Cloned cDNA(1) (Construction of Chimeric AUK12-20 Antibody)

Construction of Expression Plasmid

A chimeric L chain/H chain was constructed from PCR-cloned cDNAs coding for V regions κ L chain and H chain of AUK12-20. In order to easily join a cDNA coding for the mouse AUK12-20 V region to a DNA coding for a human C region in a mammalian expression vector containing an enhancer and promoter of human cytomegalovirus (HCMV) expression vector, it is necessary to introduce convenient restriction enzyme cleavage sites to the 5'- and 3'-termini of the mouse cDNA.

This modification of the 5'- and 3'-termini was carried out by PCR method. Two sets of primers were designed and synthesized. An L chain V region backward primer SEQ ID NO: 40) and H chain V region backward primer SEQ ID NO: 41) were designed so that the primers hybridize with a DNA coding for the beginning of the leader sequence, maintain a DNA sequence essential for efficient translation (Kozak, M., J. Mol. Biod. 196: 947-950, 1987) and form a HindIII site for cloning into the HCMV expression vector. An L chain V region forward primer SEQ ID NO: 42) and an H chain V region forward primer SEQ ID NO: 43) were designed so that the primers hybridize with a DNA coding for the terminal portion of the J region, maintain a DNA sequence essential for splicing into the C region and form a Bam HI site for joining to the human C region in the HCMV expression vector.

Following the amplification by the PCR, the PCR product was digested with Hind III and BamHI, cloned into the HCMV vector containing the human κ and γ1 chain C regions DNA and sequenced to confirm that errors were not introduced during the PCR amplification. The resulting expression vectors are designated as HCMV-12k-gk and HCMV-12h-gγ1.

The structures of the HCMV expression plasmids are shown in FIG. 1. In the plasmid HCMV-$V_L$-HC$_K$, $V_L$ region may be any mouse L chain V region. In this example, AUK12-20 κL chain V region was inserted to obtain the HCMV-12k. In the plasmid HCMV-$V_H$-HCγ1, $V_H$ region may be any mouse H chain V region. In this example, AUK12-20 H chain V region was inserted to obtain HCMV-12h-gγ1.

Transient Expression in COS Cells

To observe transient expression of a chimeric AUK12-20 antibody in COS cells, the expression vectors constructed as described above were tested in the COS cells. The vector DNAs were introduced into COS cells by electroporation using a Gene Pulsar apparatus (Bio Rad). Namely, COS cells were suspended in phosphate-buffered saline (PBS) to a cell concentration of 1×10$^7$ cells/ml, and to 0.8 ml aliquot of the suspension was added 10 μg (per each plasmid) of DNA. Pulses were applied at 1,900 V and 25 μF.

After recovery period of 10 minutes at a room temperature, the electroporated cells were added to 8 ml of DMEM (GIBCO) containing 10% fetal bovine serum. After incubation for 72 hours, a culture supernatant is collected, centrifuged to eliminate cell debris, and aseptically stored for a short period at 4° C. or for a long period at −20° C.

Quantification of Chimeric Antibody by ELISA

A culture supernatant of the transfected COS cells was assayed by ELISA to confirm the production of chimeric antibody. To detect the chimeric antibody, a plate was coated with goat anti-human IgG whole molecule (Sigma). The plate was blocked, and serially diluted supernatant from the COS cell culture was added to each well. After incubation and washing, alkaline phosphatase-linked goat anti-human IgG (γ-chain specific, Sigma) was added to each well. After incubation and washing, substrate buffer was added thereon. The reaction mixture was incubated, and after termination of the reaction, optical density at 405 mm was measured. As a standard, purified human IgG (Sigma) was used.

ELISA for Confirmation of an Ability to Bind to Human IL-6R

A culture supernatant of the transformed COS cells was assayed by ELISA to determine whether the produced antibody can bind to the antigen. To detect the binding to the antigen, a plate was coated with MT18 mouse monoclonal antibody (Reference Example 1), and after blocking with 1% bovine serum albumin (BSA) soluble recombinant human IL-6R(SR 344) was added thereon. After washing, a serially diluted culture supernatant from the COS cells was added to each well. After incubation and washing alkaline phosphatase-linked goat anti-human IgG was added. The reaction mixture was incubated, and after washing a substrate buffer was added. After incubation, the reaction was terminated, and optical density at 405 mm was measured.

Figure 2:
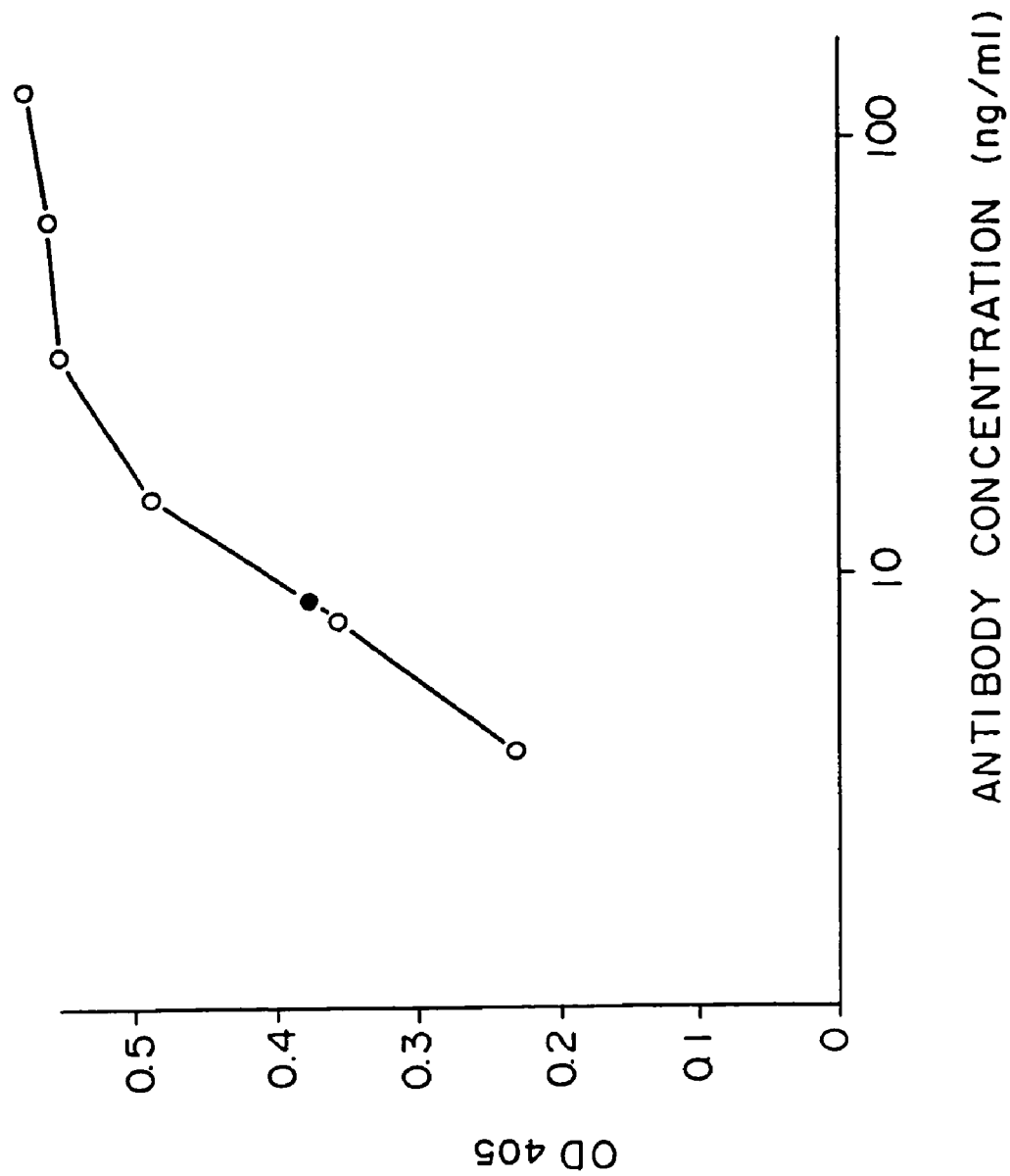
FIG. 2 is a graph showing a result of ELISA for confirmation of an ability of the present chimeric antibody AUK12-20 to bind to the human IL-6R.

A result is shown in FIG. 2. Transfection of gene coding for a chimeric antibody AUK12-20 into COS cells was twice repeated. Both the culture supernatant samples exhibited a strong binding to IL-6R, and optical density at 405 mm was changed in a sample dilution (monaclonal antibody concentration)—dependent manner as shown in FIG. 2 by open circles and closed circles revealing the presence of an antibody to IL-6R in the sample.

Determination of an Ability to Inhibit the Binding to IL-6R with IL-6

To determine whether an antibody present in a medium inhibits the binding of IL-6R with IL-6, a plate was coated with MT18 monoclonal antibody (Reference Example 1). After blocking, soluble recombinant human IL-6R(SR 344) was added thereon. After washing, serially diluted sample from COS cell culture was added to each well with biotinated IL-6.

After washing, alkaline phosphatase-linked streptoavidin was added, and after incubation and washing, a substrate buffer was added. The reaction mixture was incubated, and after termination of the reaction, optical density at 405 mm was measured, purified mouse AUK12-20 monoclonal antibody was added as a positive control, and a culture medium from COS cells expressing a non-related antibody was used as a negative control.

Figure 3:
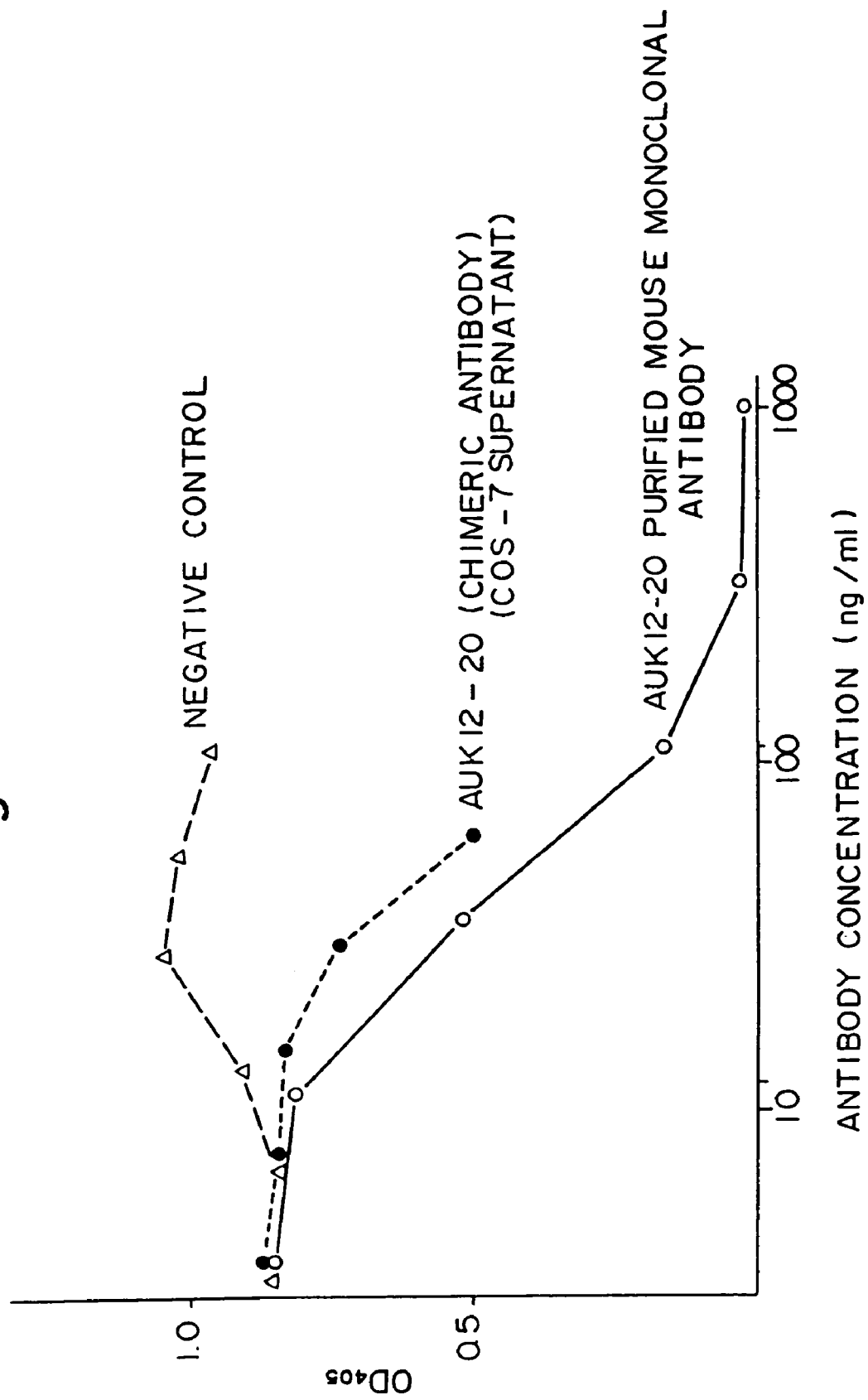
FIG. 3 is a graph showing a result of measurement of an ability of the present chimeric antibody AUK12-20 to inhibit the binding of IL-6 to the human IL-6R.

A result is shown in FIG. 3. A culture supernatant of COS cells transfected with genes coding for chimeric antibody AUK 12-20 exhibited the binding of IL-6R with IL-6 at the highest and second highest concentrations. Namely, as shown by closed circles in FIG. 3, optical density at 405 mm changed in a sample dilution (antibody concentration) dependent manner, revealing the inhibition of the binding to IL-6R with IL-6 by an antibody in the sample. This is further confirmed by substantive conformity with antibody concentration dependent change of the positive control (open circles). Note, the negative control did not exhibit inhibition activity (open triangles).

Example 6

Confirmation of Expression of Cloned cDNA (2)
(Construction of Chimeric PM-1 Antibody)

(Construction of Expression Vectors)

In order to construct vectors expressing chimeric PM-1antibody, the cDNA clones pPM-k3 and pPM-h1, coding for the mouse PM-1 κL chain and the H chain V regions, respectively, were modified by a PCR technique, and then introduced into the HCMV expression vectors (see FIG. 1). The backward primers pmk-s (SEQ ID NO: 45) for L chain V region and pmh-s (SEQ ID NO: 47) for H chain V region were designed to hybridize to the DNA sequences coding for the beginning of the leader sequences, and to have Kozak consensus sequence and a HindIII restriction site. The forward primers pmk-a (SEQ ID NO: 44) for L chain V region and pmh-a (SEQ ID NO: 46) for H chain V region were designed to hybridize to the DNA sequences coding for the ends of the J regions, and to have a splice donor sequence and a BamHI restriction site.

For the kappa L chain V region, two forward primers were synthesized. Although in most kappa L chains lysine at position 107 is conserved, in mouse PM-1 kappa L chain position 107 is an asparagine. In order to investigate the effect of this change on the antigen-binding activity of the chimeric PM-1 antibody, the forward primer pmk-b (SEQ ID NO: 42) was designed to mutate position 107 from an asparagine to a lysine. Following the PCR reaction, the PCR products were purified, digested with HindIII and BamHI, and subcloned into a pUC19 vector (Yanishe-Perron et al., Gene (1985) 33:103-109). After DNA sequencing, the HindIII-BamHI fragments were excised and cloned into the expression vector HCMV-$V_H$-HC$_\gamma$ to obtain HCMV-pmh-gγ for the chimeric H chain, and into the expression vector HCMV-$V_L$-HC$_k$ to obtain HCMV-pmka-gk and HCMV-pmkb-gk for the chimeric L chain.

Transfection of COS Cells

The vectors were tested in cos cells to look for transient expression of chimeric human PM-1 antibodies. The HCMV-pmh-gγl, and either HCMV-pmka-gk or HCMV-pmkb-gk were co-transfected into the cos cells by electroporation using the Gene Pulsar apparatus (BioRad). DNA (10 μg of each plasmid) was added to a 0.8 ml aliquot of 1×10$^7$ cells/ml in PBS. A pulse was delivered at 1,900 volts, 25 microfarads capacitance. After a 10 min recovery period at a room temperature, the electroporated cells were added to 20 ml of Dulbecco's Modified Eagle Medium (DMEM) (GIBCO) containing 10% gamma-globulin-free fetal calf serum. After 72 h incubation, the medium was collected, centrifuged to remove cellular debris, and stored under sterile conditions at 4° C. for short periods of time, or at −20° C. for longer periods.

Expression and Analysis of the Chimeric PM-1 Antibodies

After 3 days of transient expression, medium from the cos cells was collected and tested for chimeric PM-1 antibody. The medium was first analyzed by ELISA to determine if human-like antibody was being produced by the transfected cos cells. By using known amounts of purified human IgG as a standard in this assay, it is also possible to estimate an amount of human-like antibody (in this case, chimeric PM-1 antibody) present in the medium from the cos cells. For the detection of human antibody, plates were coated with goat anti-human IgG (whole molecule, Sigma). Following blocking, the samples from cos cells were serially diluted and added to each well. After incubation and washing, alkaline phosphatase-conjugated goat anti-human IgG (gamma chain specific, Sigma) was added. After incubation and washing, substrate buffer was added. After incubation, the reaction was stopped and the optical density at 405 nm measured. Purified human IgG (Sigma) was used as a standard.

The medium from the cos cells transfected with the vectors carrying the chimeric PM-1 genes was positive for the expression of a human-like antibody and the approximate amounts were quantified as described.

Next, the same medium from the cos cells transfected with the vectors carrying the chimeric PM-1 genes was assayed for a an ability to bind to human IL-6R. For the detection of binding to the antigen, plates were coated with MT18 mouse monoclonal anitbody (Reference Example 1), an antibody to the human IL-6R. Following blocking, soluble recombinant human IL-6R(SR344) was added. After washing, the samples were serially diluted and added to each well. After incubation and washing, alkaline phosphatase-conjugated goat anti-human IgG (gamma chain specific sigma) was added. After incubation and washing, substrate buffer was added. After incubation, the reaction was stopped and the optical density at 405 nm measured. There was no standard available for this assay.

Two samples were from transfection with genes coding for a chimeric antibody with V regions identical to those found in mouse PM-1 antibody (chimeric PM-1a antibody, FIG. 4). One sample was from transfection with genes coding for a chimeric antibody with a single amino acid change at position 107 in the L chain V region as described above (chimeric PM-1b antibody, FIG. 4). All samples showed strong binding to IL-6R that decreased with dilution of the sample. Thus, the chimeric PM-1 antibody, as constructed, is functional and can bind well to its antigen. Most importantly, the demonstration of a functional chimeric PM-1 is direct evidence that the correct mouse PM-1 V regions have been cloned and sequenced. The chimeric PM-1 antibody, with either amino acid at position 107 in the L chain V region, bound well to its antigen, IL-6R. It appears that position 107 in the mouse PM-1 L chain V region is not very critical in antigen-binding and that either an asparagine or a lysine at this position will function satisfactorily. Since the mouse PM-1 antibody has an asparagine at this position in its L chain V region, all future work with chimeric PM-1 antibody was done with version a, the version that has V regions identical to those found in mouse PM-1 antibody.

In order to stably produce larger amounts of chimeric PM-1 antibody, a new HCMV expression vector incorporating the dhfr gene was constructed. The first step in achieving higher levels of expression of the chimeric PM-1 antibody was to modify the vector HCMV-$V_H$-$HC_{\gamma l}$ (FIG. 1) so that this vector contained a dhfr gene being expressed by a "crippled" SV40 promoter-enhancer. The SV40 enhancer elements were deleted from the pSV2-dhfr vector (S. Subramani et al., Mol. Cell. Biol. (1981) 1:854-864) and the dhfr gene being expressed by the "crippled" SV40 promoter was inserted into the HCMV-$V_H$-$HC_{\gamma l}$ vector in place of the neo gene being expressed by the SV40 promoter-enhancer. The mouse PM-1 V region was then inserted into this new HCMV-$V_H$-$HC_{\gamma l}$-dhfr vector. Construction of the improved expression vector is described in Example 10 in detail.

CHO dhfr(-) cells (G. Urlaub et al., Proc. Natl. Acad. Sci. USA (1980) 77:4216-4220) were co-transfected with two plasmid DNAs, the HCMV-$V_L$-$HC_\kappa$ vector for expressing chimeric PM-1a L chain (HCMV-pmka-gk) and the HCMV-$V_H$-$HC_{\gamma l}$-dhfr vector for expressing chimeric PM-1 H chain (DHFR-ΔE PMh-gγl; Example 10). DNA (10 μg of each plasmid) was added to a 0.8 ml aliquot of $1 \times 10^7$ cells/ml in PBS. A pulse was delivered at 1900 volts, 25 microfarads capacitance. After a 10 min recovery period at a room temperature, the electroporated cells were added to 10 ml of Alpha minimum essential medium (α-MEM) containing nucleosides and 10% FCS. After overnight incubation, the medium was changed to α-MEM without nucleosides and with 10% FCS and 500 μg/ml of G418 (GIBCO) for the selection of dhfr+ and neo+ transformed cells. After selection, the selected clones were used for gene amplification. After one round of amplification in $2 \times 10^{-8}$ M methotrexate (MTX), a cell line (PM1k3-7) was selected that produced approximately 3.9 μg/$10^6$ cells/day of chimeric PM-1a antibody.

ELISA Assay for the Ability of Chimeric Antibodies to Inhibit IL-6 from Binding to Human IL-6R.

Figure 5:
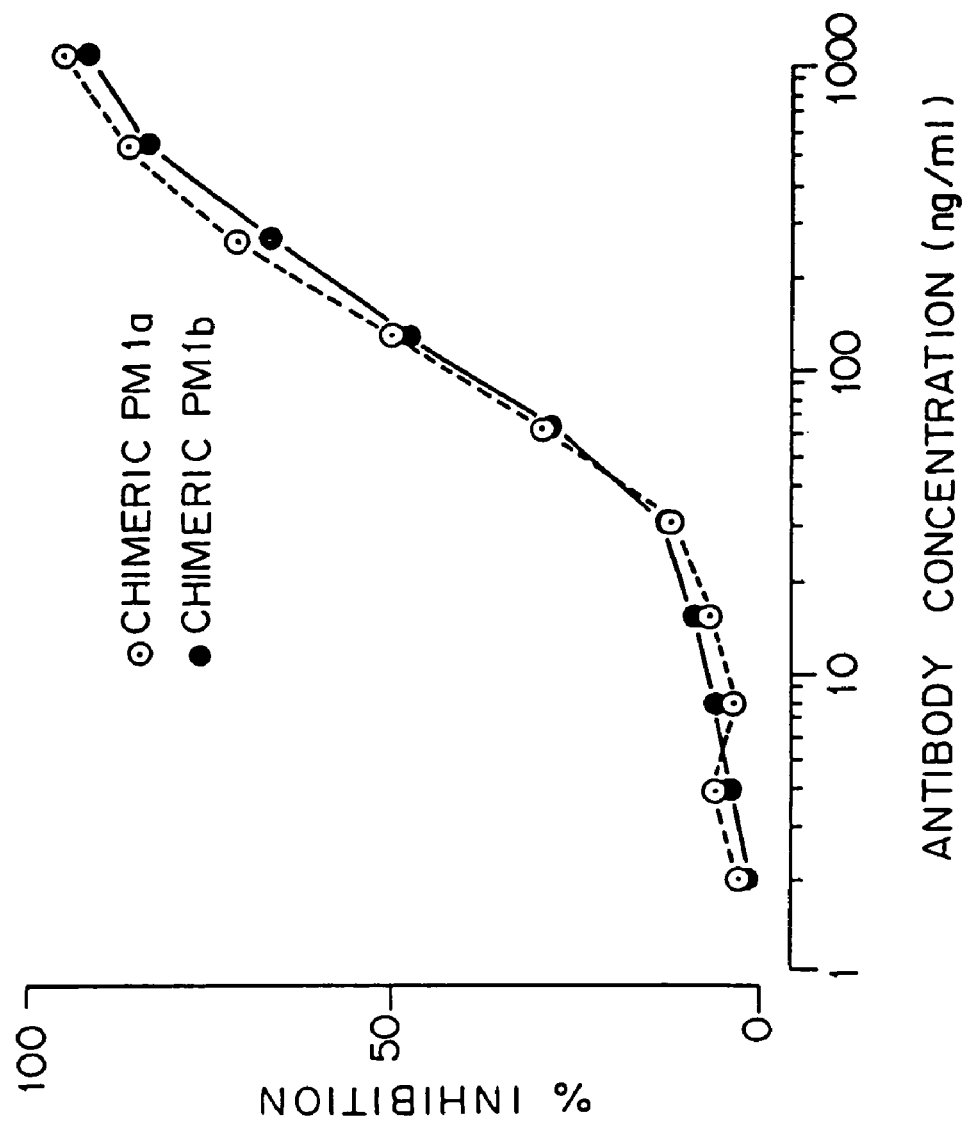
FIG. 5 is a graph showing a result of ELISA testing the ability of the present chimeric antibodies PM1a and PM1b to inhibit IL-6 from binding to the human IL-6R.

Antibodies produced in transfected cos cells or in stable CHO cell lines were assayed to determine whether the antibodies could compete with biotinylated IL-6 for binding to IL-6R. Plates were coated with MT18 mouse monoclonal antibody. Following blocking, soluble recombinant human IL-6R(SR344) was added. After washing, the samples from the cos cells were serially diluted and added together with biotinylated IL-6 to each well. After washing, alkaline phosphatase-conjugated streptavidin was added. After incubation and washing, substrate buffer was added. After incubation, the reaction was stopped and the optical density at 405 nm measured. The Results are shown in FIG. 5.

Example 7

Construction of Reshaped Human PM-1 Antibodies

In order to achieve CDR-grafting more rapidly and efficiently, a method for sequential CDR-grafting by PCR was developed. This method is based on PCR-mutagenesis methods (Kamman et al., 1989).

In order to prepare the template DNAs containing the selected human FRs for CDR-grafting, it was necessary to reclone suitable reshaped human V regions into convenient vectors. Plasmid DNAs alysll and F10 code for reshaped human D1.3 L and H chains and contain the FRs from human REI and NEW, respectively. An approximately 500 bp NcoI-BamHI fragment containing DNA sequence coding for the reshaped human D1.3 L chain V region was excised from alysll and subcloned into HindIII-BamHI cleaved-pBR327 to obtain a vector V1-lys-pBR327. HindIII-BamHI fragment from the V1-lys-pBR327 was inserted into HindIII-BamHI cleaved pUC19 to obtain a vector V1-lys-pUC19. An approximately 700 bp NcoI-BamHI fragment containing DNA sequence coding for the reshaped human D1.3 H chain V region was excised from F10 and subcloned into the HindIII-BamHI site of pBR327 vector, using a HindIII-NcoI adaptor, yielding Vh-lys-pBR327. A HindIII-BamHI fragment was then excised from this vector and subcloned into HindIII-BamHI cleaved pUC19 vector yielding Vh-lys-pUC19.

Note the construction of the plasmid alysll and the DNA sequence coding for the reshaped human D1.3 L chain V region used in a template is described. The DNA sequence coding for the reshaped human D1.3 H chain V region in the plasmid F10 used as a template is described in V. Verhoey et al., Science 237:1534-1536 (1988) FIG. 2.

FIG. 6 diagrams the primers and the PCR reactions used in the construction of the first version of reshaped human PM-1

H chain V region. A backward primer A (APCR1; SEQ ID NO: 48) and a forward primer E (APCR4; SEQ ID NO: 49) hybridize to DNA sequences on the vector. Although APCR1 and APCR4 were specifically designed for pUC19 vector, universal M13 sequence primers could be used.

The CDR1-grafting/mutagenic primer B (phv-1; SEQ ID NO: 50), CDR2-grafting primer C (phv-2; SEQ ID NO: 51) and CDR3-grafting primer D (phv-3; USEQ ID NO: 52) were 40-60 bp in length, consisting of DNA sequences coding for CDRs from the mouse PM-1 H chain V region and the human FRs in the template DNA that flank the CDR regions. In the first PCR reaction, the forward primer APCR4 and the backward primer D were used. The first PCR product, which contains the mouse PM-1 CDR3 sequence, was purified and used in the second PCR reaction as a forward primer with primer C as the backward primer. In the same manner, the second and third PCR products, which contain mouse PM-1 CDR2 and CDR3, and all three mouse PM-1 CDRs, respectively, were used as primers in the following PCR step. The fourth PCR product, which has the complete reshaped human PM-1 H chain V region, was purified, digested with HindIII and BamHI, and subcloned into a pUC19 vector for further analysis.

Three mutagenic primers phv-1, phv-2, and phv-3 were synthesized for the construction of reshaped human PM-1 H chain V region. They were purified on 12% polyacrylamide gels containing 8M urea. The mutagenic primer phv-1 was designed not only for mouse PM-1 CDR1-grafting but also for mutations at positions 27 and 30 in human FR1, Ser to Tyr and Ser to Thr, respectively. Each 100 µl PCR reaction typically contained 10 mM Tris-HCl (pH 8.3), 50 mM KCl, 1.5 mM $MgCl_2$, 250 µM dNTPs, 50 ng of the template DNA (Vh-lys-pUC19), 2.5 u of AmpliTaq (Perkin Elmer Cetus) and the primers. The first PCR reaction containing 1 µM of each of the phv-3 and APCR4 primers was carried out, after an initial denaturation at 94° C. for 1.5 min, for 30 cycles of 94° C. for 1 min, 37° C. for 1 min and 72° C. for 1 min were repeated. The ramp time between the annealing and synthesis steps was set for 2.5 min. The completion of the last cycle was followed by a final extension at 72° C. for 10 min. A 523 bp PCR product was purified using a 1.6% low melting temperature agarose gel and then used as a primer in the second PCR reaction.

In the second PCR reaction approximately 1 µg of the purified first PCR product and 25 pmoles of the mutagenic primer phv-2 were used as primers. The PCR conditions were the same as described for the first PCR reaction. In the same manner, a 665 bp PCR product from the second PCR reaction and a 737 bp PCR product from the third reaction were used as primers in the third PCR reaction with the primer phv-1, and in the fourth PCR reaction with the primer APCR1, respectively. A 1.172 kb PCR product from the fourth PCR reaction was purified, digested with HindIII and BamHI, and then an approximately 700 bp fragment containing the reshaped human PM-1 H chain V region was subcloned into a pUC19 vector. Two of four clones sequenced had the DNA sequence coding for the correct amino acid sequence and were designated pUC-RVh-PM1a.

In order to construct other versions of reshaped PM-1 H chain V region, five mutagenic PCR primers were synthesized. Each PCR reaction was essentially carried out under the same condition as described above. For version "b", mutagenic primer phv-m4 (Val-71 to Arg-71; the number is according to Kabat et al; see Table 3) (SEQ ID NO: 53) and APCR4 were used in the first PCR reaction with template DNA, pUC-RVh-PM1a. The PCR product from this first PCR reaction was purified and was used as a forward primer in the second PCR reaction with the primer APCR1. The PCR product from the second PCR reaction was purified using a 1.6% low melting temperature agarose gel, digested with HindIII and BamHI, and subcloned into a pUC19 vector yielding pUC-RVh-PM1b. In the same manner, version "c" (pUC-RVh-PM1c) was obtained using a mutagenic primer phv-nm (Asp-1 to Gln-1) (SEQ ID NO: 54) and a template pUC-RVh-PM1b; version "d" (pUC-RVh-PM1d) was obtained using a mutagenic primer phv-m6 (Ile-48 to Met-48) (SEQ ID NO: 55) and a template pUC-RVh-PM1b; version "e" (pUC-RVh-PM1e) was obtained using the mutagenic primer phv-m6 and a template pVC-RVh-PM1c; and "version f" (pUC-RVh-PM1f) was obtained using a mutagenic primer phv-m7 (Thr-28 to Ser-28, and Phe-29 to Ile-29) (SEQ ID NO: 56) and a template pUC-RVh-PM1b. Amino acid sequence of the version "f" of the reshaped human H chain V region, and a nucleotide sequence codin therefor is shown in SEQ ID NO: 61.

Figure 7:
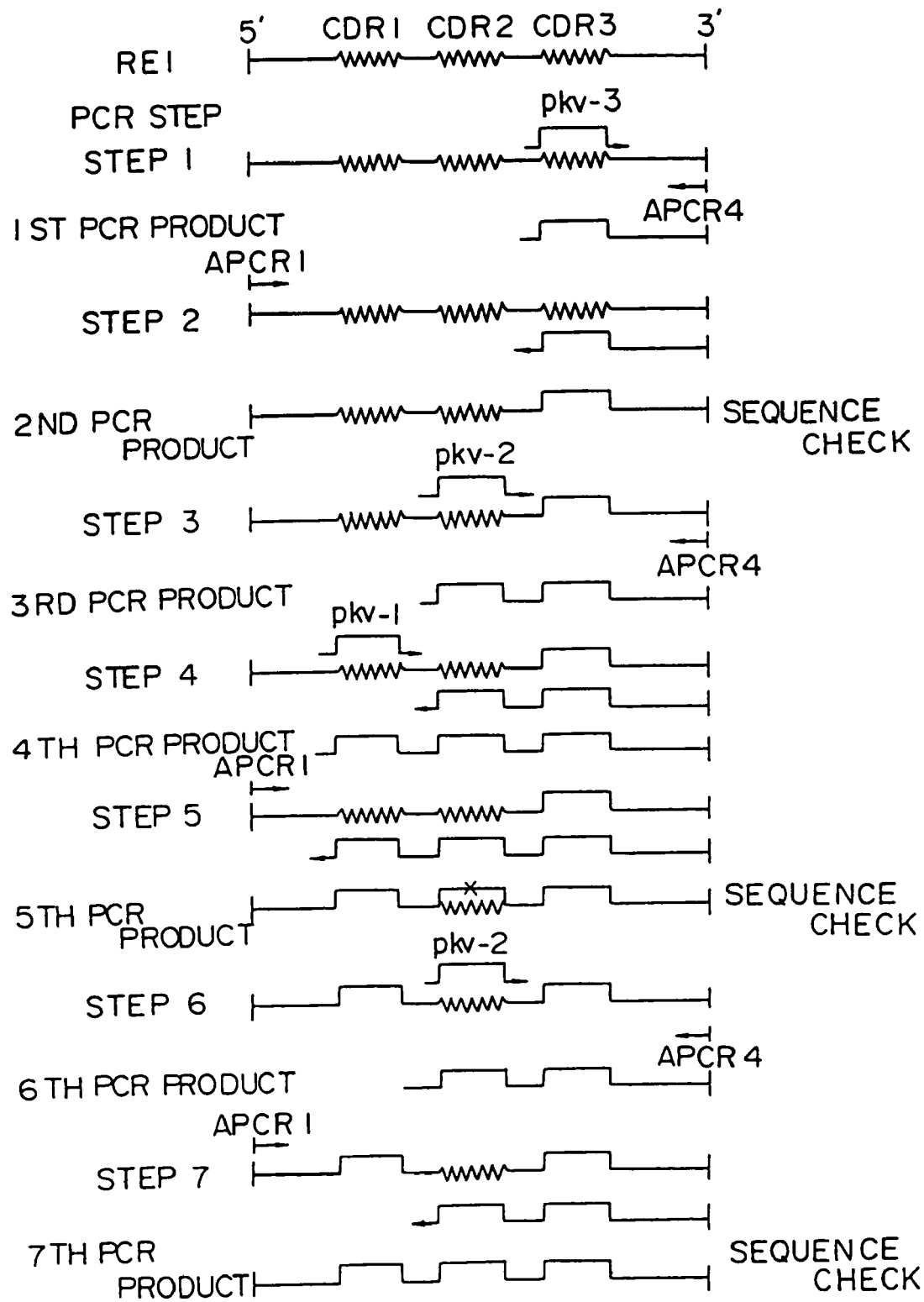
FIG. 7 is a diagram of the construction of the first version of a reshaped human PM-1 L chain V region.

FIG. 7 diagrams the primers and the PCR reactions used in the construction of the first version of reshaped human PM-1 L chain V region. For the construction of the first version of reshaped human PM-1 L chain V region, CDR1-grafting primer pkv-1 (SEQ ID NO: 57), CDR2-grafting primer pkv-2 (SEQ ID NO: 58) and CDR3-grafting primer pkv-3 (SEQ ID NO: 59) were synthesized and purified on a 12% polyacrylamide gel containing 8M urea. PCR reactions were carried out as described above. The first PCR reaction contained 1 µM of each of the pkv-3 and APCR4 primers. A 350 bp PCR product from the first PCR reaction was purified using a 1.5% low melting temperature agarose gel and used as a forward primer in the second PCR reaction. The PCR product from the second PCR reaction was purified, digested with BamHI and HindIII, and the 500 bp fragment containing the CDR3-grafted DNA was subcloned into a pUC19 vector for DNA sequencing. A plasmid DNA having the correct sequence was identified and used as the template DNA in the following PCR reaction. In the third PCR reaction, 25 pmoles of mutagenic primers pkv-2 and APCR4 were used. The PCR product from the third PCR reaction was purified and used as a primer, with the primer pkv-1, in the fourth PCR reaction. In the same manner, the PCR product from the fourth PCR reaction was used as a primer, with the APCR1 primer, in the fifth PCR reaction.

A 972 bp PCR product from the fifth PCR reaction was purified, digested with BamHI and HindIII, and subcloned into a pUC19 vector for DNA sequencing. A problem was identified in the CDR2 region. Two additional PCR reactions were necessary. In the sixth and seventh PCR reactions, the PCR product from the fifth PCR reaction, as cloned into pUC19 vector, was used as template DNA. In the sixth PCR reaction, the primers were pkv-2 and APCR4. The PCR product from the sixth PCR reaction was purified and used as a primer, with the APCR1 primer, in the seventh PCR reaction. The PCR product of the seventh PCR reaction was purified, digested with BamHI and HindIII, and a 500 bp DNA fragment was subcloned into a pUC19 vector for DNA sequencing. Two of five clones sequenced had the correct DNA sequence. The clone was designated pUC-RV1-PM1a. The sequence is shown in SEQ ID NO: 63.

For the construction of the other version of reshaped human PM-1 L chain V region, a mutagenic primer pvk-m1 (SEQ ID NO: 60) was synthesized. The PCR reactions were essentially as described above. In the first PCR reaction, the mutagenic primer pkv-m1 (Phe-71 to Tyr-71) and the APCR4 primer were used with the template DNA pUC-RV1-PM1a. The PCR product of the first PCR reaction was purified and used as a primer, with the APCR1 primer, in the second PCR reaction. The PCR product of the second PCR reaction was purified, digested with BamHI and HindIII, and subcloned into a pUC19 vector for DNA sequencing. The clone was designated pUC-RV1-PM1b.

Example 8

Construction of Vectors that Employ the Human Cytomegalovirus Immediate Early (HCMV) Promoter to Express Genetically-Engineered Antibodies in Mammalian Cells (FIG. 1).

The DNA fragments coding for the chimeric PM-1 L and H chain V regions were initially inserted into HCMV vectors (HCMV-V$_L$-HC$_K$ and HCMV-V$_H$-HCγ1) designed to express either human kappa L chains or human gamma-1 H chains in mammalian cells (see FIG. 1). A detailed description of the construction of the HCMV expression vectors is published in Maeda et al., Human Antibodies and Hybridomas (1991) 2:124-134; C. A. Kettleborough et al., Protein Engeneering (1991) 4:773-783. Both vectors are based on pSV2neo (P. J. Southern et al., J. Mol. Appln. Genet. (1982) 1:327-341) and contain the human cytomegalovirus (HCMV) promoter and enhancer (M. Boshart et al., Cell (1985) 41:521-530) for high level transcription of the immunoglobulin L and H chains. The L chain expression vector contains genomic DNA coding for the human kappa C region (T. H. Rabbitts et al., Curr. Top. Microbiol. Immunol. (1984) 113:166-171) and the H chain expression vector contains genomic DNA coding for the human gamma-1 C region (N. Takahashi et al. Cell (1982) 29:671-679). The HCMV expression vectors are versatile and can be used for both transient and stable expression in a variety of mammalian cell types.

Example 9

Figure 8:
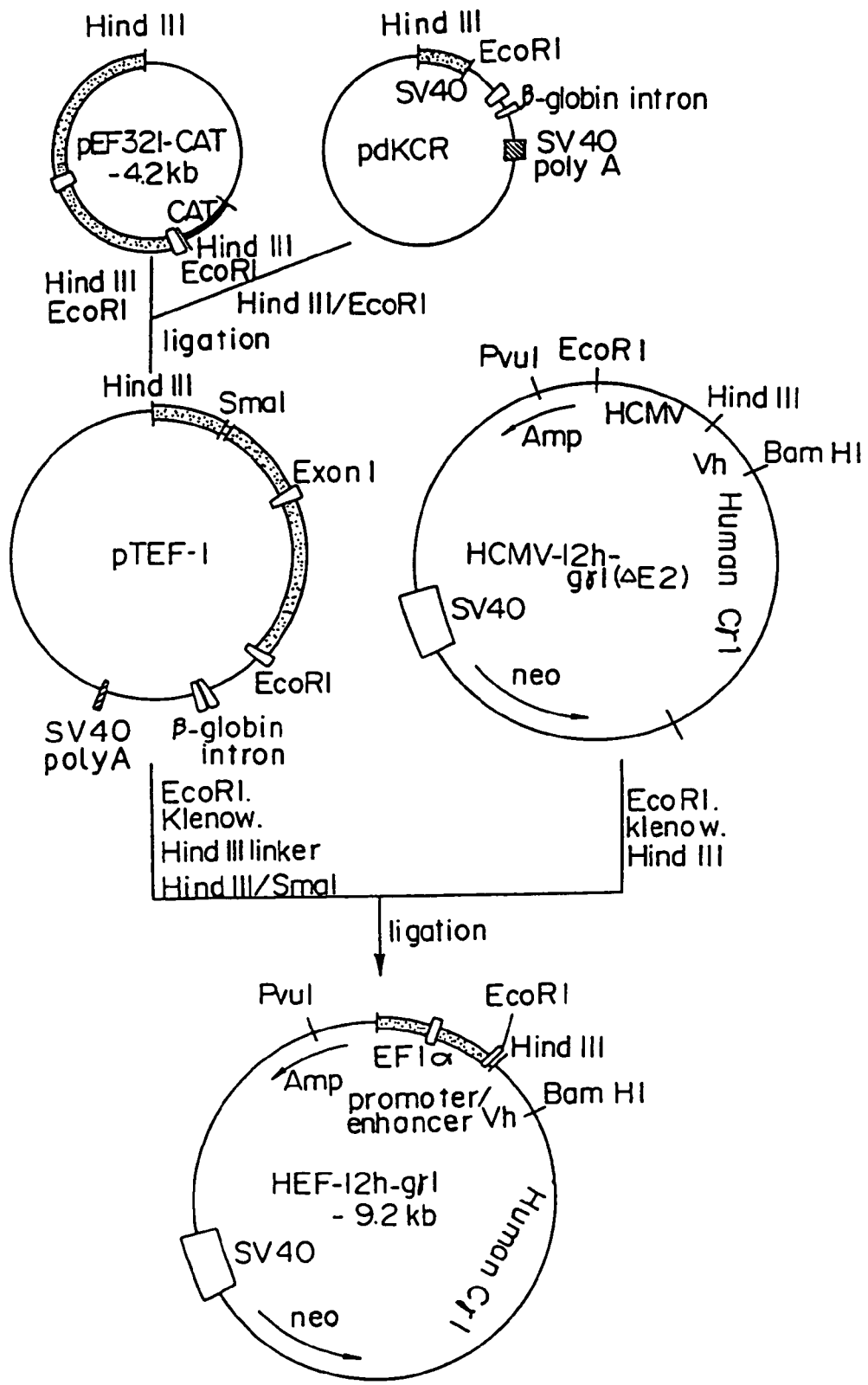
FIG. 8 represents a process for construction of an expression plasmid HEF-12h-gγ1 comprising a human elongation factor 1α (HEF-1α) promoter/enhancer, useful for the expression of an H chain.
Figure 9:
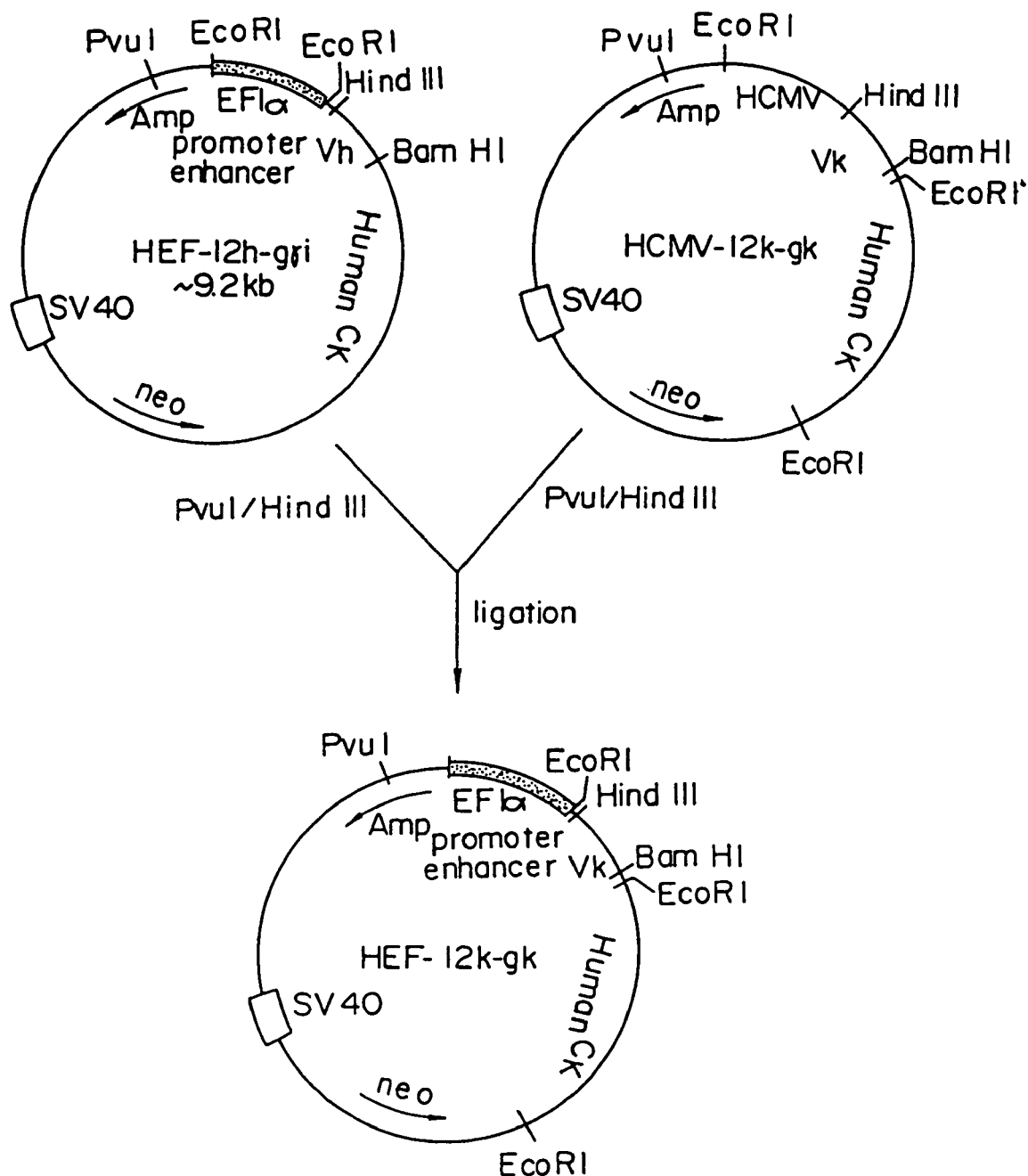
FIG. 9 represents a process for construction of an expression plasmid HEF-12k-gk comprising the HEF-1α promoter/enhancer system, useful for the expression of an L chain.

Construction of Vectors that Employ the Human Elongation Factor 1α (HEF-1α) Promoter to Express Genetically-Engineered Antibodies in Mammalian Cells (FIG. 8 and FIG. 9)

The human polypeptide chain elongation factor 1α (HEF-1α) is one of the most abundant proteins. It is expressed in most cells. The transcriptional activity of the human EF-1α promoter-enhancer is about 100-fold stronger than that of the SV40 early promoter-enhancer (D. W. Kim et al., Gene (1990) 91:217-223, and T. Uetsuki et al., J. Biol. Chem. (1989) 264:5791-5798). The 2.5 kb HEF-1α promoter-enhancer region consists of approximately 1.5 kb of DNA flanking the 5'-end of the gene, 33 bp in the first exon, 943 bp in the first intron, and 10 bp of the first part of the 2nd exon. The approximately 2.5 kb HindIII-EcoRI fragment was excised from plasmid DNA pEF321-CAT (D. W. Kim et al., Gene (1990) 91:217-223, and T. Uetsuki et al., J. Biol. Chem. (1989) 264:5791-5798) and cloned into pdKCR vector DNA (M. Tsuchiya et al., EMBO J. (1987) 6:611-616) (K. O'Hare et al., Proc. Natl. Acod. Sci USA Vol. 78, No. 3, 1527-1531, 1981) to replace an approximately 300 bp HindIII-EcoRI fragment containing the SV40 early promoter-enhancer sequence thus yielding pTEF-1. pTEF-1 was digested with EcoRI, filled-in with the Klenow polymerase, and ligated to HindIII linkers. An approximately 1.6 kb HindIII-SmaI fragment was then excised from the modified pTEF-1 vector DNA.

Plasmid DNA HCMV-12h-gγ1 (ΔE2) was constructed from the HCMV-12h-gγ1 constructed in Example 5 by partially digesting HCMV-12h-gγ1 with EcoRI, filling-in with klenow polymerase, and self-ligating.

The plasmid HCMV-12h-gγ1 (ΔE2) was digested with EcoRI, filled-in with Klenow polymerase, and digested with HindIII. The resulting approximately 7 kb fragment containing the DNA sequence coding for human gamma-1 C region was ligated to the above-prepared 1.6 kb HindIII-SmaI fragment containing the HEF-1α promoter-enhancer yielding HEF-12h-gγ1. The HEF-1α promoter-enhancer region in this vector was the same as that in pTEF-1 except for 380 bp of DNA flanking the 5'-region. The H chain V region, present as a HindIII-BamHI fragment, was easily interchangeable with other H chain V regions.

HindIII-BamHI DNA fragments containing the reshaped H chain V region were excised from the pUC-RVh-PM1a, pUC-RVh-PM1b, pUC-Rvh-PM1c, pUC-RVh-PM1d, pUC-RVh-PM1e, and pUC-RVh-PM1f (Example 7), and inserted into the HindIII-BamHI portion of the HEF-12h-gγ1 to obtain expression vectors RVh-PM1a, RVh-PM1b, RVh-PM1c, RVh-PM1d, RVh-PM1e and RVh-PMhf, respectively. The expression vectors RVh-PM1a, RVh-PM1b, RVh-PM1c, RVh-PM1d, RVh-PM1e and RVh-PM1f, as well as HEF-PMh-gγ1 have the reshaped human PM-1 H chain V regions versions "a", "b", "c", "d", "e" and "f", as well as the mouse PM-1 H chain V region, respectively.

To construct the L chain expression vector, HEF-12k-gk, an approximately 3.0 kb PvuI-HindIII fragment containing the HEF-1α promoter-enhancer region was excised from the HEF-12h-gγ1 and ligated to an approximately 7.7 kb PvuI-HindIII fragment from the HCMV L chain expression vector HCMV-12k-gk constructed in Example 5 to obtain HEF-12k-gk. As for the H chain expression vector HEF-12h-gγ1, the L chain V region in HEF-12k-gk, present as a HindIII-BamHI fragment, is easily interchangeable with other L chain V regions.

HindIII-BamHI DNA fragments containing the reshaped human L chain V region were excised from the pUC-RV1-PM1a and pUC-RV1-PM1b (Example 7), and inserted into the HindIII-BamHI portion of the HEF-12k-gk to obtain expression vectors RV1-PM1a and RV1-PM1b, respectively. The expression vectors RV1-PM1a, RV1-PM1b, and HEF-PMk-gk have the reshaped human L chain V regions "a", "b", and the mouse PM-1 L chain V region, respectively.

Example 10

Figure 10:
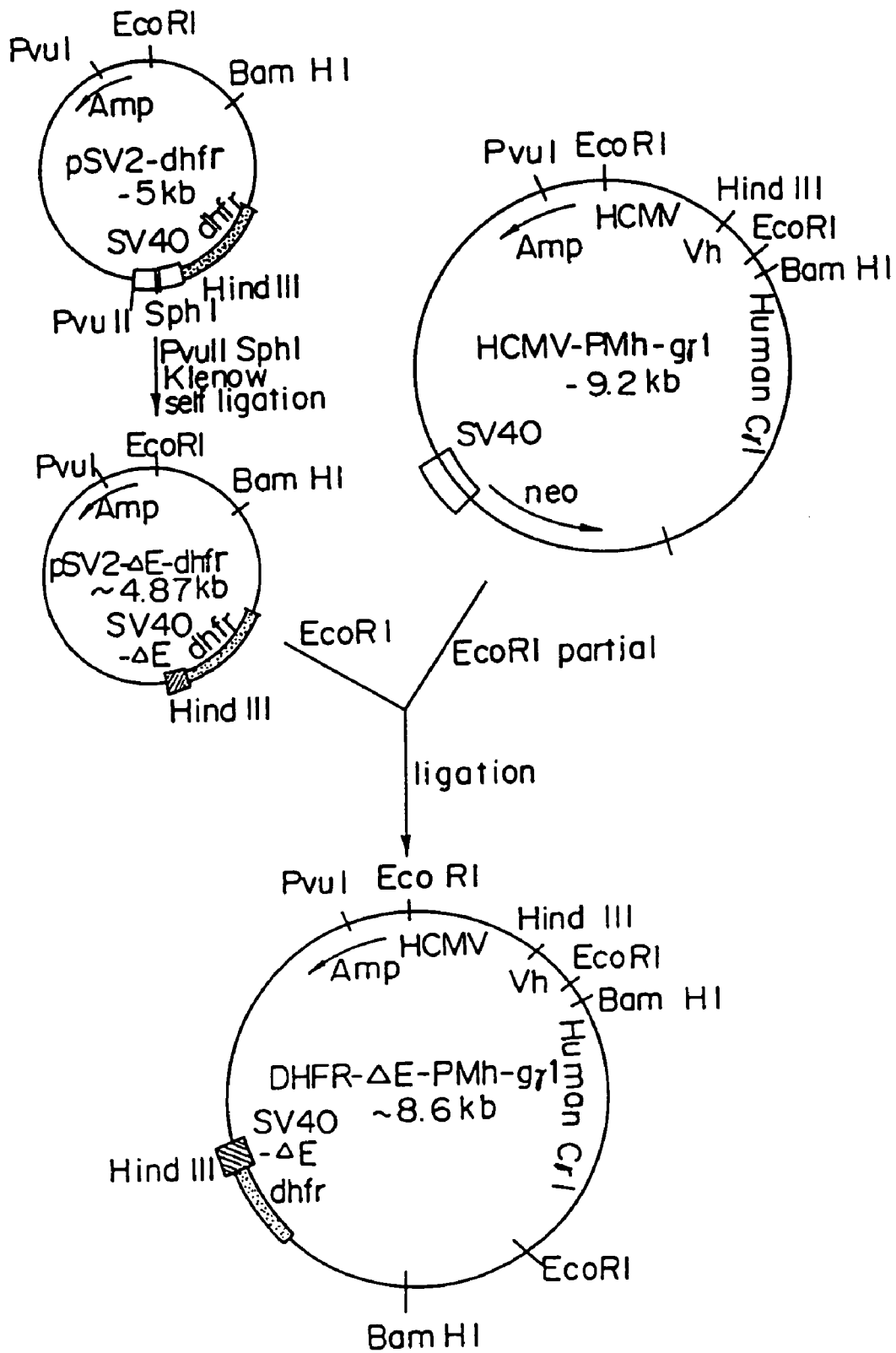
FIG. 10 represents a process for construction of an expression plasmid DHFR-PMh-gγ1 comprising HCMV promoter/enhancer and the dihydrofolate reductase (dhfr) gene linked to a defective SV40 promoter/enhancer sequence for amplification, useful for expression of an H chain.
Figure 11:
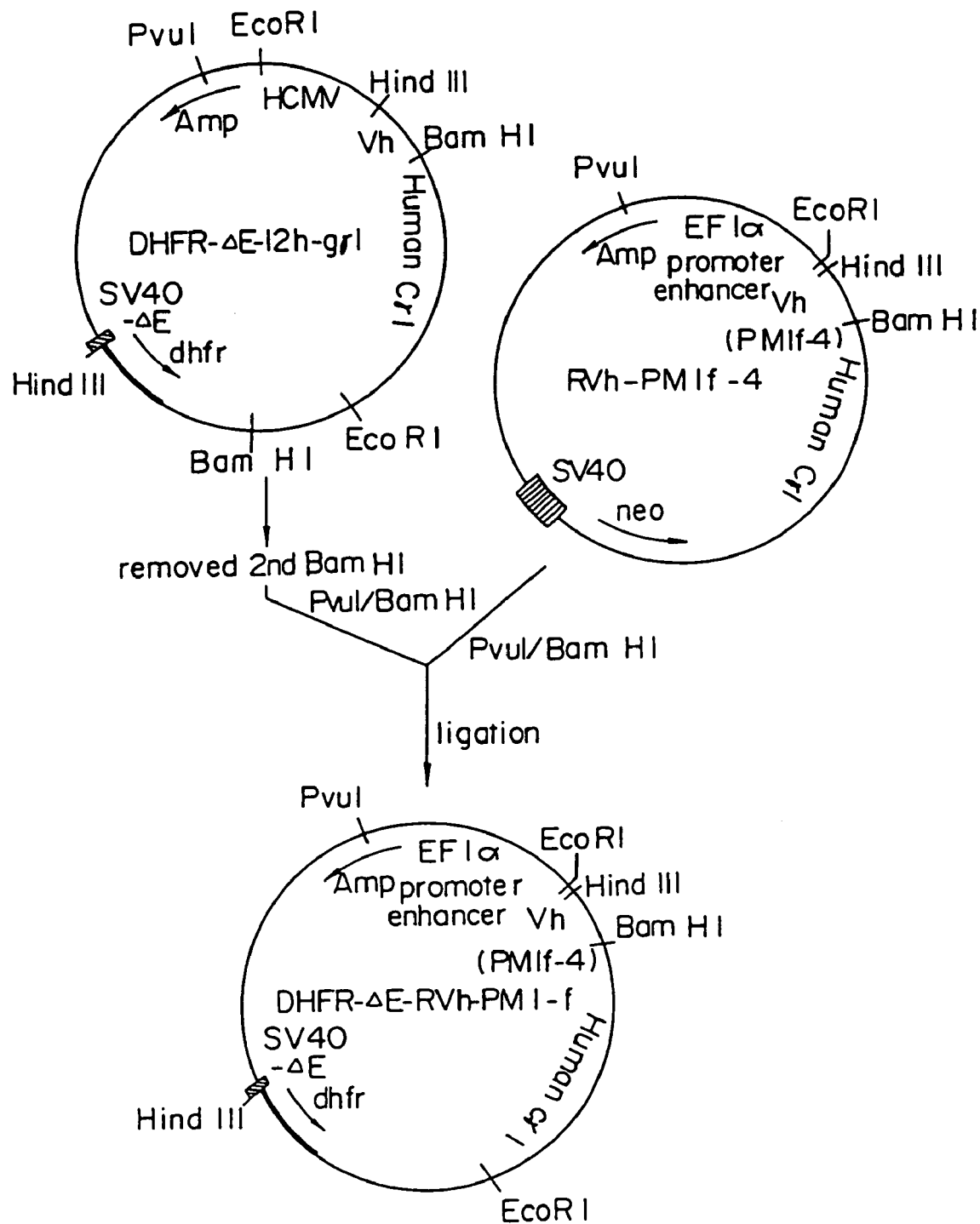
FIG. 11 represents a process for the construction of an expression plasmid DHFR-ΔE-RVh-PM1-f comprising EF1α promoter/enhancer and dhfr gene linked to a defective SV40 promoter/enhancer sequence for amplification, useful for expression of an H chain.

Construction of Vectors that Employ the Dihydrofolate Reductase (dhfr) Gene Linked to a Defective SV40 Promoter-Enhancer Sequence to Achieve High Levels of Expression of Genetically-Engineered Antibodies in CHO Cells (FIG. 10 and FIG. 11).

In order to remove the enhancer sequence from the SV40 early promoter, the plasmid DNA pSV2-dhfr (S. Subramani et al., Mol. Cell. Biol. (1981) 1: 854-864) (ATCC 33694) was digested with SphI and PvuII, filled-in with Klenow polymerase, and self-ligated to yield pSV2-dhfr-ΔE (see FIG. 10). An approximately 3.7 kb EcoRI fragment containing the HCMV promoter, the H chain V region, and the human gamma-1 C region was excised from HCMV-PMh-gγ1 by partially digesting with EcoRI. This fragment was ligated to EcoRI-digested pSV2-dhfr-ΔE to yield DHFR-ΔE-PMh-gγ1.

A similar vector was constructed based on the H chain expression vector that employs the HEF-1α promoter-enhancer (see FIG. 11). An approximately 3.7 kb EcoRI fragment derived from HCMV-12h-gγ1 was ligated with EcoRI-digested pSV2-dhfr-ΔE to yield DHFR-AE-12h-gγ1. The BamHI site following the dhfr cDNA sequence in DHFR-ΔE-

12h-gγ1 was removed by partially digesting with BamHI, filling-in with Klenow polymerase, and self-ligating. An approximately 4 kb PvuI-BamHI fragment containing the dhfr cDNA was excised from the modified DHFR-ΔE-12h-gγ1 DNA and ligated to an approximately 3 kb PvuI-BamHI fragment from RVh-PM1f-4 (constructed in Example 12) to yield DHFR-ΔE-RVh-PM1f.

The improved expression plasmids as prepared above can be used for the production of the reshaped human PH-1 antibodies of the present invention.

Example 11

Expression and Analysis of Different Versions of Reshaped Human PM-1 Antibody

The HEF-1α vectors expressing reshaped human PM-1 L and H chains were co-transfected into cos cells. As a standard control, HEF-1α vectors expressing chimeric PM-1 L and H chains were also co-transfected into cos cells. After 3 days the medium from the transfected cos cells was collected and analyzed by ELISA (1) for the amount of human IgG antibody present in the supernatant and (2) for the ability of that human IgG to bind to IL-6R. Later the same samples were also tested by ELISA for the ability of the antibody to inhibit human IL-6 from binding to human IL-6R.

Figure 12:
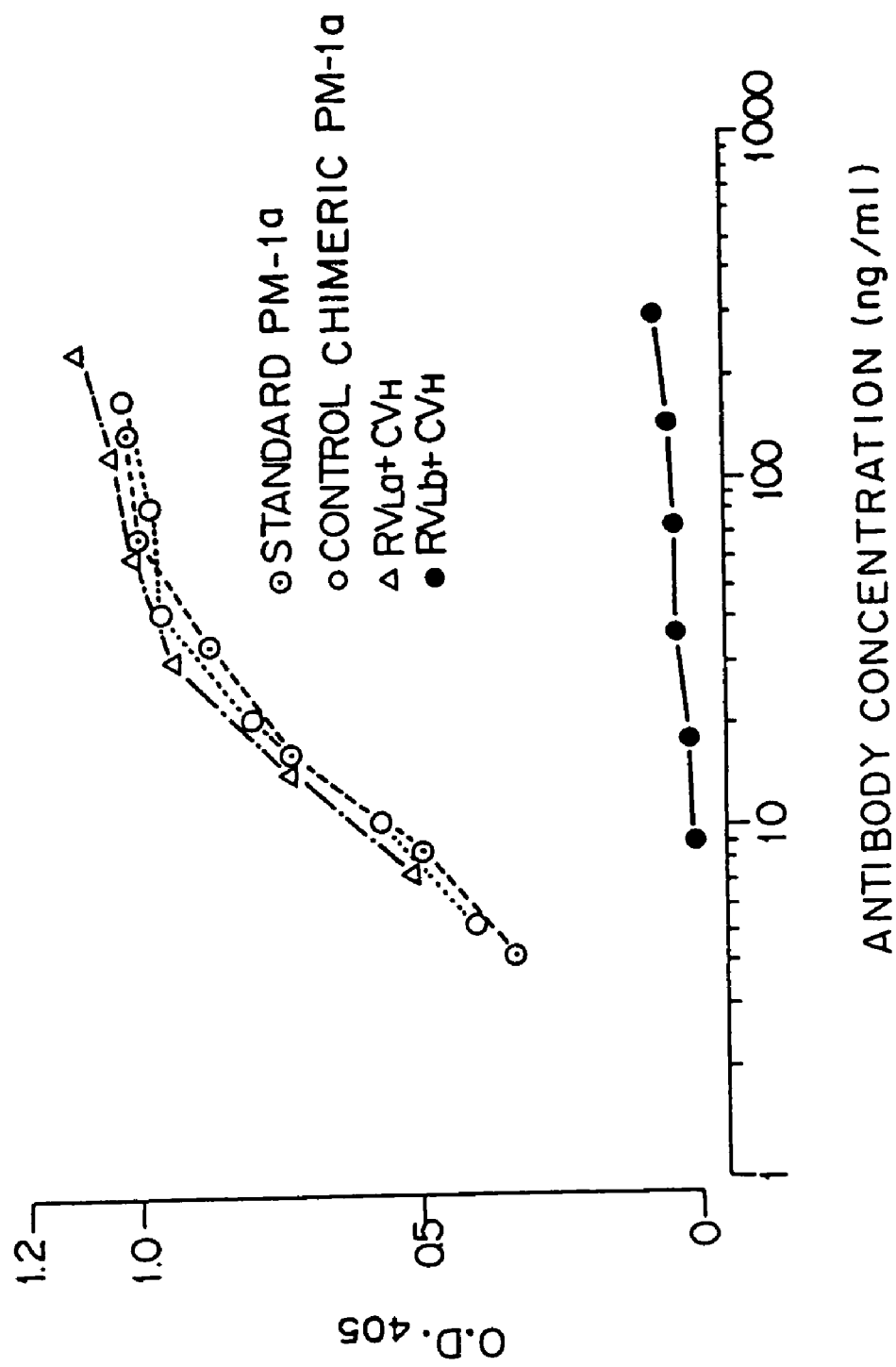
FIG. 12 is a graph showing an ability of version "a" and "b" of the reshaped human PM-1 L chain V region for binding to the human IL-6R.

Evaluation of the two versions of reshaped human PM-1 L chain V regions were conducted by co-transfecting cos cells with one of the two vectors expressing reshaped human PM-1 L chains (RV1-PM1a or RV1-PM1b) and the vector expressing chimeric PM-1 H chain (HCMV-PMh-gγ1). Cells were also co-transfected with vectors expressing chimeric PM-1 L and H chains (HCMV-PMka-gk and HCMV-PMh-gγ1). Data using unpurified cos cell supernatants showed that version "a" of reshaped human PM-1 L chain was equivalent to chimeric PM-1 L chain in assays for binding to IL-6R. Version "b" of reshaped human PM-1 L chain, however, virtually abolished binding to IL-6R (FIG. 12). From these results, it was concluded that the change at position 71 in FR3 from phenylalanine (as present in the human REI as modified for CAMPATH-1H) to tyrosine (as present in natural human REI and in mouse PM-1) was very detrimental to the formation of a functional antigen-binding site.

Version "a" of the reshaped human PM-1 L chain V region was selected as the best version. In subsequent experiments evaluating the different versions of reshaped human PM-1 H chain V regions, version "a" of the reshaped human PM-1 L chain V region was always used.

Evaluation of the six versions of reshaped human PM-1 H chain V regions were conducted by co-transfecting cos cells with one of the six vectors expressing reshaped human PM-1 H chains (RVh-PM1a, RVh-PM1b, RVh-PM1c, RVh-PM1d, RVh-PM1e or RVh-PM1f) and the vector expressing version "a" of the reshaped human PM-1 L chain (RV1-PM1a). Cells were also co-transfected with vectors expressing chimeric PM-1 L and H chains (HEF-PMK-gk and HEF-PMh-gγ1). Preliminary data using unpurified cos cell supernatants showed that version "a" of reshaped human PM-1 L chain and version "f" of reshaped human PM-1 H chain were equivalent to chimeric PM-1 L and H chains in assays for binding to IL-6R.

To confirm this preliminary data, chimeric and reshaped human PM-1 antibodies were concentrated and purified from cos cell supernatants using Protein A. Namely the media from cos cells was concentrated using a 100 kd cut-off ultrafiltration device (Amicon). The concentrated media was purified using Protein A agarose (Affi-Gel Protein A MAPSII kit, BioRad). Briefly, the concentrated media was applied to a Protein A agarose column that was equilibrated with five bed volumes of binding buffer. The column was washed with 15 bed volumes of the binding buffer, followed by 5 bed volumes of the elution buffer. The eluate was concentrated and the buffer changed to. PBS using a microconcentrator (Centricon 10, Amicon). The purified antibodies were used for further analysis.

Figure 13:
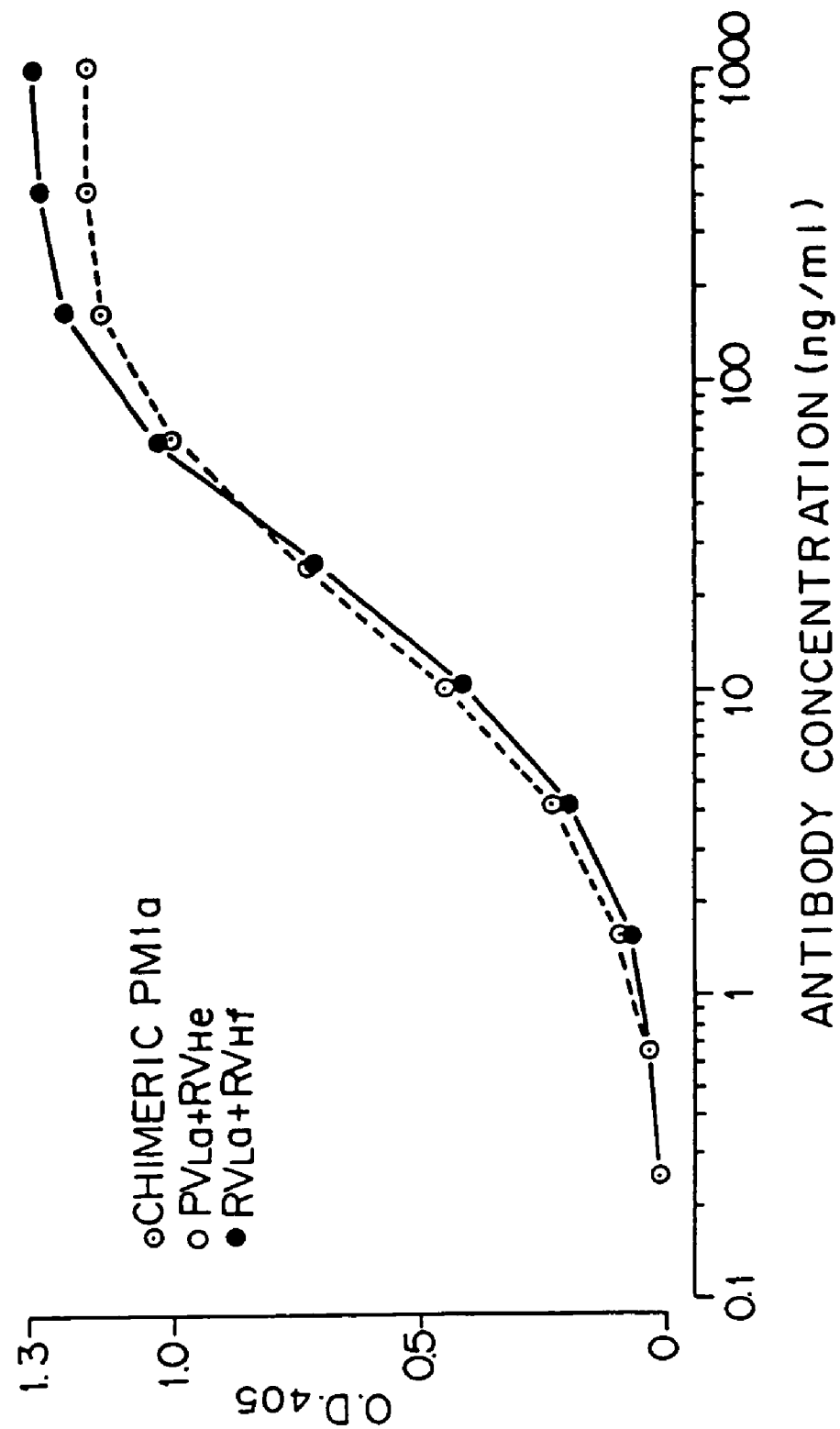
FIG. 13 is a graph showing an ability of version "f" of the reshaped human PM-1 H chain V region plus version "a" of the reshaped PM-1 L chain L chain V region for binding to the human IL-6R.
Figure 14:
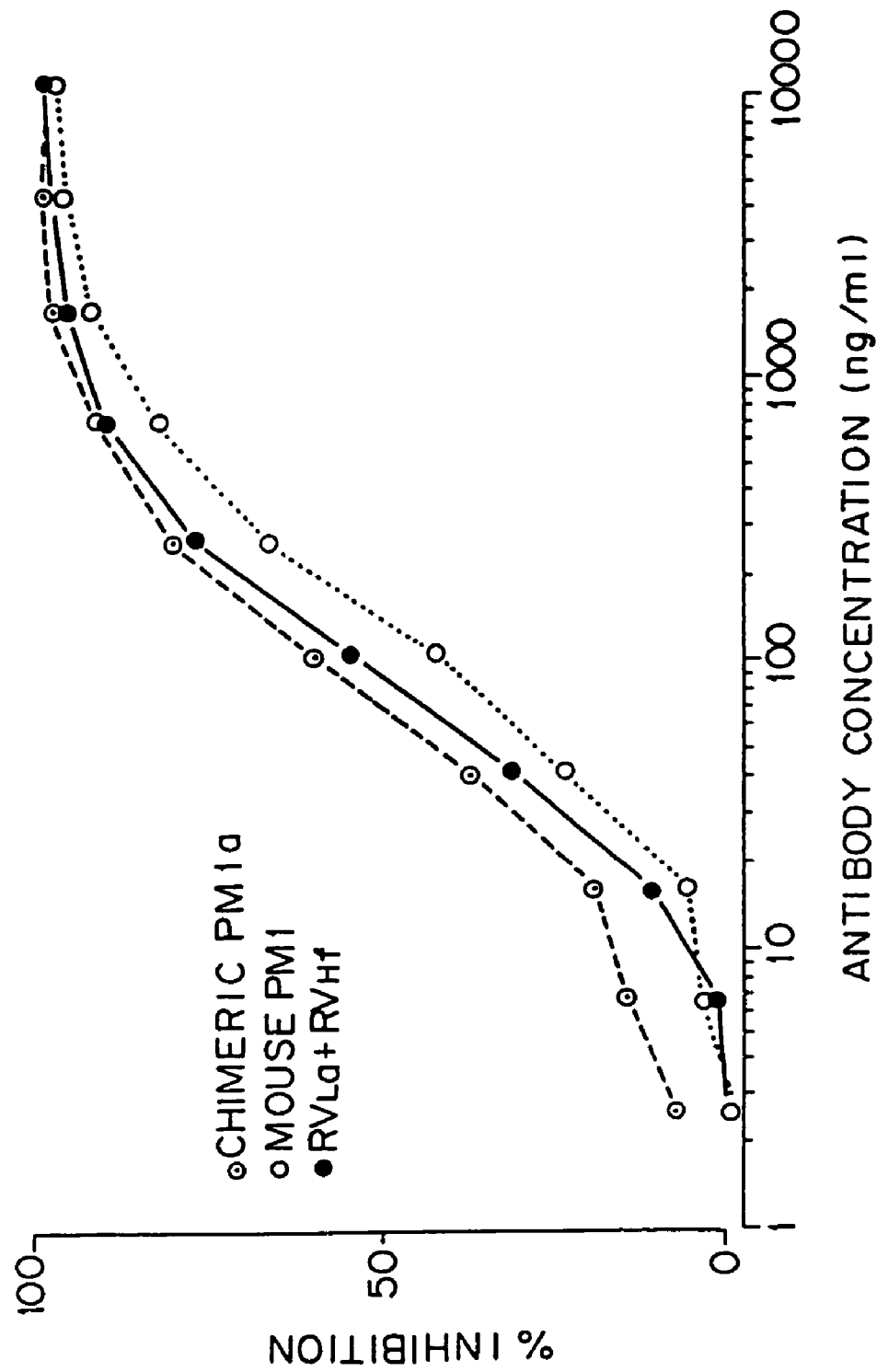
FIG. 14 is a graph showing an ability of vergion "f" of the reshaped PM-1 H chain V region plus version "a" of the reshaped PM-1 L chain V region to inhibit the binding of IL-6 to the human IL-6R.

The analysis of purified samples of chimeric PM-1 antibody, and reshaped human PM-1 antibodies with version "a" of the L chain V region and versions "a", "b", "c", "d", "e", and "if" of the reshaped human H chain V region was carried out. Version "a" of the L chain plus version "f" of the H chain is clearly the best reshaped human PM-1 antibody. It binds to IL-6R as well as chimeric PM-1 antibody does (FIG. 13). It also inhibits human IL-6 from binding to the IL-6R as well as both the mouse and chimeric PM-1 antibodies do (FIG. 14).

Example 12

Reconstruction of the Reshaped Human PM-1 V Regions to Improve the Levels of Expression.

In order to remove the introns within the DNA sequences coding for the leader sequences of the reshaped human PM-1 L and H chain V regions (see SEQ ID Nos: 61 and 63), the cDNAs coding for the V regions were recloned using the PCR primers. The L and H chain expression vectors RV1-PM1a and RVh-PM1f were co-transfected into cos cells. After 48 hrs, total RNA was prepared (Chirgwin et al., Biochemistry (1979) 18:5294-5299) and 5 μg of total RNA was used for the first strand cDNA synthesis as described for the PCR cloning of mouse antibody V regions. Three PCR primers were designed and synthesized. LEV-P1 (SEQ ID NO: 71) and HEV-P1 (SEQ ID NO: 69) contain the splice donor sequence and the BamHI site and were used as forward primers for the L and H chain V regions, respectively. HEV-P2 (SEQ ID NO: 70) contains the Kozak consensus sequence before the ATG initiation codon and the HindIII site and was used as a backward primer for both the L and H chain V regions. Each 100 μl PCR reaction contained 20 mM Tris-HCl (pH 8.8), 10 mM KCl 10 mM $(NH_4)_2SO_4$, 2 mM $MgSO_4$, 0.1% Triton X-100, 0.1 μg BSA, 250 μM dNTPs, 2.5 u of Vent DNA polymerase (Biolabs, U.K.), 50% of the first-strand cDNA synthesis reaction and 100 pmoles each of the forward and backward primers. Each PCR tube was overlayed with 50 μl of mineral oil and then cycled, after an initial melt at 94° C. for 1.5 min, at 94° C. for 1 min, 50° C. for 1 min, and 72° C. for 1 min, and then at 72° C. for 10 min. The 408 bp PCR product containing the L chain V region and the 444 bp PCR product containing the H chain V region were purified using 2.0% low melting temperature agarose gels, digested with BamHI and HindIII, and subcloned into a pUC19 vector to obtain pUC-RV1-PM1a-3 and pUC-RVh-PM1f-3 respectively.

It was revealed that the DNA sequences of the reshaped human PM-1 L and H chain V regions contain inappropriate splice donor and acceptor sites (see SEQ ID NOs: 61 and 63). The sites within the L chain V region are not frequently used (approximately 10% of the mRNA), but the sites within the H chain V region are used frequently (approximately 90% of the mRNA). This aberrant splicing resulted in low levels of expression of the reshaped human PM-1 antibody. In order to avoid aberrant splicing in the V regions, the splice donor sites were removed using a PCR-based method. For the H chain V region, the backward primer NEW-SP1 (SEQ ID NO: 72) and the forward primer NEW-SP2 (SEQ ID NO: 73) were synthesized, changing the DNA sequence TGG GTG AGA to the DNA sequence TGG GTT CGC. The conditions for the PCR reactions were as described above for cDNA cloning except that the template DNA was 50 ng of pUC-RVh-PM1f-3 and the primers were either HEV-P2 and NEW-SP2, or HEV-P1 and NEW-SP1.

The PCR products from the two PCR reactions were purified using a 2.0% low melting temperature agarose gel and used in a PCR joining reaction. A 98 µl PCR reaction containing 0.5 µg of each of the first PCR products and 5 u of Vent DNA polymerase was incubated at 94° C. for 2 min, 50° C. for 2 min, and 72° C. for 5 min, and then 100 pmoles each of HEV-P1 and HEV-P2 primers were added. The PCR tube was overlayed with 30 µl of mineral oil and subjected to 25 cycles of PCR, at 94° C. for 1 min, 50° C. for 1 min, and 72° C. for 1 min, and then incubated at 72° C. for 10 min.

In the same manner, the splice donor site in the reshaped human PM-1 L chain V region was removed using PCR primers REI-SP1 (SEQ ID NO: 74) and REI-SP2 (SEQ ID NO: 75) that changed the DNA sequence CAG GTA AGG to the DNA sequence CAG GAA AGG (see). Both PCR products, a 408 bp DNA fragment for the L chain V region and a 444 bp DNA fragment for the H chain V region, were purified using a 2.0% low melting temperature agarose gel, digested with HindIII and BamHI, and subcloned into a pUC19 vector to yield pUC-RV1-PM1a-4 and pUC-RVh-RM1f-4, respectively.

RVh-PM1f-4 was constructed by replacing the HindIII-BamHI fragment of RVh-PM1f with the HindIII-BamHI fragment excised from pUC-RVh-PM1f-4. Sequence of reshaped human PM-1 antibody L chain V region version "a" wherein introns have been deleted is shown in SEQ ID NO: 67 and 68, and sequence of reshaped human PM-1 antibody H chain V region version "f" wherein have been deleted is shown in SEQ ID NOs: 65 and 66.

Example 13

Figure 16:
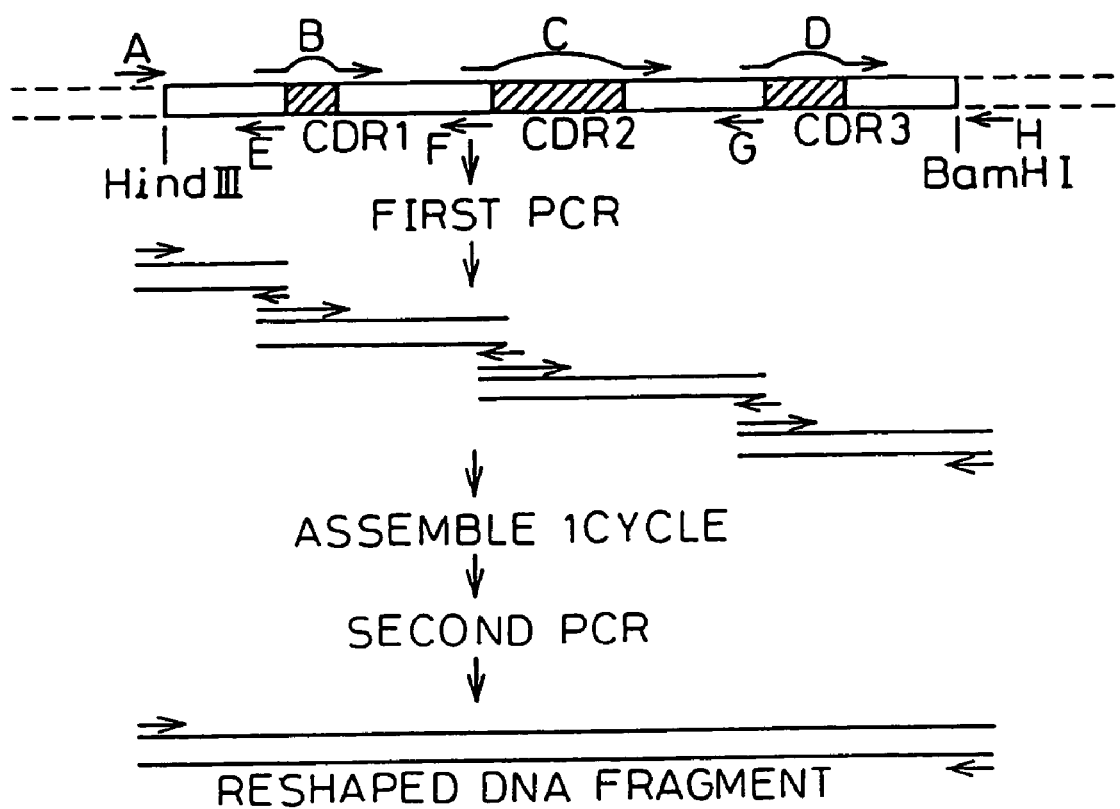
FIG. 16 shows a process for construction of DNA coding for reshaped human AUK 12-20 antibody L chain V region.

Construction of DNA Coding for Reshaped Human AUK 12-20 Antibody L Chain V Region A process for construction of DNA coding for a reshaped human AUK 12-20 antibody L chain V region is shown in FIG. 16. A gene coding for a human antibody L chain V region is incorporated into pUC19 vector using restriction enzymes HindIII and BamHI. Eight PCR primers (A to H) are prepared, and in the first PCR 4 regions which form a gene coding for the V region are amplified. The primers A and H have homology to DNA sequences on the pUC19 vector. The primers B, C and D are primers of 40 to 60 bp length each having a gene sequence of CDR to be grafted, respectively. The primers E, F and G have homology to DNA sequence of 15 to 20 bp length of the 5'-terminus of the primers B, C and D, respectively. Four first PCR use pairs of primers A and E, B and F. C and G, as well as D and H, respectively.

The PCR product A-E encodes FR1, and the PCR product B-F encodes CDR1 and FR2. The 3'-terminal portion of the A-E fragment and the 5'-terminal portion of the B-F fragment have homology in their 15 to 20 bp length, allowing to join there fragments at latter stage. Similarly, the B-F fragment has a homology with the C-G fragment which encodes CDR2 and FR3. The C-G fragment further has a homology with the D-H fragment which encodes CDR3 and FR4. Thus, these 4 fragments can be joined by their mutual homology. After joining these 4 fragments in a PCR reaction mixture, primers A and H are added thereon in the second PCR to amplify a product formed by correct joining of the 4 fragment. The second PCR product thus obtained has three grafted CDRs, and after digestion with HindIII and BamHI, is subcloned into pUC19 vector.

More specifically, as a template, plasmid pUC-RV1-PM1a-4 constructed by inserting a DNA encoding reshaped human PM-1 antibody L chain V region version "a" into plasmid pUC19 was used.

The above-mentioned primers A to H have the following sequences.

| Backward Primer | SEQ ID NO. | Forward primer | SEQ ID NO. |
|---|---|---|---|
| A. REVERSE | 95 | 1220-L16 | 66 |
| B. 1220-L1 | 76 | 1220-L2b | 68 |
| C. 1220-L2 | 78 | 1220L3b | 70 |
| D. 1220-L3 | 80 | UNIVERSAL | 82 |

The backward primers 1220-L1, 1220-L2 and 1220L3 for CDR grafting were purified with 12% polyacrylamide gel containing 8M area prior to using them.

A 100 µl PCR reaction mixture contained 20 mM Tris-HCl (pH 8.8), 10 mM KCl, 10 mM $(NH_4)_2SO_4$, 2 mM $MgSO_4$, 0.1% Triton X-100, 1 µg BSA, 250 µm dNTPs, 5 units Vent DNA polymerase (BioLabs. U.K.), 50 ng pUC-RV1-PM1a-4 DNA, and 100 p moles each of the forward and backward primers.

Each PCR tube was overlaid with 50 µl of mineral oil, and after an initial denaturation at 94° C. for 1.5 minutes, 30 cycles of reaction at 94° C. for 1 minute, 50° C. for 1 minute and 72° C. for 1 minute was carried out, followed by an incubation at 72° C. for 10 minutes.

Each of the PCR products, 252 bp (A-E), 96 bp (B-F), 130 bp (C-G) and 123 bp (D-H) was purified with a 2.0% low melting agarose (FMC, Bio. Products, USA). Namely, an agarose piece containing a DNA fragment was excised, melted at 65° C. for 5 minutes, and added to the same volume of 20 mM Tris-HCl (pH 7.5) containing 2 mM EDTA and 200 mM NaCl. The mixture was extracted with phenol and chloroform. The DNA fragment was recovered by an ethanol precipitation, dissolved in 10 mM Tris-HCl (pH 7.5) containing 1 mM EDTA, and used for PCR joining reaction.

Next, 98 µl of a PCR reaction mixture containing 0.2 µg each of the first PCR products and 5 units of Vent DNA polymerase was incubated at 94° C. for 2 minutes, 50° C. for 2 minutes and 72° C. for 5 minutes for a joining reaction. Next, 100 p moles each of the primers A (REVERSE) and H(UNIVERSAL) were added to the reaction mixture to make it to 100 µl volume, and the reaction mixture was overlaid with 50 µl of mineral oil and subjected to 30 cycles of a reaction at 94° C. for 1 minute, 50° C. for 1 minute and 72° C. for 1 minute, followed by an incubation at 72° C. for 10 minutes.

The second PCR product of 558 bp length containing an L chain V region into which CDRs of the mouse monoclonal antibody AUK 12-20 L chain had been grafted was purified by a 2.0% low melting agarose gel, and after digestion with BamHI and HindIII, subcloned into a pUC19 vector to obtain pUC-RLL-1220a, and sequenced. A resulting amino acid sequence of the L chain V region and a nucleotide sequence encoding the amino acid sequence is shown in SEQ ID NOs: 82 and 83.

Next, for construction of an L chain expression vector, a HindIII-BamHI DNA fragment containing a reshaped human AUK 12-20 antibody L chain V region was excised from the above-mentioned plasmid pUC-$RV_L$-1220a, and inserted to HindIII-BamHI site of an L chain expression vector HEF-12k-gk to obtain an expression vector $RV_L$-1220a for reshaped human AUK 12-20 antibody L chain V region version "a".

Example 14

Expression and Analysis of Reshaped Human AUK 12-20 Antibody L Chain

Transient Expression in COS Cells

The expression vector $RV_L$-1220a for reshaped human AUK 12-20 antibody L chain and the expression vector HEF-12h-gγ1 for chimeric 12-20 antibody H chain (Example 5) were cotransfected into COS cells to evaluate the reshaped human AUK 1220 antibody L chain version "a". Namely, COS cells were suspended in a phosphate-buffeted saline (PBS) at a concentration of $1 \times 10^7$ cells 1 ml, and to 0.8 ml of the suspension were added the plasmid DNAs (10 µg for each plasmid). Pulses were applied to the suspension at an electric capacity of 1,900 V, 25 µF using a Gene Pulser apparatus (Bio Rad).

After restoration at a room temperature for 10 minutes, electroporated cells were added to 8 ml of DMEM medium (GIBCO) containing 10% bovine fetal serum. After incubation for 72 hours, supernatant was collected, centrifuged to eliminate cell debris, and stored in an aseptic condition at 4° C. for short period or at −20° C. for longer period.

Determination of Human-Like Antibody by ELISA

A supernatant of the transfected COS cells was assaied by ELISA and the production of chimeric antibody was confirmed. To detect human-like antibody, a plate was coated with a goat anti-human IgG (whole molecule) (Sigma). After blocking, the supernatant from COS cells was sequentially diluted and added to each well.

The plate was incubated and washed, and an alkaline phosphatase-conjugated goat anti-human IgG (α-chain specific, Sigma) was added thereon. After incubation and washing, a substrate solution was added. After further incubation, the reaction was terminated and an optical density at 405 nm was measured. As a standard, purified IgG (Sigma) was used.

ELISA for Confirmation of an Ability to Bing to Human IL-6R

A supernatant from the transfected COS cells was assaied by ELISA to determine whether the produced human-like antibody can bind to the antigen, human IL-6R. A plate was coated with a mouse monoclonal antibody MT18 (Reference Example 1). After blocking with 1% BSA, soluble recombinant human IL-6R(SR 344) was added to the plate. After washing the plate, supernatant from COS cells was sequentially diluted and added to each well of the plate. After inclusion and washing, alkaline phosphatase-conjugated goat anti-human IgG was added to the wells, and after further incubation and washing, a substrate solution was added thereon. After incubation, the reaction was terminated and optical density at 405 nm was measured.

Figure 17:
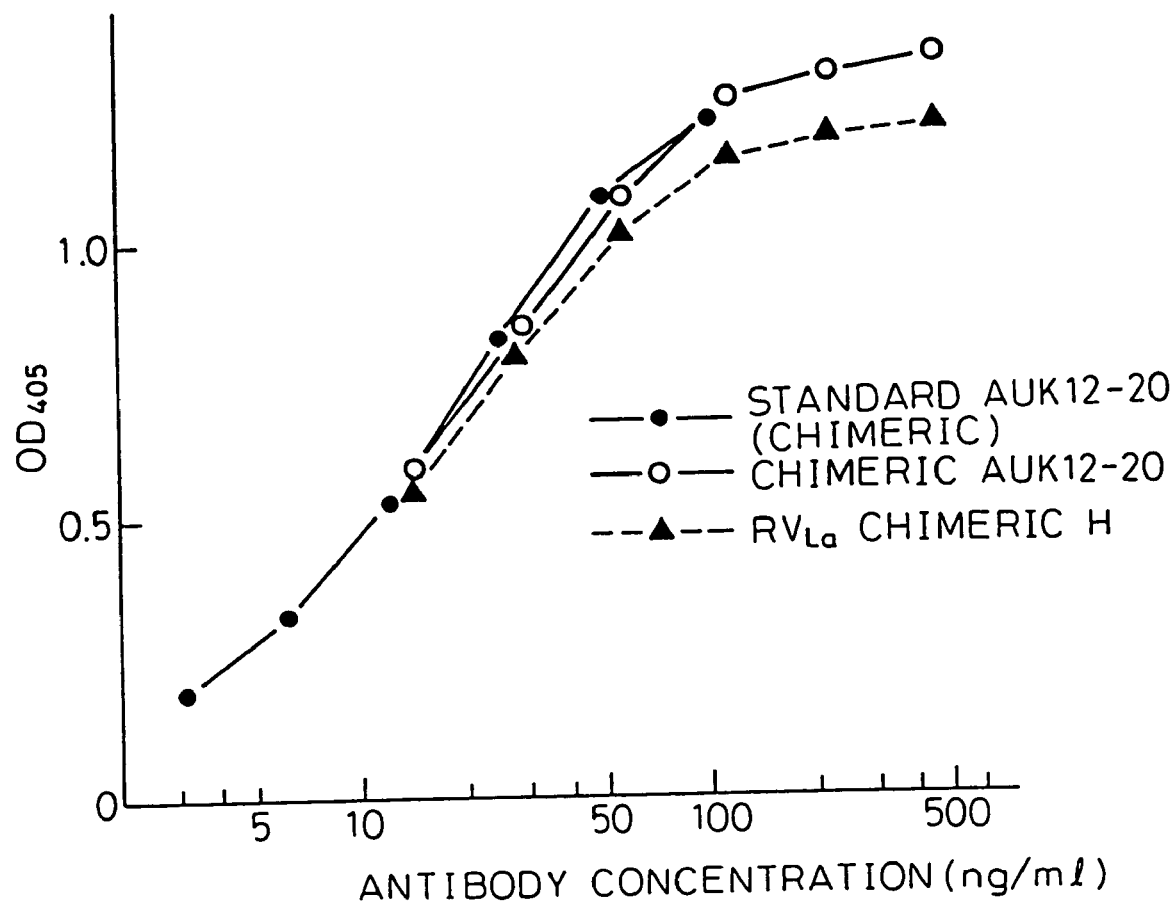
FIG. 17 is a graph showing results of an ELISA for confirm of an ability of a reshaped human AUK 12-20 antibody L chain V region to bind to human IL-6R. In the Figure, "Standard AUK 12-20 (chimera) means a result for chimeric AUK 12-20 antibody produced by CHO cells and purified in a large amount.

A result is shown in FIG. 17. The human-like antibody comprising a combination of a reshaped human AUK 12-20 antibody L chain version "a" and a chimeric 12-20 antibody H chain exhibited a binding ability to IL-6R as strong as chimeric 12-20 antibody. Optical density at 405 nm changed in a dilution rate-dependent manner, confirming that the sample contains an antibody to IL-6R. In addition, this result shows that the reshaped human AUK 12-20 antibody L chain version "a" has an antigen binding ability as high as chimeric AUK 12-20 antibody L chain.

Example 15

Construction of Gene Coding for Reshaped Human AUK 12-20 Antibody H Chain Using HSGI Consensus Sequence According to the same procedure as described in Example 13. CDRs of AUK 12-20 antibody H chain V region were grafted into the reshaped human $V_H$a425 containing HSG I consensus sequences as its FRs (Kettleborough et al., Protein Engineering (1991) 4:773-783). Fist, a HindIII-BamHI DNA fragment encoding the reshaped human $V_H$a425 (FIG. 3 in the literature) was excised from a plasmid HCMV-$RV_H$a-425-γ1 and subcloned at HindIII-BamHI sites in pUC 19 vector to obtain pUC-$RV_H$-425a, which was then used as a template. 8 PCR primers (A1 to H1) were synthesized. The primer 1220-H1 was designed to graft CDR1 and to induce a mutation from T-28 to S-28, and the primer 1220-H3 was designed to graft CDR3 and to induce a mutation from S-94 to R-94. The primers 1220-H1, 1220-H2 and 1220-H3 were purified using a 12% polyacrylamide gel containing 8 M urea prior to using them. Nucleotide sequence of each primer was as follow.

| Backward primer | SEQ ID NO. | Forward primer | SEQ ID NO. |
|---|---|---|---|
| A1. REVERSE | 95 | E1. 1220-H1b | 73 |
| B1. 1220-H1 | 84 | E1. 1220-H2b | 75 |
| C1. 1220-H2 | 86 | G1. 1220-H3b | 77 |
| D1. 1220-H3 | 88 | H1. UNIVERSAL | 82 |

Condition of PCR was the same as that described in Example 13, except that the pUC-$RV_H$-425a was used as a template DNA and the above-mentioned primers were used for grafting H chain CDRs. Primer pairs of A1 and E1, B1 and F1, C1 and G1, as well as D1 and H1 were used to carry out first PCR reactions, and the respective first PCR products, 186 bp (A1-E1), 75 bp (B1-F1), 173 bp (C1-G1) and 105 bp (D1-H1) were purified with 2.0% low melting agarose gel, and used in subsequent second PCR joining reaction. According to the condition described in Example 13, 0.2 µg each of the first PCR products were used to carry out the second PCR reaction (including PCR joining reaction) to obtain a PCR product of 495 bp containing DNA coding for a human H chain V region into which mouse AUK 12-20 antibody H chain V region CDRs had been grafted, and the PCR product was purified using 2.5% low melting agarose gel. After digesting the PCR product with BamHI and HindIII, resulting BamHI-HindIII DNA fragment was subcloned into pUC19 and sequenced to obtain pUC-$RV_H$-1220a.

It was revealed that DNA sequence coding for reshaped human AUK 12-20 antibody H chain V region contains a sequence well conforming to a splicing donor sequence, which may cause an abnormal splicing which was troublesome in the production of the reshaped human PM-1 antibody. Therefore, this DNA sequence was modified by PCR. Mutagenetic primers, SGI-SP1 (SEQ ID NO: 112) and SGI-SP2 (SEQ ID NO: 113) were synthesized. These primers convert the DNA sequence AAG GTG AGC to the DNA sequence AAA GTC AGC. Condition of PCR reaction was same as described above, except that 50 ng of pUC-$RV_H$-1220a was used as a template DNA, and the SGI-SP1 and UNIVERSAL (SEQ ID NO: 94), or the SGI-SP2 and REVERS (SEQ ID NO: 95) were used as primers.

PCR products from two PCR reactions were purified by 2% low melting agarose gel and used in a PCR joining reaction.

98 μl of PCR reaction mixture containing 0.2 μg each of the first PCR products and 5 units of Vent DNA polymerase was incubated at 94° C. for 2 minutes, at 55° C. for 2 minutes and at 72° C. for 5 minutes for a joining reaction. Next, 100 pmoles each of UNIVERSAL and REVERSE primers were added to the reaction mixture, which was then overlaid with 50 μl of mineral oil and subjected to 30 cycles of second PCR reaction consisting of incubations at 94° C. for 1 minutes, at 50° C. for 1 minute and at 72° C. for 1 minute, followed by an incubations at 72° C. for 10 minutes. DNA fragment of 495 bp obtained in the second PCR was purified by a 2.0% low melting agarose gel, and subcloned into pUC19 vector and sequenced to obtain pUC-$RV_H$-1220a-2.

Next, HindIII-BamHI DNA fragment containing DNA coding for reshaped human AUK 12-20 antibody H chain V region was excised from the pUC-$RV_H$-1220a-2, and inserted at HindIII-BamHI sites of an H chain expression vector HEF-12h-gγ1 to obtain an expression vector $RV_H$-1220a for the reshaped human AUK 12-20 antibody H chain version "a".

For construction of genes coding for reshaped human AUK 12-20 antibody H chain V region versions "b" to "d", two pairs of mutagenic primers were synthesized. Each PCR reaction was carried out under substantially the same condition as described above. For construction of version "b", in two first PCR reactions, either UNIVERSAL primer (SEQ ID NO: 94) and mutagenic primer 120H-ml (SEQ ID NO: 90), or REVERSE primer (SEQ ID NO: 95) and mutagenic primer 1220H-mlb (SEQ ID NO: 91), as well as pUC-$RV_H$-1220a as a template were used. The first PCR products of 202 bp and 323 bp were purified by a 2.0% low melting agarose gel, and used in second PCR (including PCR joining reaction) under the same condition as described above to obtain a 495 bp product (version "b"). The product was digested with HindIII and BamHI, and subcloned into pUC19 vector to obtain pUC-$RV_H$-1220b.

Similarly, mutagenic primer 1220H-m2 (SEQ ID NO:92), 1220H-m2b (SEQ ID NO: 93) and a template pUC-$RV_H$-1220a were used in a PCR to obtain a PCR product (version "c"). The product was digested with HindIII-BamHI and inserted at HindIII-BamHI sites of pUC19 vector to obtain pUC-$RV_H$-1220c. Moreover, mutagenic primers 1220H-mla (SEQ ID NO: 90), 1220H-mlb (SEQ ID NO: 91), and a template pUC-$RV_H$-1220c were used to obtain a PCR Product (version "d"), which was then digested with HindIII and BamHI and inserted into HindIII-BamHI sites of pUC19 vector to obtain pUC-$RV_H$-1220d.

Note, an amino acid sequence of the reshaped human AUK 12-20 antibody H chain V region version "b" and a nucleotide sequence coding therefor in the plasmid pUC-$RV_H$-1220b is shown in SEQ ID NOs: 97 and 96; and an amino acid sequence of the reshaped human AUK 12-20 antibody H chain V region version "d" and a nucleotide sequence coding therefor in the plasmid pUC-$RV_H$-1220d is shown in SEQ ID NOs: 99 and 98.

Next, to construct the expression vectors, HindIII-BamHI fragments containing a reshaped human AUK 12-20 antibody H chain V region were excised from pUC-$RV_H$-1220b, pUC-$RV_H$-1220c and pUC-$RV_H$-1220d and inserted into HindIII-BamHI sites of H chain expression vector HEF-12h-gγ1 to obtain $RV_H$-1220b, $RV_H$-1220c and $RV_H$-1220d respectively.

Example 16

Expression and Analysis of Various Versions of Reshaped Human AUK 12-20 Antibody.

Figure 18:
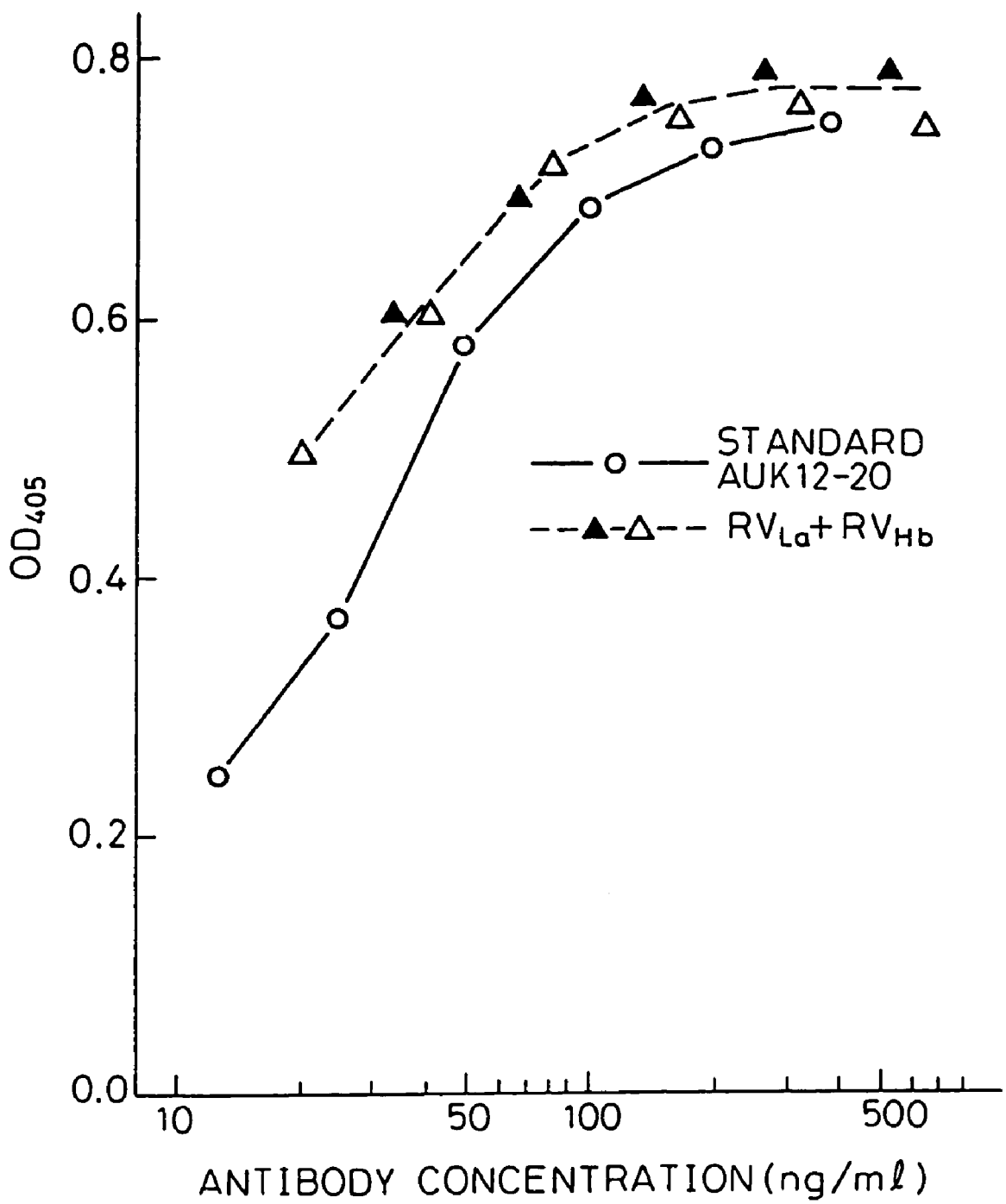
FIG. 18 is a graph showing a result of an ELISA for an ability of a reshaped human AUK 12-20 antibody (L chain version "a"+H chain version "b") to bind to human IL-6R.
Figure 19:
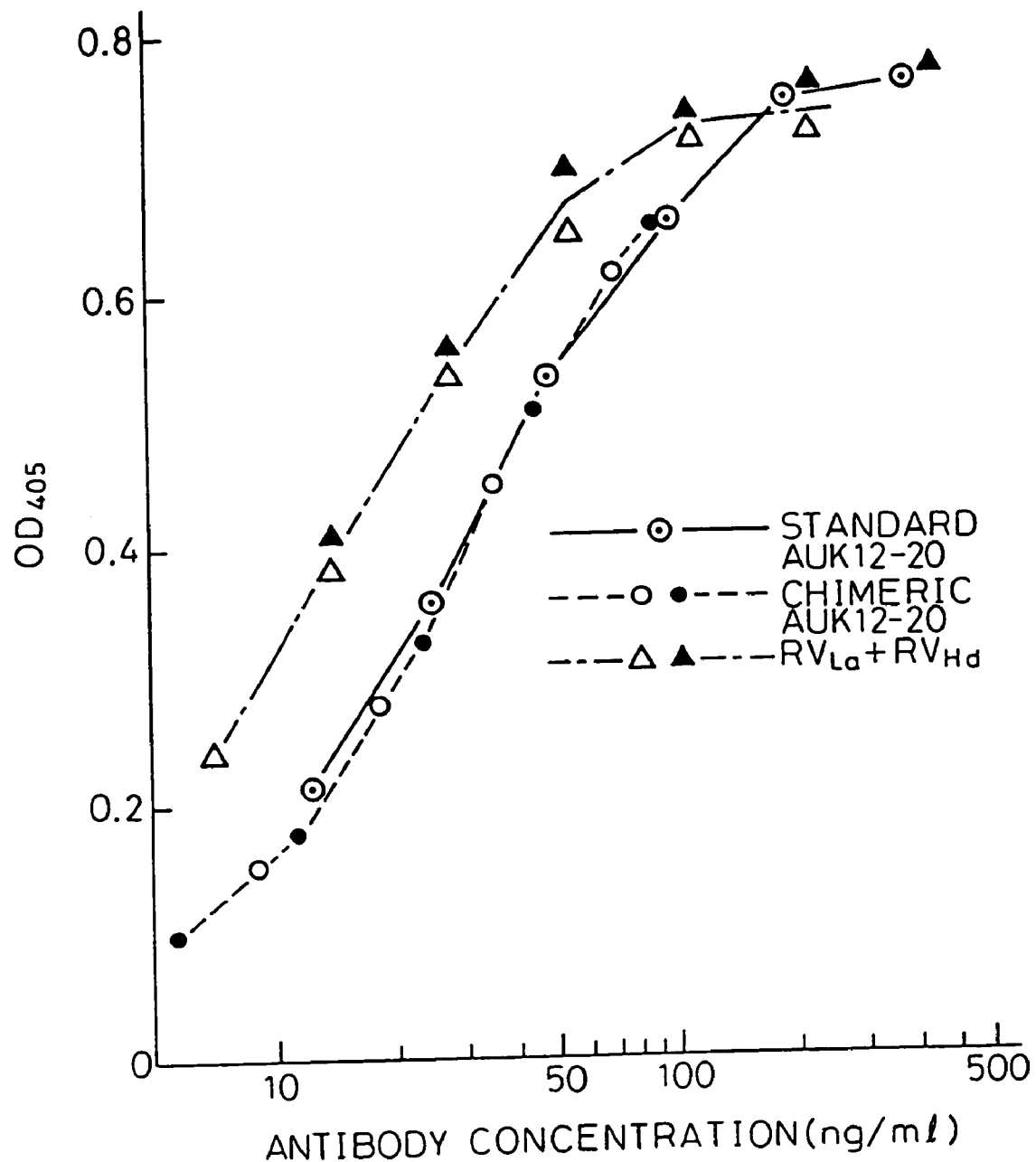
FIG. 19 is a graph showing a result of an ELISA for an ability of a reshaped human AUK 12-20 antibody (L chain version "a"+H chain version "d") to bind to the human IL-6R.

COS cells were cotransfected with one of 4 expression vectors for reshaped human AUK 12-20 antibody H chain ($RV_H$-1220a, $RV_H$-1220b, $RV_H$-1220c or $RV_H$-1220d) and an expression vector $VR_L$-1220a to evaluate 4 versions of the reshaped human AUK 12-20 antibody H chain V region. For reference, COS cells were cotransfected with expression vectors for chimeric 12-20 antibody L chain and H chain (HEF-12h-gγ1 and FEF-12-gk). In an assay for binding to the human IL-6R, a reshaped human AUK 12-20 antibody consisting of reshaped human AUK 12-20 antibody L chain and reshaped human AUK 12-20 antibody H chain version "b", and a reshaped human AUK 12-20 antibody consisting of reshaped human AUK 12-20 antibody L chain and reshaped human AUK 12-20 antibody H chain version "d" shows good binding as well as chimeric 12-20 antibody. These results are shown in FIGS. 18 and 19.

Example 17

Construction of Gene Coding for Reshaped Human sle 1220 Antibody H Chain Using Human Antibody HAX A human antibody having the highest homology with the mouse monoclonal antibody AUK 12-20 H chain V region is HAX (J. Immunology (1987) 139:2496-2501; an antibody produced by hybridoma 21/28 derived from B cells of an SLE patient; its amino acid sequence is shown in FIG. 6, and nucleotide sequence therefor is shown in FIGS. 4 and 5 of this literature), according to a protein data base "Leeds". Reshaped Human sle 1220H antibody H chain V region was constructed using FRs of the antibody HAX and CDRs of mouse monoclonal antibody AUK 12-20 H chain V region.

An entire DNA coding for a reshaped human sle 1220 H antibody H chain V region version "a" was chemically synthesized. DNA coding for sle 1220 H antibody H chain V region of an entire length 439 bp was designed by dividing the DNA into 6 oligonucleotides of 90 to 94 bp length overlapping each other by 21 bp (sle 1220 h 1 to 6;SEQ ID NOs: 100 to 105, respectively) In designing the oligonucleotides, secondary structure was tested and for sites having structural problems the third nucleotide in a codon was changed without change of amino acid encoded thereby. The relationship of these oligonucleotides and a process for construction of double-stranded synthetic DNA are shown in FIG. 20.

Figure 20:
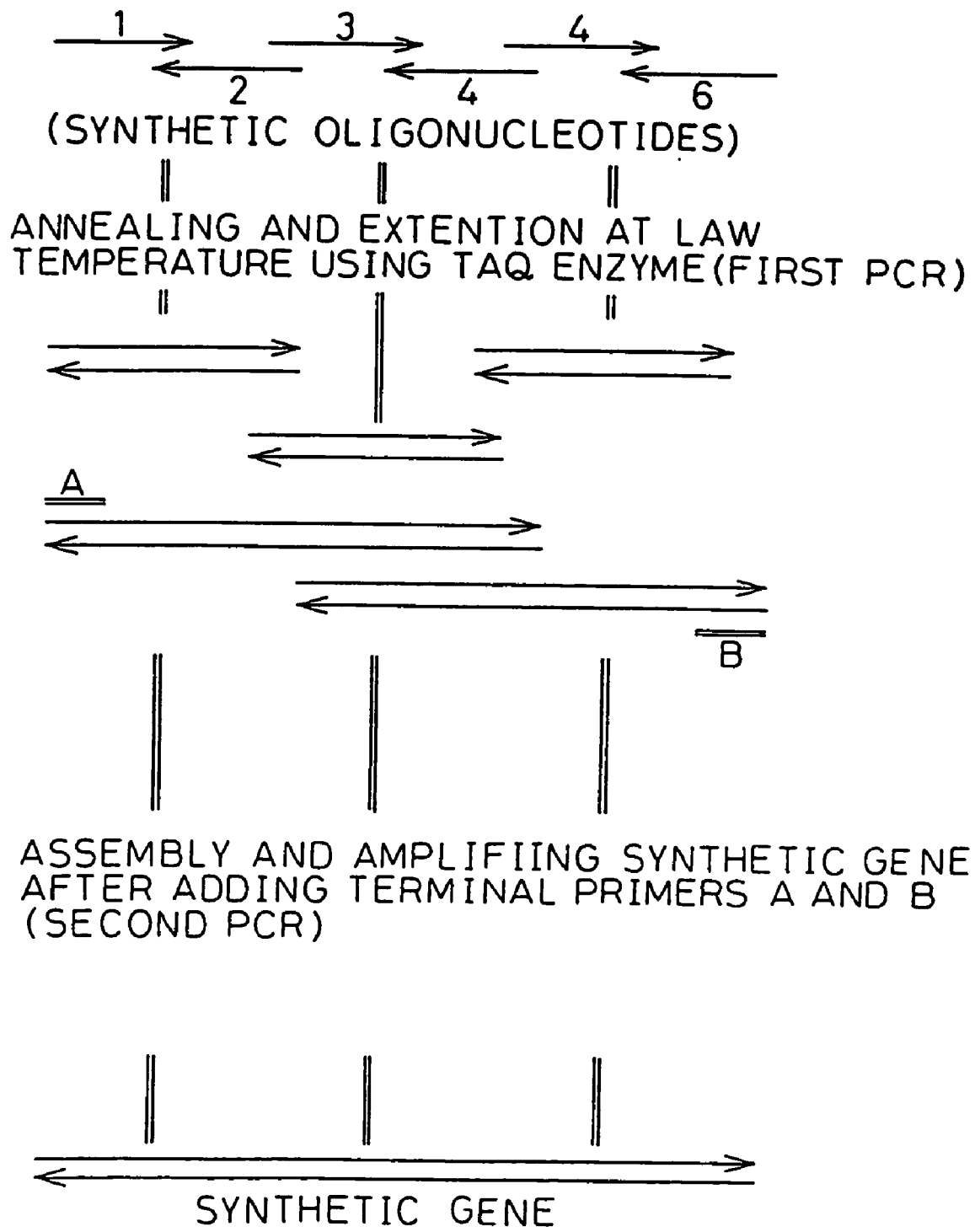
FIG. 20 shows a process for chemical synthesis of a reshaped Human sle 1220 H antibody H chain V region.
Figure 21:
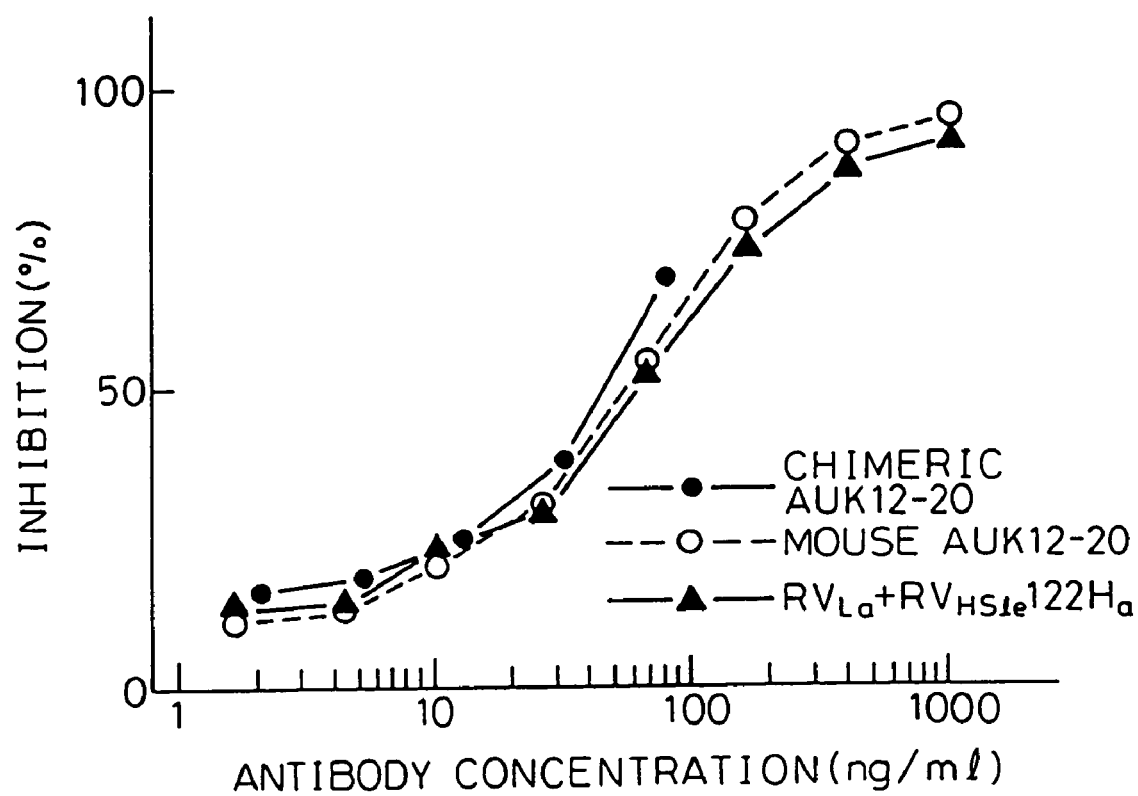
FIG. 21 is a graph showing a result of an ELISA for an ability of a reshaped Human sle 1220 antibody (L chain version "a"+H chain version "a") to inhibit the binding of IL-6 to the human IL-6R.
Figure 22:
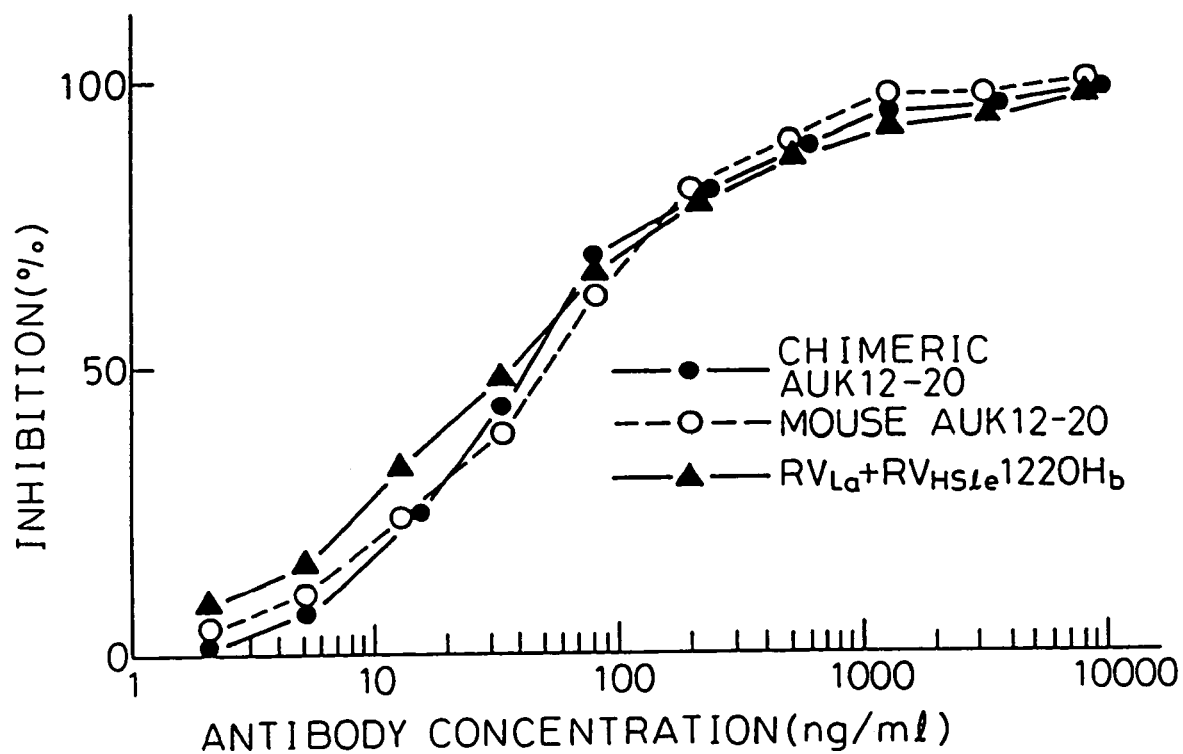
FIG. 22 is a graph showing a result of an ELISA for an ability of a reshaped Human sle 1220 antibody (L chain version "a"+H chain version "b") to inhibit the binding of IL-6 to the human IL-6R.
Figure 23:
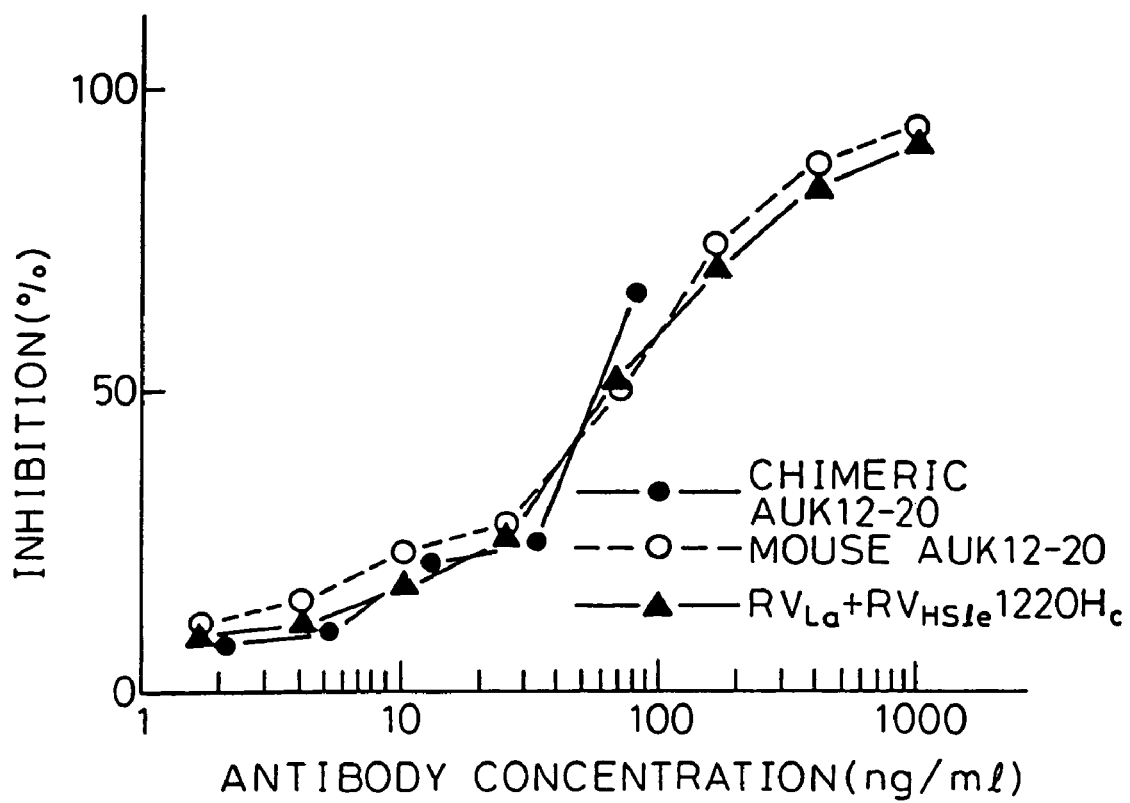
FIG. 23 is a graph showing a result of an ELISA for an ability of a reshaped Human sle 1220 antibody (L chain version "a"+H chain version "c") to inhibit the binding of IL-6 to the human LI-6R.
Figure 24:
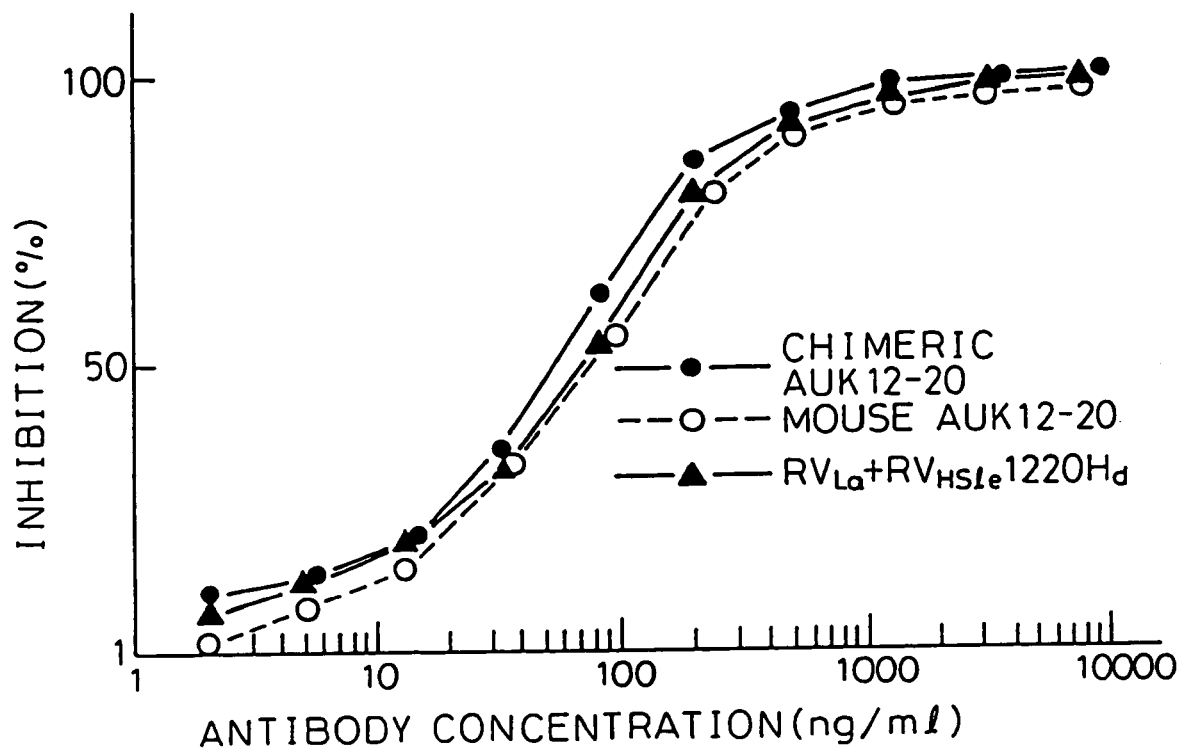
FIG. 24 is a graph showing a result of an ELISA for an ability of a reshaped Human sle 1220 antibody (L chain version "a"+H chain version "d") inhibit the binding of IL-6 to the human LI-6R.

The reaction shown in FIG. 20 is carried out using PCR technique. Namely, 6 synthetic oligonucleotides were added to a single PCR reaction tube to carry out the first PCR reaction, thereby two oligonucleotides are anealed and extended, and further 4 oligonucleotides or an entire oligonucleotide are obtained.

Next, terminal primers A (SEQ ID NO: 106) and B (SEQ ID NO: 107) are added to carry out the second PCR reaction, wherein only a correct oligonucleotide having an entire length can be amplified. The resulting product is digested with BamHI and HindIII, and subcloned into pUC19 vector, followed by sequencing.

More specifically, 98 μl of a reaction mixture containing 100 mM tris-HCl (pH 8.5), 50 mM KCl, 0.1 mM dATP, 0.1 mM dGTP, 0.1 mM dCTP, 0.1 mM dTTP, 1.5 mM $MgCl_2$ and 2.5 U of DNA polyrnerase AmpliTaq (Perkin Elmer Cetus) as well as 5 pmoles each of the oligonucleotides was denatured at 94° C. for 1.5 minutes and subjected to 3 cycles of reaction by incubation at 92° C. for 3 minutes, 50° C. for 2 minutes and 72° C. for 5 minutes, followed by an incubation at 72° C. for 10 minutes. One μl each of 50 mM terminal primers A and B were added to the reaction mixture, which was then overlaid with 80 μl of mineral oil, and after denaturation of 94° C. for 1.5 minutes, subjected to 30 cycles of reaction by incubation at 94° C. for 1 minute, 50° C. for 1 minute and at 72° C. for 1 minute, followed by an incubation at 72° C. for 10 minutes. The PCR product of 439 bp was purified by a 1.5% low melting agarose gel, digested with restriction enzymes BamHI HindIII, and subcloned into pUC19 vector, followed by confirmation of sequence. A clone thus obtained was designated pUC-$RV_H$-sle 1220Ha. An amino acid sequence of reshaped human sle 1220H antibody H chain V region version "a" and a nucleotide coding therefor in the plasmid pUC-$RV_H$-sle 1220Ha are shown in SEQ ID NO: 108.

Next, HindIII-BamHI DNA fragment containing a gene coding for reshaped human 12-20 (sle 1220H) antibody H chain V region was excised from the pUC-$RV_H$-sle 1220Ha and inserted at HindIII-BamHI sites of an H chain expression vector HEF-12h-gγ1 to obtain $RV_H$-sle 1220Ha.

For construction of version "b" to "d" of reshaped human sle 1220H antibody H chain V region, two mutagenic primers sle 1220Hml (SEQ ID NO: 110) and sle l1220Hm2 (SEQ ID NO: 111) were synthesized. In each PCR, Vent DNA polymerase and reaction mixture composition described in Example 13 were use. In each PCR reaction, a reaction mixture containing pUC-$RV_H$-sle 1220Ha as template, 50 pmoles of a mutagenic primer sle 1220Hml or sle 1220Hm2, and 50 pmoles of the terminal primer B was denaturated at 94° C. for 1.5 minutes, and subjected to 30 cycles of reaction by incubation at 94° C. for 1 minute, at 50° C. for 1 minute and at 72° C. for 1 minute, followed by an incubation at 72° C. for 10 minutes. The product of 235 bp or 178 bp was purified by a 1.5% low melting agarose gel to use as a primer in the second PCR reaction. Namely the second PCR reaction was carried out using 50 pmoles of the terminal primer A, 0.2 μg of the PCR product and pUC-$RV_H$-sle 1220Ha as a template, and resulting product of 439 bp was purified by a 1.5% low melting agarose gel, digested with BamHI and HindIII, and subcloned into pUC19 vector to obtain pUC-$RV_H$-sle 1220Hb or pUC-$RV_H$-sle 1220Hc, which encodes reshaped human sle 1220 antibody H chain V region version "b" or "c", respectively.

A DNA coding for reshaped Human sle 1220 H antibody H chain V region version "d" was constructed also follow. As a templete pUC-RVh-sle 1220Hb was used. 50 pmoles each of a mutagenic primer sle 1220Hm2 and the terminal primer B was used to carry out 30 cycles of the first PCR reaction. Resulting 176 bp PCR product was purified on a 1.6% low melting agarose gel to use as a primer in the second PCR. This primer and 50 p moles of the terminal primer A was used in the second PCR to obtain a 439 bp DNA fragment. The PCR product thus obtained was purified, digested with BamHI and HindIII, and subcloned into pUC 19 vector to obtain pUC-$RV_H$-sle 1220Hd.

Next, to construct expression vectors for various versions of reshaped Human sle 1220H antibody H chain V region, BamHI-HindIII fragments containing a DNA encoding reshaped Human sle 1220 antibody H chain V region were excised from pUC-$RV_H$-sle 1220Hb, PUC-$RV_H$-sle 122Hc and pUC-$RV_H$-sle 1220Hd, and inserted into HindIII-BamHI sites of the H chain expression vector HEF-12h-gγ1 to obtain expression vectors $RV_H$-sle 1220Hb, $RV_H$-sle 1220Hc and $RV_H$-sle 1220Hd respectively.

Each of four vectors expressing reshaped human sle 1220H antibody H chain ($RV_H$-sle 1220Ha, $RV_H$-sle 1220Hb and $RV_H$-sle 1220Hc or $RV_H$-sle 1220Hd) and the vector $RV_L$-1220a expressing reshaped human AUK 12-20 antibody L chain were cotransfected to COS cells to evaluate the four versions of the reshaped human sle 1220H antibody H chain V region for an ability to inhibit the binding of IL-6 to IL-6R. Results is shown in FIGS. 21 to 24. Note, these result were obtained after purifying the produced antibodies by protein A.

As seen from the above, according to the present invention, in a chimeric L chain or a resahped human L chain, or a chimeric H chain or a reshaped human H chain, and especially in RF, one or more than one amino acid can be replaced with other amino acid maintaining an ability to bind to human IL-6R. Therefore, the present invention includes chimeric antibody and reshaped human antibody, chimeric L chain and reshaped human L chain, chimeric H chain and reshaped human H chain, reshaped L chain V region, and reshaped H chain V region, wherein one or more than one amino acid is replaced with other as well as DNA coding therefor, as far as they maintain their native property.

Starting hybridomas used in the present invention were constructed as follows.

Reference Example 1

Construction of Hybridoma MT18

To construct a hybridoma producing monoclonal antibody to human IL-6R, as an immunogen, a mouse T cell line expressing human IL-6R on the cell surface was constructed as follows. Namely, a plasmid pBSF2R.236 disclosed in Japanese Patent Application No. H1-9774 and pSV2neo was transfected into a mouse T cell line CTLL-2 (ATCC TIB214) according to a conventional procedure, and the resultant transformant was screened using G418 according to a conventional procedure to obtain a cell line expressing about 30,000 IL-6Rs per cell. This cell line was designated CTBC3.

The CTBC3 cells were cultured in RPMI 1640 according to a conventional procedure, the cultured cells were washed four times with PBS buffer, and $1 \times 10^7$ cells were intraperitoneally injected to C57BL/6 mice for immunization. The immunization was carried out once a week for 6 weeks.

Spleen cells were obtained from the immunized mice and fused with myeloma P3U1 cells using polyethylene glycol according to a conventional procedure, and the fused cells were screened as follows. The IL-6R negative human T cell line JURKAT (ATCC CRL 8163) was co-transfected with the plasmids pBSF2R.236 and pSV2neo, and transformed cells were screened to obtain a cell line expressing about 100,000 IL-6Rs per cell. The cell line was designated NJBC8. A hybridoma cell clone producing an antibody which recognized NP40-lysed NJBC8 but did not recognize NP40-lysed JURKAT was cloned and designated MT18. The hybridoma MT18 was deposited with the Fermentation Research Institute Agency of Industrial Science and Technology (FRI), under the Budapest Treaty, as FERM BP-2999 on Jul. 10, 1990.

Reference Example 2

Construction of Hybridoma PM1

To construct a hybridoma producing monoclonal antibody to the IL-6R, as an antigen, human IL-6R was extracted as follows. $3 \times 10^9$ human myeloma U266 cells (IL-6R-producing cells) were lysed in 1 ml of 1% digitonin, 10 mM triethanolamine buffer (pH 7.4), 0.15 M Nacl and 1 mM PMSF (phenylmethylsulfonyl fluoride; Wako Pure Chemicals). On the other hand, an MT18 antibody produced by the MT18 hybridoma prepared in Reference Example 1 was bonded to cyanogen bromide-activated Sepharose 4B (Pharmacia) according to a conventional procedure. This MT18 antibody-conjugated Sepharose 4B was mixed with the above-prepared cell lysate to bind the solubilized IL-6R to the MT18 antibody on Sepharose 4B. Substances non-specifically bonded to the Sepharose 4B were washed off, and the IL-6R bound to Sepharose 4B via the MT18 antibody was used as an immunogen.

BALB/c mice were intraperitoneally immunized with the above-prepared immunogen, once a week for 4 weeks. Next, spleen cells were obtained from the immunized mice, and fused with myeloma cells P3U1 using polyethylene glycol according to a conventional procedure. The fused cells were screened as follows. First, a culture supernatant and 0.01 ml of Protein G Sepharose (Pharmacia) were mixed to adsorb immunoglobulin in the supernatant to the Protein G Sepharose. On the other hand, $10^7$ U266 cells internally labeled with $^{35}$S-methionine were lysed, and the IL-6R was affinity-purified using the MT18-conjugated Sepharose 4B. Next, the $^{35}$S-methionine-labeled IL-6R was immunoprecipitated with the above-prepared Protein G Sepharose on which an immunoglobulin had been bonded, and the precipitate was analyzed by SDS/PAGE. As a result, one hybridoma clone producing antibody which specifically bound to the IL-6R was isolated, and designated PM1. The hybridoma PM1 was deposited with the FRI under the Budapest Treaty as FERM BP-2998, on Jul. 10, 1990.

Reference Example 3

Construction of Hybridoma AUK12-20, AUK64-7 and AUK146-15

As an immunogen, a soluble IL-6R(SR 344) was prepared according to a procedure described by Yasukawa, K. et al., J. Biochem. 108, 673-676, 1990. Namely, a plasmid pECEdhfr 344 containing a cDNA coding for IL-6R wherein the 345th codon from the N-terminus had been replaced by a stop codon was transfected to CHO (5E27) cells, the transfected cells were cultured in a serum-free medium (SF—O medium, Sanko Junyaku), and a resulting supernatant was concentrated with an HF-Lab1 system (Tosoh), and purified by Blue-5PW column and Phenyl-5PW column. The purified soluble IL-6R showed a single band in an SDS-PAGE.

A female BALB/cAnNCrj mouse (Nippon CREA) was subcutaneously injected with 10 μg/mouse of the immunogen in Freund's complete adjuvant (Bacto Adjuvant Complete H 37 Ra, Difco), followed by the second and third injections of the same amount of the immunogen in Freund's incomplete adjuvant (Bacto Adjuvant Incomplete Freund, Difco) two and three weeks after the first injection, respectively. A final immunization (the fourth injection) was carried out without adjuvant into a tail vein one week after the third injection. A serum sample was prepared from the immunized mice, serially diluted with a dilution buffer, and assayed by ELISA according to a procedure described by Goldsmith, P. K., Analytical Biochemistry, 117, 53-60, 1981. Namely, an SR344 (0.1 μ/ml)-coated plate was blocked with 1% BSA, and the diluted sample was added thereon. Mouse IgG bound to the SR344 was measured using goat anti-mouse IgG/alkaline phosphatase (A/P) (ZYMED) and a substrate for alkaline phosphatase (Sigma-104).

After confirming an increase of the anti-SR344 antibody in the serum, spleen cells were obtained from 5 BALB/c mice three days after the final immunization. The spleen cells and myeloma cells (P3U1) were mixed at a ratio of 25:1, fused using PEG1500, and cultured in 2000 wells at a cell concentration of 0.7 to $1.1 \times 10^6$ cells/well. Supernatants from the wells were screened for their ability to bind SR344 (the first screening designated as R344 recognition assay), and for their ability to inhibit a binding of SR344 with an interleukin-6 by a IL-6/sIL-6R binding inhibition assay (RBIA). The first screening provided 240 positive wells, and the second screening provided 36 positive wells.

The above-mentioned R344 recognition assay was carried out as follows. Goat anti-mouse Ig (Cappel) (1 μg/ml)-coated plate (MaxiSorp, Nunc) was blocked with 1% BSA, and 100 μl/well of hybridoma culture supernatant was added thereon, followed by an incubation at room temperature for one hour. After washing the plate, 20 μg/ml of SR344 was added to each well, and incubation was carried out at room temperature for one hour. The amount of SR344 captured by the immobilized antibody derived from the supernatant was determined by addition of rabbit anti-SR344 IgG (#2, 5 μg/ml), goat anti-rabbit IgG-alkaline phosphatase (A/P) (1:3000, Tago), and of a substrate (1 mg/ml, Sigma-104), followed by measurement of the optical dencity at 405-600 nm.

The above-mentioned RBIA was carried out as follows. MT18 antibody-coated plate was filled with 100 μg/ml of SR344 (100 μl/well), and incubation was carried out at a room temperature for one hour. After washing the plate, 50 μl/well of hybridoma supernatant and 50 μg/well of biotin-interleukin-6 conjugate (20 μg/ml) were simultaneously added to each well, and the wells were incubated at room temperature for one hour. An amount of biotin-IL-6 bound to SR344 was measured by an addition of streptavidin-A/P (1:7000, PIERCE) and a corresponding substrate (Sigma-104), followed by a measurement of the optical density at 405-600 nm.

Finally, positive clones were purified by a twice-repeated limiting dilution method, and three hybridoma clones, i.e., AUK12-20, AUK145-15 and AUK64-7, which inhibit the binding of SR344 with the IL-6; and a hybridoma clone AUK181-6, which does not inhibit the binding of SR344 with the IL-6, were obtained.

INDUSTRIAL APPLICABILITY

The present invention provides a reshaped human antibody to the human IL-6R, comprising a human antibody wherein the CDRs of the human V regions are replaced with the CDRs of a mouse monoclonal antibody to the human IL-6R. Since major portion of the reshaped human antibody is derived from a human antibody and the mouse CDRs which are less antigenic, the present reshaped human antibody is less immunogenic to human, and therefore is promised for therapeutic uses.

Reference to Deposited Microorganisms Under Rule 13-2 of Budapest Treaty

Depository Authority: National Collections of Industrial and Marine Bacteria Limited Address: 23 St Macher Drive, Aberdeen AB2 IRY, UNITED KINGDOM

| Identification of Microorganism | Deposition No. | Deposition Date |
| --- | --- | --- |
| E. Coli DH5α, pPM-h1 | NCIMB 40362 | Feb. 12, 1991 |
| E. Coli DH5α, p12-h2 | NCIMB 40363 | Feb. 12, 1991 |
| E. Coli DH5α, p64-h2 | NCIMB 40364 | Feb. 12, 1991 |

53

-continued

| Identification of Microorganism | Deposition No. | Deposition Date |
|---|---|---|
| E. Coli DH5α, p146-h1 | NCIMB 40365 | Feb. 12, 1991 |
| E. Coli DH5α, pPM-k3 | MCIMB 40366 | Feb. 12, 1991 |
| E. Coli DH5α, p12-k2 | NCIMB 40367 | Feb. 12, 1991 |
| E. Coli DH5α, p64-k4 | NCIMB 40368 | Feb. 12, 1991 |
| E. Coli DH5α, p146-k3 | NCIMB 40369 | Feb. 12, 1991 |

54

Depository Authority: Fermentation Research Institute, Agency of Industrial Science and Technology
Address: 103, Higashi 1-chome Tsukuba-shi Ibaraki Japan

| Identification of Microorganism | Deposition No. | Deposition Date |
|---|---|---|
| MT 18 | FERM BP-2999 | Jul. 10, 1990 |
| PM 1 | FERM BP-2998 | Jul. 10, 1990 |

The invention claimed is:

1. A chimeric antibody to human interleukin-6 receptor (IL-6R), comprising:
   (1) light chains (L chains) each comprising a human L chain constant region (C region) and an L chain variable region (V region) of a mouse monoclonal antibody to human IL-6R; and
   (2) heavy chains (H chains) each comprising a human H chain C region, and H chain V region of a mouse monoclonal antibody to human IL-6R;

wherein the mouse L chain V region includes an amino acid sequence shown in SEQ ID NO: 29; the mouse H chain V region includes an amino acid sequence shown in SEQ ID NO: 31; the human L chain C region is a human Kc region; and the human H chain C region is a human γ-1C region.

* * * * *

SEQUENCE LISTING (1) GENERAL INFORMATION:

(iii) NUMBER OF SEQUENCES: 134

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO: 1:

ACTAGTCGAC ATGAAGTTGC CTGTTAGGCT GTTGGTGCTG      40

(2) INFORMATION FOR SEQ ID NO: 2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO: 2:

ACTAGTCGAC ATGGAGWCAG ACACACTCCT GYTATGGGT      39

(2) INFORMATION FOR SEQ ID NO: 3:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide primer"

(xi) SEQUENCE DESCRIPTION: SEQ ID NO: 3:

ACTAGTCGAC ATGAGTGTGC TCACTCAGGT CCTGGSGTTG      40

(2) INFORMATION FOR SEQ ID NO: 4:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 4:

ACTAGTCGAC ATGAGGRCCC CTGCTCAGWT TYTTGGMWTC TTG                43

(2) INFORMATION FOR SEQ ID NO: 5:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 5:

ACTAGTCGAC ATGGATTTWC AGGTGCAGAT TWTCAGCTTC                    40

(2) INFORMATION FOR SEQ ID NO: 6:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 6:

ACTAGTCGAC ATGAGGTKCY YTGYTSAGYT YCTGRGG                       37

(2) INFORMATION FOR SEQ ID NO: 7:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 7:

ACTAGTCGAC ATGGGCWTCA AGATGGAGTC ACAKWYYCWG G                  41

(2) INFORMATION FOR SEQ ID NO: 8:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 8:

ACTAGTCGAC ATGTGGGGAY CTKTTTYCMM TTTTTCAATT G                  41

(2) INFORMATION FOR SEQ ID NO: 9:

(i) SEQUENCE CHARACTERISTICS:
            (A) LENGTH: 35 base pairs
            (B) TYPE: nucleic acid
            (C) STRANDEDNESS: single
            (D) TOPOLOGY: linear

```
        (ii) MOLECULE TYPE: other nucleic acid
            (A) DESCRIPTION: /desc = "Oligonucleotide primer"

(xi) SEQUENCE DESCRIPTION: SEQ ID NO: 9:

ACTAGTCGAC ATGGTRTCCW CASCTCAGTT CCTTG                                       35

(2) INFORMATION FOR SEQ ID NO: 10:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 10:

ACTAGTCGAC ATGTATATAT GTTTGTTGTC TATTTCT                                     37

(2) INFORMATION FOR SEQ ID NO: 11:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 11:

ACTAGTCGAC ATGGAAGCCC CAGCTCAGCT TCTCTTCC                                    38

(2) INFORMATION FOR SEQ ID NO: 12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 12:

GGATCCCGGG TGGATGGTGG GAAGATG                                                27

(2) INFORMATION FOR SEQ ID NO: 13:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 13:

ACTAGTCGAC ATGAAATGCA GCTGGGTCAT STTCTTC                                     37

(2) INFORMATION FOR SEQ ID NO: 14:

(i) SEQUENCE CHARACTERISTICS:
            (A) LENGTH: 36 base pairs
            (B) TYPE: nucleic acid
            (C) STRANDEDNESS: single
```

(D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO: 14:

ACTAGTCGAC ATGGGATGGA GCTRTATCAT SYTCTT                                 36

(2) INFORMATION FOR SEQ ID NO: 15:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO: 15:

ACTAGTCGAC ATGAAGWTGT GGTTAAACTG GGTTTTT                                37

(2) INFORMATION FOR SEQ ID NO: 16:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO: 16:

ACTAGTCGAC ATGRACTTTG GGYTCAGCTT GRTTT                                  35

(2) INFORMATION FOR SEQ ID NO: 17:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO: 17:

ACTAGTCGAC ATGGACTCCA GGCTCAATTT AGTTTTCCTT                             40

(2) INFORMATION FOR SEQ ID NO: 18:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide primer"

(xi) SEQUENCE DESCRIPTION: SEQ ID NO: 18:

ACTAGTCGAC ATGGCTGTCY TRGSGCTRCT CTTCTGC                                37

(2) INFORMATION FOR SEQ ID NO: 19:

(i) SEQUENCE CHARACTERISTICS:
          (A) LENGTH: 36 base pairs
          (B) TYPE: nucleic acid (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 19:

ACTAGTCGAC ATGGRATGGA GCKGGRTCTT TMTCTT                              36

(2) INFORMATION FOR SEQ ID NO: 20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 20:

ACTAGTCGAC ATGAGAGTGC TGATTCTTTT GTG                                 33

(2) INFORMATION FOR SEQ ID NO: 21:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 21:

ACTAGTCGAC ATGGMTTGGG TGTGGAMCTT GCTATTCCTG                          40

(2) INFORMATION FOR SEQ ID NO: 22:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 22:

ACTAGTCGAC ATGGGCAGAC TTACATTCTC ATTCCTG                             37

(2) INFORMATION FOR SEQ ID NO: 23:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide primer"

(xi) SEQUENCE DESCRIPTION: SEQ ID NO: 23:

GGATCCCGGG CCAGTGGATA GACAGATG                                       28

(2) INFORMATION FOR SEQ ID NO: 24:

(i) SEQUENCE CHARACTERISTICS:
            (A) LENGTH: 393 base pairs (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..393

(ix) FEATURE:
        (A) NAME/KEY: sig_peptide
        (B) LOCATION: 1..60

(ix) FEATURE:
        (A) NAME/KEY: mat_peptide
        (B) LOCATION: 61..393

(xi) SEQUENCE DESCRIPTION: SEQ ID NO: 24:

```
ATG GAG TCA GAC ACA CTC CTG CTA TGG GTA CTG CTG CTC TGG GTT CCA         48
Met Glu Ser Asp Thr Leu Leu Leu Trp Val Leu Leu Leu Trp Val Pro
-20             -15                 -10                 -5

GGT TCC ACT GGT GAC ATT GTG CTG ACA CAG TCT CCT GCT TCC TTA GGT         96
Gly Ser Thr Gly Asp Ile Val Leu Thr Gln Ser Pro Ala Ser Leu Gly
                 1               5                  10

GTA TCT CTG GGG CAG AGG GCC ACC ATC TCA TGC AGG GCC AGC AAA AGT        144
Val Ser Leu Gly Gln Arg Ala Thr Ile Ser Cys Arg Ala Ser Lys Ser
         15                  20                  25

GTC AGT ACA TCT GGC TAT AGT TAT ATG CAC TGG TAC CAA CAG AAA CCA        192
Val Ser Thr Ser Gly Tyr Ser Tyr Met His Trp Tyr Gln Gln Lys Pro
     30                  35                  40

GGA CAG ACA CCC AAA CTC CTC ATC TAT CTT GCA TCC AAC CTA GAA TCT        240
Gly Gln Thr Pro Lys Leu Leu Ile Tyr Leu Ala Ser Asn Leu Glu Ser
 45                  50                  55                  60

GGG GTC CCT GCC AGG TTC AGT GGC AGT GGG TCT GGG ACA GAC TTC ACC        288
Gly Val Pro Ala Arg Phe Ser Gly Ser Gly Ser Gly Thr Asp Phe Thr
                 65                  70                  75

CTC AAC ATC CAT CCT GTG GAG GAG GAG GAT GCT GCA ACC TAT TAC TGT        336
Leu Asn Ile His Pro Val Glu Glu Glu Asp Ala Ala Thr Tyr Tyr Cys
             80                  85                  90

CAG CAC AGT AGG GAG AAT CCG TAC ACG TTC GGA GGG GGG ACC AAG CTG        384
Gln His Ser Arg Glu Asn Pro Tyr Thr Phe Gly Gly Gly Thr Lys Leu
         95                 100                 105

GAA ATA AAA                                                            393
Glu Ile Lys
    110
```

(2) INFORMATION FOR SEQ ID NO: 25:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 25:

```
Met Glu Ser Asp Thr Leu Leu Leu Trp Val Leu Leu Leu Trp Val Pro
-20             -15                 -10                 -5

Gly Ser Thr Gly Asp Ile Val Leu Thr Gln Ser Pro Ala Ser Leu Gly
                 1               5                  10

Val Ser Leu Gly Gln Arg Ala Thr Ile Ser Cys Arg Ala Ser Lys Ser
         15                  20                  25

Val Ser Thr Ser Gly Tyr Ser Tyr Met His Trp Tyr Gln Gln Lys Pro
     30                  35                  40
```

```
Gly Gln Thr Pro Lys Leu Leu Ile Tyr Leu Ala Ser Asn Leu Glu Ser
 45                  50                  55                  60

Gly Val Pro Ala Arg Phe Ser Gly Ser Gly Ser Gly Thr Asp Phe Thr
 65                  70                  75

Leu Asn Ile His Pro Val Glu Glu Glu Asp Ala Ala Thr Tyr Tyr Cys
         80                  85                  90

Gln His Ser Arg Glu Asn Pro Tyr Thr Phe Gly Gly Gly Thr Lys Leu
         95                 100                 105

Glu Ile Lys
    110
```

(2) INFORMATION FOR SEQ ID NO: 26:

(i) SEQUENCE CHARACTERISTICS:
        (A) LENGTH: 405 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..405

(ix) FEATURE:
        (A) NAME/KEY: sig_peptide
        (B) LOCATION: 1..57

(ix) FEATURE:
        (A) NAME/KEY: mat_peptide
        (B) LOCATION: 58..405

(xi) SEQUENCE DESCRIPTION: SEQ ID NO: 26:

```
ATG GGA TGG AGC GGG ATC TTT CTC TTC CTT CTG TCA GGA ACT GCA GGT        48
Met Gly Trp Ser Gly Ile Phe Leu Phe Leu Leu Ser Gly Thr Ala Gly
-19             -15                 -10                  -5

GTC CAC TCT GAG ATC CAG CTG CAG CAG TCT GGA CCT GAG CTG ATG AAG        96
Val His Ser Glu Ile Gln Leu Gln Gln Ser Gly Pro Glu Leu Met Lys
              1              5                  10

CCT GGG GCT TCA GTG AAG ATA TCC TGC AAG GCT TCT GGT TAC TCA TTC       144
Pro Gly Ala Ser Val Lys Ile Ser Cys Lys Ala Ser Gly Tyr Ser Phe
 15                  20                  25

ACT AGC TAT TAC ATA CAC TGG GTG AAG CAG AGC CAT GGA AAG AGC CTT       192
Thr Ser Tyr Tyr Ile His Trp Val Lys Gln Ser His Gly Lys Ser Leu
 30                  35                  40                  45

GAG TGG ATT GGA TAT ATT GAT CCT TTC AAT GGT GGT ACT AGC TAC AAC       240
Glu Trp Ile Gly Tyr Ile Asp Pro Phe Asn Gly Gly Thr Ser Tyr Asn
             50                  55                  60

CAG AAA TTC AAG GGC AAG GCC ACA TTG ACT GTT GAC AAA TCT TCC AGC       288
Gln Lys Phe Lys Gly Lys Ala Thr Leu Thr Val Asp Lys Ser Ser Ser
                 65                  70                  75

ACA GCC TAC ATG CAT CTC AGC AGC CTG ACA TCT GAG GAC TCT GCA GTC       336
Thr Ala Tyr Met His Leu Ser Ser Leu Thr Ser Glu Asp Ser Ala Val
             80                  85                  90

TAT TAC TGT GCA AGG GGG GGT AAC CGC TTT GCT TAC TGG GGC CAA GGG       384
Tyr Tyr Cys Ala Arg Gly Gly Asn Arg Phe Ala Tyr Trp Gly Gln Gly
         95                 100                 105

ACT CTG GTC ACT GTC TCT GCA                                           405
Thr Leu Val Thr Val Ser Ala
110             115
```

(2) INFORMATION FOR SEQ ID NO: 27:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 27:

Met Gly Trp Ser Gly Ile Phe Leu Phe Leu Leu Ser Gly Thr Ala Gly
-19             -15                 -10                 -5

Val His Ser Glu Ile Gln Leu Gln Gln Ser Gly Pro Glu Leu Met Lys
            1                   5                   10

Pro Gly Ala Ser Val Lys Ile Ser Cys Lys Ala Ser Gly Tyr Ser Phe
        15                  20                  25

Thr Ser Tyr Tyr Ile His Trp Val Lys Gln Ser His Gly Lys Ser Leu
    30                  35                  40                  45

Glu Trp Ile Gly Tyr Ile Asp Pro Phe Asn Gly Gly Thr Ser Tyr Asn
                50                  55                  60

Gln Lys Phe Lys Gly Lys Ala Thr Leu Thr Val Asp Lys Ser Ser Ser
                65                  70                  75

Thr Ala Tyr Met His Leu Ser Ser Leu Thr Ser Glu Asp Ser Ala Val
            80                  85                  90

Tyr Tyr Cys Ala Arg Gly Gly Asn Arg Phe Ala Tyr Trp Gly Gln Gly
        95                  100                 105

Thr Leu Val Thr Val Ser Ala
110                 115

(2) INFORMATION FOR SEQ ID NO: 28:

(i) SEQUENCE CHARACTERISTICS:
        (A) LENGTH: 381 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..381

(ix) FEATURE:
        (A) NAME/KEY: sig_peptide
        (B) LOCATION: 1..60

(ix) FEATURE:
        (A) NAME/KEY: mat_peptide
        (B) LOCATION: 61..381

(xi) SEQUENCE DESCRIPTION: SEQ ID NO: 28:

ATG GTG TCC TCA GCT CAG TTC CTT GGT CTC CTG TTG CTC TGT TTT CAA        48
Met Val Ser Ser Ala Gln Phe Leu Gly Leu Leu Leu Leu Cys Phe Gln
-20                 -15                 -10                 -5

GGT ACC AGA TGT GAT ATC CAG ATG ACA CAG ACT ACA TCC TCC CTG TCT        96
Gly Thr Arg Cys Asp Ile Gln Met Thr Gln Thr Thr Ser Ser Leu Ser
            1                   5                   10

GCC TCT CTG GGA GAC AGA GTC ACC ATC AGT TGC AGG GCA AGT CAG GAC       144
Ala Ser Leu Gly Asp Arg Val Thr Ile Ser Cys Arg Ala Ser Gln Asp
        15                  20                  25

ATT AGC AGT TAT TTA AAC TGG TAT CAG CAG AAA CCA GAT GGA ACT ATT       192
Ile Ser Ser Tyr Leu Asn Trp Tyr Gln Gln Lys Pro Asp Gly Thr Ile
    30                  35                  40

AAA CTC CTG ATC TAC TAC ACA TCA AGA TTA CAC TCA GGA GTC CCA TCA       240

```
Lys Leu Leu Ile Tyr Tyr Thr Ser Arg Leu His Ser Gly Val Pro Ser
 45                  50                  55                  60

AGG TTC AGT GGC AGT GGG TCT GGA ACA GAT TAT TCT CTC ACC ATT AAC      288
Arg Phe Ser Gly Ser Gly Ser Gly Thr Asp Tyr Ser Leu Thr Ile Asn
                     65                  70                  75

AAC CTG GAG CAA GAA GAC ATT GCC ACT TAC TTT TGC CAA CAG GGT AAC      336
Asn Leu Glu Gln Glu Asp Ile Ala Thr Tyr Phe Cys Gln Gln Gly Asn
             80                  85                  90

ACG CTT CCG TAC ACG TTC GGA GGG GGG ACC AAG CTG GAA ATA AAT          381
Thr Leu Pro Tyr Thr Phe Gly Gly Gly Thr Lys Leu Glu Ile Asn
         95                 100                 105

(2) INFORMATION FOR SEQ ID NO: 29:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 29:

Met Val Ser Ser Ala Gln Phe Leu Gly Leu Leu Leu Cys Phe Gln
-20                 -15                 -10                  -5

Gly Thr Arg Cys Asp Ile Gln Met Thr Gln Thr Thr Ser Ser Leu Ser
                  1                   5                  10

Ala Ser Leu Gly Asp Arg Val Thr Ile Ser Cys Arg Ala Ser Gln Asp
             15                  20                  25

Ile Ser Ser Tyr Leu Asn Trp Tyr Gln Gln Lys Pro Asp Gly Thr Ile
         30                  35                  40

Lys Leu Leu Ile Tyr Tyr Thr Ser Arg Leu His Ser Gly Val Pro Ser
 45                  50                  55                  60

Arg Phe Ser Gly Ser Gly Ser Gly Thr Asp Tyr Ser Leu Thr Ile Asn
                     65                  70                  75

Asn Leu Glu Gln Glu Asp Ile Ala Thr Tyr Phe Cys Gln Gln Gly Asn
             80                  85                  90

Thr Leu Pro Tyr Thr Phe Gly Gly Gly Thr Lys Leu Glu Ile Asn
         95                 100                 105

(2) INFORMATION FOR SEQ ID NO: 30:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..411

(ix) FEATURE:
        (A) NAME/KEY: sig_peptide
        (B) LOCATION: 1..54

(ix) FEATURE:
        (A) NAME/KEY: mat_peptide
        (B) LOCATION: 55..411

(xi) SEQUENCE DESCRIPTION: SEQ ID NO: 30:

ATG AGA GTG CTG ATT CTT TTG TGG CTG TTC ACA GCC TTT CCT GGT ATC       48
Met Arg Val Leu Ile Leu Leu Trp Leu Phe Thr Ala Phe Pro Gly Ile
-18                 -15                 -10                  -5
```

```
CTG TCT GAT GTG CAG CTT CAG GAG TCG GGA CCT GTC CTG GTG AAG CCT      96
Leu Ser Asp Val Gln Leu Gln Glu Ser Gly Pro Val Leu Val Lys Pro
  1               5                  10

TCT CAG TCT CTG TCC CTC ACC TGC ACT GTC ACT GGC TAC TCA ATC ACC     144
Ser Gln Ser Leu Ser Leu Thr Cys Thr Val Thr Gly Tyr Ser Ile Thr
 15                  20                  25                  30

AGT GAT CAT GCC TGG AGC TGG ATC CGG CAG TTT CCA GGA AAC AAA CTG     192
Ser Asp His Ala Trp Ser Trp Ile Arg Gln Phe Pro Gly Asn Lys Leu
                 35                  40                  45

GAG TGG ATG GGC TAC ATA AGT TAC AGT GGT ATC ACT ACC TAC AAC CCA     240
Glu Trp Met Gly Tyr Ile Ser Tyr Ser Gly Ile Thr Thr Tyr Asn Pro
             50                  55                  60

TCT CTC AAA AGT CGA ATC TCT ATC ACT CGA GAC ACA TCC AAG AAC CAG     288
Ser Leu Lys Ser Arg Ile Ser Ile Thr Arg Asp Thr Ser Lys Asn Gln
 65                  70                  75

TTC TTC CTA CAG TTG AAT TCT GTG ACT ACT GGG GAC ACG TCC ACA TAT     336
Phe Phe Leu Gln Leu Asn Ser Val Thr Thr Gly Asp Thr Ser Thr Tyr
         80                  85                  90

TAC TGT GCA AGA TCC CTA GCT CGG ACT ACG GCT ATG GAC TAC TGG GGT     384
Tyr Cys Ala Arg Ser Leu Ala Arg Thr Thr Ala Met Asp Tyr Trp Gly
 95             100                 105                 110

CAA GGA ACC TCA GTC ACC GTC TCC TCA                                 411
Gln Gly Thr Ser Val Thr Val Ser Ser
                115

(2) INFORMATION FOR SEQ ID NO: 31:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO: 31:

Met Arg Val Leu Ile Leu Leu Trp Leu Phe Thr Ala Phe Pro Gly Ile
-18             -15                 -10                  -5

Leu Ser Asp Val Gln Leu Gln Glu Ser Gly Pro Val Leu Val Lys Pro
  1               5                  10

Ser Gln Ser Leu Ser Leu Thr Cys Thr Val Thr Gly Tyr Ser Ile Thr
 15                  20                  25                  30

Ser Asp His Ala Trp Ser Trp Ile Arg Gln Phe Pro Gly Asn Lys Leu
                 35                  40                  45

Glu Trp Met Gly Tyr Ile Ser Tyr Ser Gly Ile Thr Thr Tyr Asn Pro
             50                  55                  60

Ser Leu Lys Ser Arg Ile Ser Ile Thr Arg Asp Thr Ser Lys Asn Gln
 65                  70                  75

Phe Phe Leu Gln Leu Asn Ser Val Thr Thr Gly Asp Thr Ser Thr Tyr
         80                  85                  90

Tyr Cys Ala Arg Ser Leu Ala Arg Thr Thr Ala Met Asp Tyr Trp Gly
 95             100                 105                 110

Gln Gly Thr Ser Val Thr Val Ser Ser
                115

(2) INFORMATION FOR SEQ ID NO: 32:

(i) SEQUENCE CHARACTERISTICS:
        (A) LENGTH: 393 base pairs
        (B) TYPE: nucleic acid
        (C) STRANDEDNESS: double
```

(D) TOPOLOGY: linear (ii) MOLECULE TYPE: DNA (genomic)

(ix) FEATURE:
    (A) NAME/KEY: CDS
    (B) LOCATION: 1..393

(ix) FEATURE:
    (A) NAME/KEY: sig_peptide
    (B) LOCATION: 1..60

(ix) FEATURE:
    (A) NAME/KEY: mat_peptide
    (B) LOCATION: 61..393

(xi) SEQUENCE DESCRIPTION: SEQ ID NO: 32:

```
ATG GAG TCA GAC ACA CTC CTG CTA TGG GTG CTG CTG CTC TGG GTT CCA        48
Met Glu Ser Asp Thr Leu Leu Leu Trp Val Leu Leu Leu Trp Val Pro
-20             -15                 -10                 -5

GGT TCC ACA GGT GAC ATT GTG TTG ATC CAA TCT CCA GCT TCT TTG GCT        96
Gly Ser Thr Gly Asp Ile Val Leu Ile Gln Ser Pro Ala Ser Leu Ala
                 1               5                  10

GTG TCT CTA GGG CAG AGG GCC ACC ATA TCC TGC AGA GCC AGT GAA AGT       144
Val Ser Leu Gly Gln Arg Ala Thr Ile Ser Cys Arg Ala Ser Glu Ser
            15                  20                  25

GTT GAT AGT TAT GGC AAT AGT TTT ATG CAC TGG TAC CAG CAG AAA CCA       192
Val Asp Ser Tyr Gly Asn Ser Phe Met His Trp Tyr Gln Gln Lys Pro
        30                  35                  40

GGA CAG CCA CCC AAA CTC CTC ATC TAT CGT GCA TCC AAC CTA GAA TCT       240
Gly Gln Pro Pro Lys Leu Leu Ile Tyr Arg Ala Ser Asn Leu Glu Ser
45                  50                  55                  60

GGG ATC CCT GCC AGG TTC AGT GGC AGT GGG TCT AGG ACA GAC TTC ACC       288
Gly Ile Pro Ala Arg Phe Ser Gly Ser Gly Ser Arg Thr Asp Phe Thr
                65                  70                  75

CTC ACC ATT AAT CCT GTG GAG GCT GAT GAT GTT GCA ACC TAT TAC TGT       336
Leu Thr Ile Asn Pro Val Glu Ala Asp Asp Val Ala Thr Tyr Tyr Cys
            80                  85                  90

CAG CAA AGT AAT GAG GAT CCT CCC ACG TTC GGT GCT GGG ACC AAG CTG       384
Gln Gln Ser Asn Glu Asp Pro Pro Thr Phe Gly Ala Gly Thr Lys Leu
        95                  100                 105

GAG CTG AAA                                                            393
Glu Leu Lys
    110
```

(2) INFORMATION FOR SEQ ID NO: 33:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 33:

```
Met Glu Ser Asp Thr Leu Leu Leu Trp Val Leu Leu Leu Trp Val Pro
-20             -15                 -10                 -5

Gly Ser Thr Gly Asp Ile Val Leu Ile Gln Ser Pro Ala Ser Leu Ala
                 1               5                  10

Val Ser Leu Gly Gln Arg Ala Thr Ile Ser Cys Arg Ala Ser Glu Ser
            15                  20                  25

Val Asp Ser Tyr Gly Asn Ser Phe Met His Trp Tyr Gln Gln Lys Pro
        30                  35                  40

Gly Gln Pro Pro Lys Leu Leu Ile Tyr Arg Ala Ser Asn Leu Glu Ser
```

```
                45                  50                  55                  60
Gly Ile Pro Ala Arg Phe Ser Gly Ser Gly Ser Arg Thr Asp Phe Thr
                        65                  70                  75

Leu Thr Ile Asn Pro Val Glu Ala Asp Asp Val Ala Thr Tyr Tyr Cys
                80                  85                  90

Gln Gln Ser Asn Glu Asp Pro Pro Thr Phe Gly Ala Gly Thr Lys Leu
            95                 100                 105

Glu Leu Lys
        110

(2) INFORMATION FOR SEQ ID NO: 34:

(i) SEQUENCE CHARACTERISTICS:
        (A) LENGTH: 417 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..417

(ix) FEATURE:
        (A) NAME/KEY: sig_peptide
        (B) LOCATION: 1..57

(ix) FEATURE:
        (A) NAME/KEY: mat_peptide
        (B) LOCATION: 58..417

(xi) SEQUENCE DESCRIPTION: SEQ ID NO: 34:

ATG GGA TGG AGC GGG GTC TTT ATC TTC CTC CTG TCA GTA ACT GCA GGT        48
Met Gly Trp Ser Gly Val Phe Ile Phe Leu Leu Ser Val Thr Ala Gly
-19             -15                 -10                 -5

GTC CAC TCC CAG GTT CAA TTG CAG CAG TCT GGA GCT GAG TTG ATG AAG        96
Val His Ser Gln Val Gln Leu Gln Gln Ser Gly Ala Glu Leu Met Lys
                1                   5                  10

CCT GGG GCC TCA GTC AAG ATC TCC TGC AAG GCT ACT GGC TAC ACA TTC       144
Pro Gly Ala Ser Val Lys Ile Ser Cys Lys Ala Thr Gly Tyr Thr Phe
        15                  20                  25

AGT AGT TAT TGG ATA GTG TGG ATA AAG CAG AGG CCT GGA CAT GGC CTT       192
Ser Ser Tyr Trp Ile Val Trp Ile Lys Gln Arg Pro Gly His Gly Leu
 30                  35                  40                  45

GAG TGG ATT GGA GAG ATT TTA CCT GGA ACC GGT AGT ACT AAC TAC AAT       240
Glu Trp Ile Gly Glu Ile Leu Pro Gly Thr Gly Ser Thr Asn Tyr Asn
                 50                  55                  60

GAG AAA TTC AAG GGC AAG GCC ACA TTC ACT GCA GAT ACA TCT TCC AAC       288
Glu Lys Phe Lys Gly Lys Ala Thr Phe Thr Ala Asp Thr Ser Ser Asn
            65                  70                  75

ACA GCC TAC ATG CAA CTC AGC AGC CTG ACA TCT GAG GAC TCT GCC GTC       336
Thr Ala Tyr Met Gln Leu Ser Ser Leu Thr Ser Glu Asp Ser Ala Val
        80                  85                  90

TAT TAC TGT GCA AGT CTA GAC AGC TCG GGC TAC TAT GCT ATG GAC TAT       384
Tyr Tyr Cys Ala Ser Leu Asp Ser Ser Gly Tyr Tyr Ala Met Asp Tyr
    95                 100                 105

TGG GGT CAA GGA ACC TCA GTC ACC GTC TCC TCA                           417
Trp Gly Gln Gly Thr Ser Val Thr Val Ser Ser
110                 115                 120

(2) INFORMATION FOR SEQ ID NO: 35:

(i) SEQUENCE CHARACTERISTICS:
```

(A) LENGTH: 139 amino acids
(B) TYPE: amino acid
(D) TOPOLOGY: linear (ii) MOLECULE TYPE: protein (xi) SEQUENCE DESCRIPTION: SEQ ID NO: 35:

```
Met Gly Trp Ser Gly Val Phe Ile Phe Leu Leu Ser Val Thr Ala Gly
-19             -15             -10                  -5

Val His Ser Gln Val Gln Leu Gln Gln Ser Gly Ala Glu Leu Met Lys
         1               5                  10

Pro Gly Ala Ser Val Lys Ile Ser Cys Lys Ala Thr Gly Tyr Thr Phe
     15              20                  25

Ser Ser Tyr Trp Ile Val Trp Ile Lys Gln Arg Pro Gly His Gly Leu
 30              35                  40                      45

Glu Trp Ile Gly Glu Ile Leu Pro Gly Thr Gly Ser Thr Asn Tyr Asn
                 50                  55                  60

Glu Lys Phe Lys Gly Lys Ala Thr Phe Thr Ala Asp Thr Ser Ser Asn
             65                  70                  75

Thr Ala Tyr Met Gln Leu Ser Ser Leu Thr Ser Glu Asp Ser Ala Val
         80                  85                  90

Tyr Tyr Cys Ala Ser Leu Asp Ser Ser Gly Tyr Tyr Ala Met Asp Tyr
     95                 100                 105

Trp Gly Gln Gly Thr Ser Val Thr Val Ser Ser
110             115                 120
```

(2) INFORMATION FOR SEQ ID NO: 36:

(i) SEQUENCE CHARACTERISTICS:
(A) LENGTH: 381 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..381

(ix) FEATURE:
(A) NAME/KEY: sig_peptide
(B) LOCATION: 1..60

(ix) FEATURE:
(A) NAME/KEY: mat_peptide
(B) LOCATION: 61..381

(xi) SEQUENCE DESCRIPTION: SEQ ID NO: 36:

```
ATG GTG TCC ACA CCT CAG TTC CTT GGT CTC CTG TTG ATC TGT TTT CAA      48
Met Val Ser Thr Pro Gln Phe Leu Gly Leu Leu Leu Ile Cys Phe Gln
-20             -15             -10                  -5

GGT ACC AGA TGT GAT ATC CAG ATG ACA CAG ACT ACA TCC TCC CTG TCT      96
Gly Thr Arg Cys Asp Ile Gln Met Thr Gln Thr Thr Ser Ser Leu Ser
                 1               5                  10

GCC TCT CTG GGA GAC AGA GTC ACC ATC AGT TGC AGG GCA AGT CAG GAC     144
Ala Ser Leu Gly Asp Arg Val Thr Ile Ser Cys Arg Ala Ser Gln Asp
             15                  20                  25

ATT AGT AAT TAT TTA AAC TGG TAT CAA CAG AAA CCA GAT GGA ACT GTT     192
Ile Ser Asn Tyr Leu Asn Trp Tyr Gln Gln Lys Pro Asp Gly Thr Val
         30                  35                  40

AAA CTC CTG ATC TAC TAT ACA TCA AGA TTA CAC TCA GGA GTC CCA TCA     240
Lys Leu Leu Ile Tyr Tyr Thr Ser Arg Leu His Ser Gly Val Pro Ser
     45                  50                  55                  60
```

```
AGG TTC AGT GGC AGT GGG TCT GGA ACA GAT TAT TCT CTC ACC ATT AGC        288
Arg Phe Ser Gly Ser Gly Ser Gly Thr Asp Tyr Ser Leu Thr Ile Ser
                 65                  70                  75

AAC CTG GAG CAA GAA GAT ATT GCC AGT TAC TTT TGC CAA CAG GGT TAT        336
Asn Leu Glu Gln Glu Asp Ile Ala Ser Tyr Phe Cys Gln Gln Gly Tyr
                 80                  85                  90

ACG CCT CCG TGG ACG TTC GGT GGA GGC ACC AAG TTG GAA ATC AAA            381
Thr Pro Pro Trp Thr Phe Gly Gly Gly Thr Lys Leu Glu Ile Lys
                 95                 100                 105
```

(2) INFORMATION FOR SEQ ID NO: 37:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 37:

```
Met Val Ser Thr Pro Gln Phe Leu Gly Leu Leu Leu Ile Cys Phe Gln
-20                 -15                 -10                  -5

Gly Thr Arg Cys Asp Ile Gln Met Thr Gln Thr Thr Ser Ser Leu Ser
                  1                   5                  10

Ala Ser Leu Gly Asp Arg Val Thr Ile Ser Cys Arg Ala Ser Gln Asp
                 15                  20                  25

Ile Ser Asn Tyr Leu Asn Trp Tyr Gln Gln Lys Pro Asp Gly Thr Val
                 30                  35                  40

Lys Leu Leu Ile Tyr Tyr Thr Ser Arg Leu His Ser Gly Val Pro Ser
 45                  50                  55                  60

Arg Phe Ser Gly Ser Gly Ser Gly Thr Asp Tyr Ser Leu Thr Ile Ser
                 65                  70                  75

Asn Leu Glu Gln Glu Asp Ile Ala Ser Tyr Phe Cys Gln Gln Gly Tyr
                 80                  85                  90

Thr Pro Pro Trp Thr Phe Gly Gly Gly Thr Lys Leu Glu Ile Lys
                 95                 100                 105
```

(2) INFORMATION FOR SEQ ID NO: 38:

(i) SEQUENCE CHARACTERISTICS:
        (A) LENGTH: 402 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..402

(ix) FEATURE:
        (A) NAME/KEY: sig_peptide
        (B) LOCATION: 1..51

(ix) FEATURE:
        (A) NAME/KEY: mat_peptide
        (B) LOCATION: 52..402

(xi) SEQUENCE DESCRIPTION: SEQ ID NO: 38:

```
ATG GAG CTG GAT CTT TAT CTT ATT CTG TCA GTA ACT TCA GGT GTC TAC         48
Met Glu Leu Asp Leu Tyr Leu Ile Leu Ser Val Thr Ser Gly Val Tyr
-17         -15                 -10                  -5

TCA CAG GTT CAG CTC CAG CAG TCT GGG GCT GAG CTG GCA AGA CCT GGG         96
```

```
Ser Gln Val Gln Leu Gln Gln Ser Gly Ala Glu Leu Ala Arg Pro Gly
  1               5                  10                  15

GCT TCA GTG AAG TTG TCC TGC AAG GCT TCT GGC TAC ACC TTT ACT AAC     144
Ala Ser Val Lys Leu Ser Cys Lys Ala Ser Gly Tyr Thr Phe Thr Asn
             20                  25                  30

TAC TGG GTG CAG TGG GTA AAA CAG AGG CCT GGA CAG GGT CTG GAA TGG     192
Tyr Trp Val Gln Trp Val Lys Gln Arg Pro Gly Gln Gly Leu Glu Trp
                 35                  40                  45

ATT GGG TCT ATT TAT CCT GGA GAT GGT GAT ACT AGG AAC ACT CAG AAG     240
Ile Gly Ser Ile Tyr Pro Gly Asp Gly Asp Thr Arg Asn Thr Gln Lys
             50                  55                  60

TTC AAG GGC AAG GCC ACA TTG ACT GCA GAT AAA TCC TCC ATC ACA GCC     288
Phe Lys Gly Lys Ala Thr Leu Thr Ala Asp Lys Ser Ser Ile Thr Ala
 65                  70                  75

TAC ATG CAA CTC ACC AGC TTG GCA TCT GAG GAC TCT GCG GTC TAT TAC     336
Tyr Met Gln Leu Thr Ser Leu Ala Ser Glu Asp Ser Ala Val Tyr Tyr
 80                  85                  90                  95

TGT GCA AGA TCG ACT GGT AAC CAC TTT GAC TAC TGG GGC CAA GGC ACC     384
Cys Ala Arg Ser Thr Gly Asn His Phe Asp Tyr Trp Gly Gln Gly Thr
                100                 105                 110

ACT CTC ACA GTC TCC TCA                                             402
Thr Leu Thr Val Ser Ser
            115

(2) INFORMATION FOR SEQ ID NO: 39:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO: 39:

Met Glu Leu Asp Leu Tyr Leu Ile Leu Ser Val Thr Ser Gly Val Tyr
-17         -15                 -10                  -5

Ser Gln Val Gln Leu Gln Gln Ser Gly Ala Glu Leu Ala Arg Pro Gly
  1               5                  10                  15

Ala Ser Val Lys Leu Ser Cys Lys Ala Ser Gly Tyr Thr Phe Thr Asn
             20                  25                  30

Tyr Trp Val Gln Trp Val Lys Gln Arg Pro Gly Gln Gly Leu Glu Trp
                 35                  40                  45

Ile Gly Ser Ile Tyr Pro Gly Asp Gly Asp Thr Arg Asn Thr Gln Lys
             50                  55                  60

Phe Lys Gly Lys Ala Thr Leu Thr Ala Asp Lys Ser Ser Ile Thr Ala
 65                  70                  75

Tyr Met Gln Leu Thr Ser Leu Ala Ser Glu Asp Ser Ala Val Tyr Tyr
 80                  85                  90                  95

Cys Ala Arg Ser Thr Gly Asn His Phe Asp Tyr Trp Gly Gln Gly Thr
                100                 105                 110

Thr Leu Thr Val Ser Ser
            115

(2) INFORMATION FOR SEQ ID NO: 40:

(i) SEQUENCE CHARACTERISTICS:
        (A) LENGTH: 35 base pairs
        (B) TYPE: nucleic acid
        (C) STRANDEDNESS: single
        (D) TOPOLOGY: linear
```

(ii) MOLECULE TYPE: other nucleic acid
            (A) DESCRIPTION: /desc = "Primer"

(xi) SEQUENCE DESCRIPTION: SEQ ID NO: 40:

ACAAAGCTTC CACCATGGAG TCAGACACAC TCCTG                                    35

(2) INFORMATION FOR SEQ ID NO: 41:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 41:

GGCTAAGCTT CCACCATGGG ATGGAGCGGG ATCTTT                                   36

(2) INFORMATION FOR SEQ ID NO: 42:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 42:

CTTGGATCCA CTCACGTTTT ATTTCCAGCT TGGTC                                    35

(2) INFORMATION FOR SEQ ID NO: 43:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 43:

GTTGGATCCA CTCACCTGCA GAGACAGTTA CCAGAG                                   36

(2) INFORMATION FOR SEQ ID NO: 44:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 44:

CTTGGATCCA CTCACGATTT ATTTCCAGCT TGGTC                                    35

(2) INFORMATION FOR SEQ ID NO: 45:

(i) SEQUENCE CHARACTERISTICS:
            (A) LENGTH: 36 base pairs
            (B) TYPE: nucleic acid
            (C) STRANDEDNESS: single
            (D) TOPOLOGY: linear

```
            (ii) MOLECULE TYPE: other nucleic acid
                 (A) DESCRIPTION: /desc = "Primer"

(xi) SEQUENCE DESCRIPTION: SEQ ID NO: 45:

ACAAAGCTTC CACCATGGTG TCCTCAGCTC AGTTCC                                         36

(2) INFORMATION FOR SEQ ID NO: 46:

(i) SEQUENCE CHARACTERISTICS:
                 (A) LENGTH: 39 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "Primer"

(xi) SEQUENCE DESCRIPTION: SEQ ID NO: 46:

TGTTAGATCT ACTCACCTGA GGAGACAGTG ACTGAGGTT                                      39

(2) INFORMATION FOR SEQ ID NO: 47:

(i) SEQUENCE CHARACTERISTICS:
                 (A) LENGTH: 36 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "Primer"

(xi) SEQUENCE DESCRIPTION: SEQ ID NO: 47:

GTCTAAGCTT CCACCATGAG AGTGCTGATT CTTTTG                                         36

(2) INFORMATION FOR SEQ ID NO: 48:

(i) SEQUENCE CHARACTERISTICS:
                 (A) LENGTH: 17 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "Primer"

(xi) SEQUENCE DESCRIPTION: SEQ ID NO: 48:

TACGCAAACC GCCTCTC                                                              17

(2) INFORMATION FOR SEQ ID NO: 49:

(i) SEQUENCE CHARACTERISTICS:
                 (A) LENGTH: 18 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "Primer"

(xi) SEQUENCE DESCRIPTION: SEQ ID NO: 49:

GAGTGCACCA TATGCGGT                                                             18

(2) INFORMATION FOR SEQ ID NO: 50:

(i) SEQUENCE CHARACTERISTICS:
                 (A) LENGTH: 55 base pairs
                 (B) TYPE: nucleic acid
                 (C) STRANDEDNESS: single
```

(D) TOPOLOGY: linear (ii) MOLECULE TYPE: other nucleic acid
            (A) DESCRIPTION: /desc = "Primer"

(xi) SEQUENCE DESCRIPTION: SEQ ID NO: 50:

ACCGTGTCTG GCTACACCTT CACCAGCGAT CATGCCTGGA GCTGGGTGAG ACAGC         55

(2) INFORMATION FOR SEQ ID NO: 51:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 51:

TGAGTGGATT GGATACATTA GTTATAGTGG AATCACAACC TATAATCCAT CTCTCAAATC    60

CAG                                                                  63

(2) INFORMATION FOR SEQ ID NO: 52:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 52:

TATTATTGTG CAAGATCCCT AGCTCGGACT ACGGCTATGG ACTACTGGGG TCAA          54

(2) INFORMATION FOR SEQ ID NO: 53:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 53:

GTGACAATGC TGAGAGACAC CAGCAAG                                        27

(2) INFORMATION FOR SEQ ID NO: 54:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 54:

GGTGTCCACT CCGATGTCCA ACTG                                           24

(2) INFORMATION FOR SEQ ID NO: 55:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 55:

GGTCTTGAGT GGATGGGATA CATTAGT                                          27

(2) INFORMATION FOR SEQ ID NO: 56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 56:

GTGTCTGGCT ACTCAATTAC CAGCATCAT                                        29

(2) INFORMATION FOR SEQ ID NO: 57:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 57:

TGTAGAGCCA GCCAGGACAT CAGCAGTTAC CTGAACTGGT ACCAGCAG                   48

(2) INFORMATION FOR SEQ ID NO: 58:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 58:

ATCTACTACA CCTCCAGACT GCACTCTGGT GTGCCAAGCA GA                         42

(2) INFORMATION FOR SEQ ID NO: 59:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 59:

ACCTACTACT GCCAACAGGG TAACACGCTT CCATACACGT TCGGCCAAGG                 50

(2) INFORMATION FOR SEQ ID NO: 60:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Primer"

(xi) SEQUENCE DESCRIPTION: SEQ ID NO: 60:

AGCGGTACCG ACTACACCTT CACCATC                           27

(2) INFORMATION FOR SEQ ID NO: 61:

(i) SEQUENCE CHARACTERISTICS:
    (A) LENGTH: 706 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: sig_peptide
    (B) LOCATION: 8..52

(ix) FEATURE:
    (A) NAME/KEY: sig_peptide
    (B) LOCATION: 135..146

(ix) FEATURE:
    (A) NAME/KEY: mat_peptide
    (B) LOCATION: 147..503

(ix) FEATURE:
    (A) NAME/KEY: CDS
    (B) LOCATION: join(8..52, 135..146, 147..503)

(xi) SEQUENCE DESCRIPTION: SEQ ID NO: 61:

```
AAGCTTC ATG GGA TGG AGC TGT ATC ATC CTC TTC TTG GTA GCA ACA GCT           49
        Met Gly Trp Ser Cys Ile Ile Leu Phe Leu Val Ala Thr Ala
        -19             -15                 -10

ACA GGTAAGGGGC TCACAGTAGC AGGCTTGAGG TCTGGACATA TATATGGGTG               102
Thr
-5

ACAATGACAT CCACTTTGCC TTTCTCTCCA CA GGT GTC CAC TCC CAG GTC CAA          155
                                    Gly Val His Ser Gln Val Gln
                                    -4              1

CTG CAG GAG AGC GGT CCA GGT CTT GTG AGA CCT AGC CAG ACC CTG AGC          203
Leu Gln Glu Ser Gly Pro Gly Leu Val Arg Pro Ser Gln Thr Leu Ser
    5               10                  15

CTG ACC TGC ACC GTG TCT GGC TAC TCA ATT ACC AGC GAT CAT GCC TGG          251
Leu Thr Cys Thr Val Ser Gly Tyr Ser Ile Thr Ser Asp His Ala Trp
20              25                  30                  35

AGC TGG GTG AGA CAG CCA CCT GGA CGA GGT CTT GAG TGG ATT GGA TAC          299
Ser Trp Val Arg Gln Pro Pro Gly Arg Gly Leu Glu Trp Ile Gly Tyr
            40                  45                  50

ATT AGT TAT AGT GGA ATC ACA ACC TAT AAT CCA TCT CTC AAA TCC AGA          347
Ile Ser Tyr Ser Gly Ile Thr Thr Tyr Asn Pro Ser Leu Lys Ser Arg
                55                  60                  65

GTG ACA ATG CTG AGA GAC ACC AGC AAG AAC CAG TTC AGC CTG AGA CTC          395
Val Thr Met Leu Arg Asp Thr Ser Lys Asn Gln Phe Ser Leu Arg Leu
        70                  75                  80

AGC AGC GTG ACA GCC GCC GAC ACC GCG GTT TAT TAT TGT GCA AGA TCC          443
Ser Ser Val Thr Ala Ala Asp Thr Ala Val Tyr Tyr Cys Ala Arg Ser
85                  90                  95

CTA GCT CGG ACT ACG GCT ATG GAC TAC TGG GGT CAA GGC AGC CTC GTC          491
```

```
Leu Ala Arg Thr Thr Ala Met Asp Tyr Trp Gly Gln Gly Ser Leu Val
100                 105                 110                 115

ACA GTC TCC TCA GGTGAGTCCT TACAACCTCT CTCTTCTATT CAGCTTAAAT         543
Thr Val Ser Ser

AGATTTTACT GCATTTGTTG GGGGGGAAAT GTGTGTATCT GAATTTCAGG TCATGAAGGA   603

CTAGGGACAC CTTGGGAGTC AGAAAGGGTC ATTGGGAGCC CGGGCTGATG CAGACAGACA   663

TCCTCAGCTC CCAGACTTCA TGGCCAGAGA TTTATAGGGA TCC                    706

(2) INFORMATION FOR SEQ ID NO: 62:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO: 62:

Met Gly Trp Ser Cys Ile Ile Leu Phe Leu Val Ala Thr Ala Thr Gly
-19             -15                 -10                  -5

Val His Ser Gln Val Gln Leu Gln Glu Ser Gly Pro Gly Leu Val Arg
             1               5                   10

Pro Ser Gln Thr Leu Ser Leu Thr Cys Thr Val Ser Gly Tyr Ser Ile
         15                  20                  25

Thr Ser Asp His Ala Trp Ser Trp Val Arg Gln Pro Pro Gly Arg Gly
    30                  35                  40                  45

Leu Glu Trp Ile Gly Tyr Ile Ser Tyr Ser Gly Ile Thr Thr Tyr Asn
                50                  55                  60

Pro Ser Leu Lys Ser Arg Val Thr Met Leu Arg Asp Thr Ser Lys Asn
            65                  70                  75

Gln Phe Ser Leu Arg Leu Ser Ser Val Thr Ala Ala Asp Thr Ala Val
        80                  85                  90

Tyr Tyr Cys Ala Arg Ser Leu Ala Arg Thr Thr Ala Met Asp Tyr Trp
    95                  100                 105

Gly Gln Gly Ser Leu Val Thr Val Ser Ser
110                 115

(2) INFORMATION FOR SEQ ID NO: 63:

(i) SEQUENCE CHARACTERISTICS:
        (A) LENGTH: 506 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: sig_peptide
        (B) LOCATION: 8..52

(ix) FEATURE:
        (A) NAME/KEY: sig_peptide
        (B) LOCATION: 135..146

(ix) FEATURE:
        (A) NAME/KEY: mat_peptide
        (B) LOCATION: 147..467

(ix) FEATURE:
        (A) NAME/KEY: CDS
        (B) LOCATION: join(8..52, 135..146, 147..467)

(xi) SEQUENCE DESCRIPTION: SEQ ID NO: 63:
```

```
AAGCTTC ATG GGA TGG AGC TGT ATC ATC CTC TTC TTG GTA GCA ACA GCT         49
        Met Gly Trp Ser Cys Ile Ile Leu Phe Leu Val Ala Thr Ala
        -19             -15                 -10

ACA GGTAAGGGGC TCACAGTAGC AGGCTTGAGG TCTGGACATA TATATGGGTG              102
Thr
 -5

ACAATGACAT CCACTTTGCC TTTCTCTCCA CA GGT GTC CAC TCC GAC ATC CAG         155
                                    Gly Val His Ser Asp Ile Gln
                                    -4                  1

ATG ACC CAG AGC CCA AGC AGC CTG AGC GCC AGC GTG GGT GAC AGA GTG         203
Met Thr Gln Ser Pro Ser Ser Leu Ser Ala Ser Val Gly Asp Arg Val
     5               10                  15

ACC ATC ACC TGT AGA GCC AGC CAG GAC ATC AGC AGT TAC CTG AAT TGG         251
Thr Ile Thr Cys Arg Ala Ser Gln Asp Ile Ser Ser Tyr Leu Asn Trp
 20              25                  30                  35

TAC CAG CAG AAG CCA GGT AAG GCT CCA AAG CTG CTG ATC TAC TAC ACC         299
Tyr Gln Gln Lys Pro Gly Lys Ala Pro Lys Leu Leu Ile Tyr Tyr Thr
             40                  45                  50

TCC AGA CTG CAC TCT GGT GTG CCA AGC AGA TTC AGC GGT AGC GGT AGC         347
Ser Arg Leu His Ser Gly Val Pro Ser Arg Phe Ser Gly Ser Gly Ser
                 55                  60                  65

GGT ACC GAC TTC ACC TTC ACC ATC AGC AGC CTC CAG CCA GAG GAC ATC         395
Gly Thr Asp Phe Thr Phe Thr Ile Ser Ser Leu Gln Pro Glu Asp Ile
             70                  75                  80

GCT ACC TAC TAC TGC CAA CAG GGT AAC ACG CTT CCA TAC ACG TTC GGC         443
Ala Thr Tyr Tyr Cys Gln Gln Gly Asn Thr Leu Pro Tyr Thr Phe Gly
             85                  90                  95

CAA GGG ACC AAG GTG GAA ATC AAA CGTGAGTAGA ATTTAAACTT TGCTTCCTCA        497
Gln Gly Thr Lys Val Glu Ile Lys
100             105

GTTGGATCC                                                               506

(2) INFORMATION FOR SEQ ID NO: 64:

(i) SEQUENCE CHARACTERISTICS:
         (A) LENGTH: 126 amino acids
         (B) TYPE: amino acid
         (D) TOPOLOGY: linear (ii) MOLECULE TYPE: protein (xi) SEQUENCE DESCRIPTION: SEQ ID NO: 64:

Met Gly Trp Ser Cys Ile Ile Leu Phe Leu Val Ala Thr Ala Thr Gly
-19             -15                 -10                 -5

Val His Ser Asp Ile Gln Met Thr Gln Ser Pro Ser Ser Leu Ser Ala
            1                   5                  10

Ser Val Gly Asp Arg Val Thr Ile Thr Cys Arg Ala Ser Gln Asp Ile
        15                  20                  25

Ser Ser Tyr Leu Asn Trp Tyr Gln Gln Lys Pro Gly Lys Ala Pro Lys
    30                  35                  40                  45

Leu Leu Ile Tyr Tyr Thr Ser Arg Leu His Ser Gly Val Pro Ser Arg
                50                  55                  60

Phe Ser Gly Ser Gly Ser Gly Thr Asp Phe Thr Phe Thr Ile Ser Ser
            65                  70                  75

Leu Gln Pro Glu Asp Ile Ala Thr Tyr Tyr Cys Gln Gln Gly Asn Thr
        80                  85                  90

Leu Pro Tyr Thr Phe Gly Gln Gly Thr Lys Val Glu Ile Lys
    95                  100                 105
```

(2) INFORMATION FOR SEQ ID NO: 65:

(i) SEQUENCE CHARACTERISTICS:
        (A) LENGTH: 438 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 12..425

(ix) FEATURE:
        (A) NAME/KEY: sig_peptide
        (B) LOCATION: 12..68

(ix) FEATURE:
        (A) NAME/KEY: mat_peptide
        (B) LOCATION: 69..425

(xi) SEQUENCE DESCRIPTION: SEQ ID NO: 65:

```
AAGCTTCCAC C ATG GGA TGG AGC TGT ATC ATC CTC TTC TTG GTA GCA ACA         50
            Met Gly Trp Ser Cys Ile Ile Leu Phe Leu Val Ala Thr
            -19             -15                 -10

GCT ACA GGT GTC CAC TCC CAG GTC CAA CTG CAG GAG AGC GGT CCA GGT          98
Ala Thr Gly Val His Ser Gln Val Gln Leu Gln Glu Ser Gly Pro Gly
        -5              1               5                   10

CTT GTG AGA CCT AGC CAG ACC CTG AGC CTG ACC TGC ACC GTG TCT GGC         146
Leu Val Arg Pro Ser Gln Thr Leu Ser Leu Thr Cys Thr Val Ser Gly
            15                  20                  25

TAC TCA ATT ACC AGC GAT CAT GCC TGG AGC TGG GTT CGC CAG CCA CCT         194
Tyr Ser Ile Thr Ser Asp His Ala Trp Ser Trp Val Arg Gln Pro Pro
            30                  35                  40

GGA CGA GGT CTT GAG TGG ATT GGA TAC ATT AGT TAT AGT GGA ATC ACA         242
Gly Arg Gly Leu Glu Trp Ile Gly Tyr Ile Ser Tyr Ser Gly Ile Thr
            45                  50                  55

ACC TAT AAT CCA TCT CTC AAA TCC AGA GTG ACA ATG CTG AGA GAC ACC         290
Thr Tyr Asn Pro Ser Leu Lys Ser Arg Val Thr Met Leu Arg Asp Thr
            60                  65                  70

AGC AAG AAC CAG TTC AGC CTG AGA CTC AGC AGC GTG ACA GCC GCC GAC         338
Ser Lys Asn Gln Phe Ser Leu Arg Leu Ser Ser Val Thr Ala Ala Asp
 75                 80                  85                  90

ACC GCG GTT TAT TAT TGT GCA AGA TCC CTA GCT CGG ACT ACG GCT ATG         386
Thr Ala Val Tyr Tyr Cys Ala Arg Ser Leu Ala Arg Thr Thr Ala Met
                95                  100                 105

GAC TAC TGG GGT CAA GGC AGC CTC GTC ACA GTC TCC TCA GGTGAGTGGA         435
Asp Tyr Trp Gly Gln Gly Ser Leu Val Thr Val Ser Ser
            110                 115

TCC                                                                    438
```

(2) INFORMATION FOR SEQ ID NO: 66:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO: 66:

```
Met Gly Trp Ser Cys Ile Ile Leu Phe Leu Val Ala Thr Ala Thr Gly
-19             -15                 -10                 -5

Val His Ser Gln Val Gln Leu Gln Glu Ser Gly Pro Gly Leu Val Arg
```

```
                 1               5                  10
Pro Ser Gln Thr Leu Ser Leu Thr Cys Thr Val Ser Gly Tyr Ser Ile
    15                  20                  25

Thr Ser Asp His Ala Trp Ser Trp Val Arg Gln Pro Pro Gly Arg Gly
30                  35                  40                  45

Leu Glu Trp Ile Gly Tyr Ile Ser Tyr Ser Gly Ile Thr Thr Tyr Asn
                50                  55                  60

Pro Ser Leu Lys Ser Arg Val Thr Met Leu Arg Asp Thr Ser Lys Asn
            65                  70                  75

Gln Phe Ser Leu Arg Leu Ser Ser Val Thr Ala Ala Asp Thr Ala Val
    80                  85                  90

Tyr Tyr Cys Ala Arg Ser Leu Ala Arg Thr Thr Ala Met Asp Tyr Trp
95                  100                 105

Gly Gln Gly Ser Leu Val Thr Val Ser Ser
110             115
```

(2) INFORMATION FOR SEQ ID NO: 67:

(i) SEQUENCE CHARACTERISTICS:
      (A) LENGTH: 402 base pairs
      (B) TYPE: nucleic acid
      (C) STRANDEDNESS: double
      (D) TOPOLOGY: linear (ii) MOLECULE TYPE: DNA (genomic)

(ix) FEATURE:
       (A) NAME/KEY: CDS
       (B) LOCATION: 12..389

(ix) FEATURE:
       (A) NAME/KEY: sig_peptide
       (B) LOCATION: 12..68

(ix) FEATURE:
       (A) NAME/KEY: mat_peptide
       (B) LOCATION: 69..389

(xi) SEQUENCE DESCRIPTION: SEQ ID NO: 67:

```
AAGCTTCCAC C ATG GGA TGG AGC TGT ATC ATC CTC TTC TTG GTA GCA ACA        50
             Met Gly Trp Ser Cys Ile Ile Leu Phe Leu Val Ala Thr
             -19             -15                 -10

GCT ACA GGT GTC CAC TCC GAC ATC CAG ATG ACC CAG AGC CCA AGC AGC         98
Ala Thr Gly Val His Ser Asp Ile Gln Met Thr Gln Ser Pro Ser Ser
    -5              1               5                   10

CTG AGC GCC AGC GTG GGT GAC AGA GTG ACC ATC ACC TGT AGA GCC AGC        146
Leu Ser Ala Ser Val Gly Asp Arg Val Thr Ile Thr Cys Arg Ala Ser
                15                  20                  25

CAG GAC ATC AGC AGT TAC CTG AAT TGG TAC CAG CAG AAG CCA GGA AAG        194
Gln Asp Ile Ser Ser Tyr Leu Asn Trp Tyr Gln Gln Lys Pro Gly Lys
                30                  35                  40

GCT CCA AAG CTG CTG ATC TAC TAC ACC TCC AGA CTG CAC TCT GGT GTG        242
Ala Pro Lys Leu Leu Ile Tyr Tyr Thr Ser Arg Leu His Ser Gly Val
            45                  50                  55

CCA AGC AGA TTC AGC GGT AGC GGT AGC GGT ACC GAC TTC ACC TTC ACC        290
Pro Ser Arg Phe Ser Gly Ser Gly Ser Gly Thr Asp Phe Thr Phe Thr
            60                  65                  70

ATC AGC AGC CTC CAG CCA GAG GAC ATC GCT ACC TAC TAC TGC CAA CAG        338
Ile Ser Ser Leu Gln Pro Glu Asp Ile Ala Thr Tyr Tyr Cys Gln Gln
75                  80                  85                  90

GGT AAC ACG CTT CCA TAC ACG TTC GGC CAA GGG ACC AAG GTG GAA ATC        386
Gly Asn Thr Leu Pro Tyr Thr Phe Gly Gln Gly Thr Lys Val Glu Ile
                95                  100                 105
```

```
AAA CGTGAGTGGA TCC                                                        402
Lys
```

(2) INFORMATION FOR SEQ ID NO: 68:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO: 68:

```
Met Gly Trp Ser Cys Ile Ile Leu Phe Leu Val Ala Thr Ala Thr Gly
-19             -15              -10              -5

Val His Ser Asp Ile Gln Met Thr Gln Ser Pro Ser Ser Leu Ser Ala
         1               5                   10

Ser Val Gly Asp Arg Val Thr Ile Thr Cys Arg Ala Ser Gln Asp Ile
    15              20                  25

Ser Ser Tyr Leu Asn Trp Tyr Gln Gln Lys Pro Gly Lys Ala Pro Lys
30              35                  40                  45

Leu Leu Ile Tyr Tyr Thr Ser Arg Leu His Ser Gly Val Pro Ser Arg
             50                  55                  60

Phe Ser Gly Ser Gly Ser Gly Thr Asp Phe Thr Phe Thr Ile Ser Ser
             65                  70                  75

Leu Gln Pro Glu Asp Ile Ala Thr Tyr Tyr Cys Gln Gln Gly Asn Thr
             80                  85                  90

Leu Pro Tyr Thr Phe Gly Gln Gly Thr Lys Val Glu Ile Lys
             95             100                 105
```

(2) INFORMATION FOR SEQ ID NO: 69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 69:

```
TAAGGATCCA CTCACCTGAG GAGACTGTGA CGAGGC                                    36
```

(2) INFORMATION FOR SEQ ID NO: 70:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 70:

```
ATCAAGCTTC CACCATGGGA TGGAGCTGTA TC                                        32
```

(2) INFORMATION FOR SEQ ID NO: 71:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 71:

AATGGATCCA CTCACGTTTG ATTTCCACCT                                   30

(2) INFORMATION FOR SEQ ID NO: 72:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 72:

CATGCCTGGA GCTGGGTTCG CCAGCCACCT GGA                               33

(2) INFORMATION FOR SEQ ID NO: 73:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 73:

TCCAGGTGGC TGGCGAACCC AGCTCCAGGC ATG                               33

(2) INFORMATION FOR SEQ ID NO: 74:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 74:

CAGCAGAAGC CAGGAAAGGC TCCAAAGCTG                                   30

(2) INFORMATION FOR SEQ ID NO: 75:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 75:

CAGCTTTGGA GCCTTTCCTG GCTTCTGCTG                                   30

(2) INFORMATION FOR SEQ ID NO: 76:

(i) SEQUENCE CHARACTERISTICS:
            (A) LENGTH: 66 base pairs
            (B) TYPE: nucleic acid (C) STRANDEDNESS: single
            (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 76:

ACCTGTAGAG CCAGCAAGAG TGTTAGTACA TCTGGCTATA GTTATATGCA CTGGTACCAG        60

CAGAAG        66

(2) INFORMATION FOR SEQ ID NO: 77:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 77:

GCTGGCTCTA CAGGT        15

(2) INFORMATION FOR SEQ ID NO: 78:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 78:

AAGCTGCTGA TCTACCTTCC ATCCACCCTG GAATCTGGTG TGCCAAGC        48

(2) INFORMATION FOR SEQ ID NO: 79:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 79:

GTAGATCAGC AGCTT        15

(2) INFORMATION FOR SEQ ID NO: 80:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 80:

GCTACCTACT ACTGCCAGCA CAGTAGGGAG ACCCCATACA CGTTCGGC        48

(2) INFORMATION FOR SEQ ID NO: 81:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 81:

```
CTGGCAGTAG GTAGC                                                      15
```

(2) INFORMATION FOR SEQ ID NO: 82:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 12..401

(ix) FEATURE:
        (A) NAME/KEY: sig_peptide
        (B) LOCATION: 12..68

(ix) FEATURE:
        (A) NAME/KEY: mat_peptide
        (B) LOCATION: 69..401

(xi) SEQUENCE DESCRIPTION: SEQ ID NO: 82:

```
AAGCTTCCAC C ATG GGA TGG AGC TGT ATC ATC CTC TTC TTG GTA GCA ACA        50
             Met Gly Trp Ser Cys Ile Ile Leu Phe Leu Val Ala Thr
             -19             -15                 -10

GCT ACA GGT GTC CAC TCC GAC ATC CAG ATG ACC CAG AGC CCA AGC AGC         98
Ala Thr Gly Val His Ser Asp Ile Gln Met Thr Gln Ser Pro Ser Ser
 -5               1               5                  10

CTG AGC GCC AGC GTG GGT GAC AGA GTG ACC ATC ACC TGT AGA GCC AGC        146
Leu Ser Ala Ser Val Gly Asp Arg Val Thr Ile Thr Cys Arg Ala Ser
             15                  20                  25

AAG AGT GTT AGT ACA TCT GGC TAT AGT TAT ATG CAC TGG TAC CAG CAG        194
Lys Ser Val Ser Thr Ser Gly Tyr Ser Tyr Met His Trp Tyr Gln Gln
             30                  35                  40

AAG CCA GGA AAG GCT CCA AAG CTG CTG ATC TAC CTT GCA TCC AAC CTG        242
Lys Pro Gly Lys Ala Pro Lys Leu Leu Ile Tyr Leu Ala Ser Asn Leu
             45                  50                  55

GAA TCT GGT GTG CCA AGC AGA TTC AGC GGT AGC GGT AGC GGT ACC GAC        290
Glu Ser Gly Val Pro Ser Arg Phe Ser Gly Ser Gly Ser Gly Thr Asp
 60              65                  70

TTC ACC TTC ACC ATC AGC AGC CTC CAG CCA GAG GAC ATC GCT ACC TAC        338
Phe Thr Phe Thr Ile Ser Ser Leu Gln Pro Glu Asp Ile Ala Thr Tyr
 75              80                  85                  90

TAC TGC CAG CAC AGT AGG GAG AAC CCA TAC ACG TTC GGC CAA GGG ACC        386
Tyr Cys Gln His Ser Arg Glu Asn Pro Tyr Thr Phe Gly Gln Gly Thr
                 95                 100                 105

AAG GTG GAA ATC AAA CGTGAGTGGA TCC                                     414
Lys Val Glu Ile Lys
            110
```

(2) INFORMATION FOR SEQ ID NO: 83:

(i) SEQUENCE CHARACTERISTICS:
        (A) LENGTH: 130 amino acids (B) TYPE: amino acid
        (D) TOPOLOGY: linear (ii) MOLECULE TYPE: protein (xi) SEQUENCE DESCRIPTION: SEQ ID NO: 83:

Met Gly Trp Ser Cys Ile Ile Leu Phe Leu Val Ala Thr Ala Thr Gly
-19             -15             -10                  -5

Val His Ser Asp Ile Gln Met Thr Gln Ser Pro Ser Ser Leu Ser Ala
                1               5                  10

Ser Val Gly Asp Arg Val Thr Ile Thr Cys Arg Ala Ser Lys Ser Val
        15                  20                  25

Ser Thr Ser Gly Tyr Ser Tyr Met His Trp Tyr Gln Gln Lys Pro Gly
    30              35              40                  45

Lys Ala Pro Lys Leu Leu Ile Tyr Leu Ala Ser Asn Leu Glu Ser Gly
                50              55              60

Val Pro Ser Arg Phe Ser Gly Ser Gly Ser Gly Thr Asp Phe Thr Phe
            65              70              75

Thr Ile Ser Ser Leu Gln Pro Glu Asp Ile Ala Thr Tyr Tyr Cys Gln
        80              85              90

His Ser Arg Glu Asn Pro Tyr Thr Phe Gly Gln Gly Thr Lys Val Glu
    95              100             105

Ile Lys
110

(2) INFORMATION FOR SEQ ID NO: 84:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 84:

GGTTATTCAT TCACTAGTTA TTACATACAC TGGGTTAGAC AGGCC         45

(2) INFORMATION FOR SEQ ID NO: 85:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 85:

AGTGAATGAA TAACCGCTAG CTTTACA         27

(2) INFORMATION FOR SEQ ID NO: 86:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 86:

-continued

```
GAGTGGGTGG GCTATATTGA TCCTTTCAAT GGTGGTACTA GCTATAATCA GAAGTTCAAG      60

GGCAGGGTT                                                              69
```

(2) INFORMATION FOR SEQ ID NO: 87:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 87:

```
ATAGCCCACC CACTC                                                       15
```

(2) INFORMATION FOR SEQ ID NO: 88:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 88:

```
GGGGGTAACC GCTTTGCTTA CTGGGGACAG GGTACC                                36
```

(2) INFORMATION FOR SEQ ID NO: 89:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 89:

```
AGCAAAGCGG TTACCCCCTC TGGCGCAGTA GTAGAC                                36
```

(2) INFORMATION FOR SEQ ID NO: 90:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 90:

```
CAAGGTTACC ATGACCGTGG ACACCTCTAC                                       30
```

(2) INFORMATION FOR SEQ ID NO: 91:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid -continued (A) DESCRIPTION: /desc = "Primer"

(xi) SEQUENCE DESCRIPTION: SEQ ID NO: 91:

CACGGTCATG GTAACCTTGC CCTTGAACTT                                            30

(2) INFORMATION FOR SEQ ID NO: 92:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 92:

GGGCTCGAAT GGATTGGCTA TATTGATCCT                                            30

(2) INFORMATION FOR SEQ ID NO: 93:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 93:

AGGATCAATA TAGCCAATCC ATTCGAGCCC                                            30

(2) INFORMATION FOR SEQ ID NO: 94:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 94:

GTAAAACGAG GCCAGT                                                           16

(2) INFORMATION FOR SEQ ID NO: 95:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 95:

AACAGCTATG ACCATGA                                                          17

(2) INFORMATION FOR SEQ ID NO: 96:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: DNA (genomic)

(ix) FEATURE:
             (A) NAME/KEY: CDS
             (B) LOCATION: 16..420

(ix) FEATURE:
             (A) NAME/KEY: sig_peptide
             (B) LOCATION: 16..72

(ix) FEATURE:
             (A) NAME/KEY: mat_peptide
             (B) LOCATION: 73..420

(xi) SEQUENCE DESCRIPTION: SEQ ID NO: 96:

```
AAGCTTGCCG CCACC ATG GAC TGG ACC TGG CGC GTG TTT TGC CTG CTC GCC          51
                 Met Asp Trp Thr Trp Arg Val Phe Cys Leu Leu Ala
                 -19             -15                 -10

GTG GCT CCT GGG GCC CAC AGC CAG GTG CAA CTA GTG CAG TCC GGC GCC           99
Val Ala Pro Gly Ala His Ser Gln Val Gln Leu Val Gln Ser Gly Ala
        -5              1               5

GAA GTG AAG AAA CCC GGT GCT TCC GTG AAA GTC AGC TGT AAA GCT AGC          147
Glu Val Lys Lys Pro Gly Ala Ser Val Lys Val Ser Cys Lys Ala Ser
10              15                  20                  25

GGT TAT TCA TTC ACT AGT TAT TAC ATA CAC TGG GTT AGA CAG GCC CCA          195
Gly Tyr Ser Phe Thr Ser Tyr Tyr Ile His Trp Val Arg Gln Ala Pro
                30                  35                  40

GGC CAA GGG CTC GAG TGG GTG GGC TAT ATT GAT CCT TTC AAT GGT GGT          243
Gly Gln Gly Leu Glu Trp Val Gly Tyr Ile Asp Pro Phe Asn Gly Gly
            45                  50                  55

ACT AGC TAT AAT CAG AAG TTC AAG GGC AAG GTT ACC ATG ACC GTG GAC          291
Thr Ser Tyr Asn Gln Lys Phe Lys Gly Lys Val Thr Met Thr Val Asp
        60                  65                  70

ACC TCT ACA AAC ACC GCC TAC ATG GAA CTG TCC AGC CTG CGC TCC GAG          339
Thr Ser Thr Asn Thr Ala Tyr Met Glu Leu Ser Ser Leu Arg Ser Glu
    75                  80                  85

GAC ACT GCA TGC TAC TAC TGC GCC AGA GGG GGT AAC CGC TTT GCT TAC          387
Asp Thr Ala Cys Tyr Tyr Cys Ala Arg Gly Gly Asn Arg Phe Ala Tyr
90                  95                  100                 105

TGG GGA CAG GGT ACC CTT GTC ACC GTC AGT TCA GGTGAGTGGA TCC               433
Trp Gly Gln Gly Thr Leu Val Thr Val Ser Ser
                110                 115
```

(2) INFORMATION FOR SEQ ID NO: 97:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 97:

```
Met Asp Trp Thr Trp Arg Val Phe Cys Leu Leu Ala Val Ala Pro Gly
-19             -15                 -10                 -5

Ala His Ser Gln Val Gln Leu Val Gln Ser Gly Ala Glu Val Lys Lys
                1               5                   10

Pro Gly Ala Ser Val Lys Val Ser Cys Lys Ala Ser Gly Tyr Ser Phe
        15                  20                  25

Thr Ser Tyr Tyr Ile His Trp Val Arg Gln Ala Pro Gly Gln Gly Leu
    30                  35                  40                  45

Glu Trp Val Gly Tyr Ile Asp Pro Phe Asn Gly Gly Thr Ser Tyr Asn
                50                  55                  60
```

```
Gln Lys Phe Lys Gly Lys Val Thr Met Thr Val Asp Thr Ser Thr Asn
            65                  70                  75

Thr Ala Tyr Met Glu Leu Ser Ser Leu Arg Ser Glu Asp Thr Ala Cys
        80                  85                  90

Tyr Tyr Cys Ala Arg Gly Gly Asn Arg Phe Ala Tyr Trp Gly Gln Gly
    95                 100                 105

Thr Leu Val Thr Val Ser Ser
110             115
```

(2) INFORMATION FOR SEQ ID NO: 98:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 16..420

(ix) FEATURE:
        (A) NAME/KEY: sig_peptide
        (B) LOCATION: 16..72

(ix) FEATURE:
        (A) NAME/KEY: mat_peptide
        (B) LOCATION: 73..420

(xi) SEQUENCE DESCRIPTION: SEQ ID NO: 98:

```
AAGCTTGCCG CCACC ATG GAC TGG ACC TGG CGC GTG TTT TGC CTG CTC GCC       51
                 Met Asp Trp Thr Trp Arg Val Phe Cys Leu Leu Ala
                 -19             -15                 -10

GTG GCT CCT GGG GCC CAC AGC CAG GTG CAA CTA GTG CAG TCC GGC GCC        99
Val Ala Pro Gly Ala His Ser Gln Val Gln Leu Val Gln Ser Gly Ala
        -5              1               5

GAA GTG AAG AAA CCC GGT GCT TCC GTG AAA GTC AGC TGT AAA GCT AGC       147
Glu Val Lys Lys Pro Gly Ala Ser Val Lys Val Ser Cys Lys Ala Ser
 10              15                  20                  25

GGT TAT TCA TTC ACT AGT TAT TAC ATA CAC TGG GTT AGA CAG GCC CCA       195
Gly Tyr Ser Phe Thr Ser Tyr Tyr Ile His Trp Val Arg Gln Ala Pro
                30                  35                  40

GGC CAA GGG CTC GAA TGG ATT GGC TAT ATT GAT CCT TTC AAT GGT GGT       243
Gly Gln Gly Leu Glu Trp Ile Gly Tyr Ile Asp Pro Phe Asn Gly Gly
        45                  50                  55

ACT AGC TAT AAT CAG AAG TTC AAG GGC AAG GTT ACC ATG ACC GTG GAC       291
Thr Ser Tyr Asn Gln Lys Phe Lys Gly Lys Val Thr Met Thr Val Asp
 60                  65                  70

ACC TCT ACA AAC ACC GCC TAC ATG GAA CTG TCC AGC CTG CGC TCC GAG       339
Thr Ser Thr Asn Thr Ala Tyr Met Glu Leu Ser Ser Leu Arg Ser Glu
        75                  80                  85

GAC ACT GCA GTC TAC TAC TGC GCC AGA GGG GGT AAC CGC TTT GCT TAC       387
Asp Thr Ala Val Tyr Tyr Cys Ala Arg Gly Gly Asn Arg Phe Ala Tyr
 90                  95                 100                 105

TGG GGA CAG GGT ACC CTT GTC ACC GTC AGT TCA GGTGAGTGGA TCC            433
Trp Gly Gln Gly Thr Leu Val Thr Val Ser Ser
                110             115
```

(2) INFORMATION FOR SEQ ID NO: 99:

(i) SEQUENCE CHARACTERISTICS:
        (A) LENGTH: 135 amino acids
        (B) TYPE: amino acid (D) TOPOLOGY: linear (ii) MOLECULE TYPE: protein (xi) SEQUENCE DESCRIPTION: SEQ ID NO: 99:

Met Asp Trp Thr Trp Arg Val Phe Cys Leu Leu Ala Val Ala Pro Gly
-19             -15             -10                     -5

Ala His Ser Gln Val Gln Leu Val Gln Ser Gly Ala Glu Val Lys Lys
         1               5                  10

Pro Gly Ala Ser Val Lys Val Ser Cys Lys Ala Ser Gly Tyr Ser Phe
         15              20              25

Thr Ser Tyr Tyr Ile His Trp Val Arg Gln Ala Pro Gly Gln Gly Leu
30              35              40                       45

Glu Trp Ile Gly Tyr Ile Asp Pro Phe Asn Gly Gly Thr Ser Tyr Asn
             50              55              60

Gln Lys Phe Lys Gly Lys Val Thr Met Thr Val Asp Thr Ser Thr Asn
             65              70              75

Thr Ala Tyr Met Glu Leu Ser Ser Leu Arg Ser Glu Asp Thr Ala Val
         80              85              90

Tyr Tyr Cys Ala Arg Gly Gly Asn Arg Phe Ala Tyr Trp Gly Gln Gly
         95              100             105

Thr Leu Val Thr Val Ser Ser
110             115

(2) INFORMATION FOR SEQ ID NO: 100:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 100:

GATAAGCTTG CCGCCACCAT GGACTGGACC TGGAGGGTCT TCTTCTTGCT GGCTGTAGCT      60

CCAGGTGCTC ACTCCCAGGT GCAGCTTGTG                                      90

(2) INFORMATION FOR SEQ ID NO: 101:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 101:

CACTCCCAGG TGCAGCTTGT GCAGTCTGGA GCTGAGGTGA AGAAGCCTGG GGCCTCAGTG      60

AAGGTTTCCT GCAAGGCTTC TGGATACTCA                                      90

(2) INFORMATION FOR SEQ ID NO: 102:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "Primer"

(xi) SEQUENCE DESCRIPTION: SEQ ID NO: 102:

TGCAAGGCTT CTGGATACTC ATTCACTAGT TATTACATAC ACTGGGTGCG CCAGGCCCCC    60

GGACAAAGGC TTGAGTGGAT GGGATATATT                                   90

(2) INFORMATION FOR SEQ ID NO: 103:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 103:

CTTGAGTGGA TGGGATATAT TGACCCTTTC AATGGTGGTA CTAGCTATAA TCAGAAGTTC    60

AAGGGCAGAG TCACCATTAC CGTAGACACA                                   90

(2) INFORMATION FOR SEQ ID NO: 104:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 104:

GTCACCATTA CCGTAGACAC ATCCGCGAGC ACAGCCTACA TGGAGCTGAG CAGCCTGAGA    60

TCTGAAGACA CGGCTGTGTA TTACTGTGCG                                   90

(2) INFORMATION FOR SEQ ID NO: 105:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 105:

ACGGCTGTGT ATTACTGTGC GAGAGGGGGT AACCGCTTTG CTTACTGGGG CCAGGGAACC    60

CTGGTCACCG TCTCCTCAGG TGAGTGGATC CGAC                              94

(2) INFORMATION FOR SEQ ID NO: 106:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 106:

GATAAGCTTG CCGCC                                                   15

(2) INFORMATION FOR SEQ ID NO: 107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 107:

```
GTCGGATCCA CTCAC                                                      15
```

(2) INFORMATION FOR SEQ ID NO: 108:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 16..420

(ix) FEATURE:
        (A) NAME/KEY: sig_peptide
        (B) LOCATION: 16..72

(ix) FEATURE:
        (A) NAME/KEY: mat_peptide
        (B) LOCATION: 73..420

(xi) SEQUENCE DESCRIPTION: SEQ ID NO: 108:

```
AAGCTTGCCG CCACC ATG GAC TGG ACC TGG AGG GTC TTC TTC TTG CTG GCT      51
                Met Asp Trp Thr Trp Arg Val Phe Phe Leu Leu Ala
                -19            -15                 -10

GTA GCT CCA GGT GCT CAC TCC CAG GTG CAG CTT GTG CAG TCT GGA GCT       99
Val Ala Pro Gly Ala His Ser Gln Val Gln Leu Val Gln Ser Gly Ala
         -5               1               5

GAG GTG AAG AAG CCT GGG GCC TCA GTG AAG GTT TCC TGC AAG GCT TCT      147
Glu Val Lys Lys Pro Gly Ala Ser Val Lys Val Ser Cys Lys Ala Ser
 10              15                  20                  25

GGA TAC TCA TTC ACT AGT TAT TAC ATA CAC TGG GTG CGC CAG GCC CCC      195
Gly Tyr Ser Phe Thr Ser Tyr Tyr Ile His Trp Val Arg Gln Ala Pro
             30                  35                  40

GGA CAA AGG CTT GAG TGG ATG GGA TAT ATT GAC CCT TTC AAT GGT GGT      243
Gly Gln Arg Leu Glu Trp Met Gly Tyr Ile Asp Pro Phe Asn Gly Gly
         45                  50                  55

ACT AGC TAT AAT CAG AAG TTC AAG GGC AGA GTC ACC ATT ACC GTA GAC      291
Thr Ser Tyr Asn Gln Lys Phe Lys Gly Arg Val Thr Ile Thr Val Asp
     60                  65                  70

ACA TCC GCG AGC ACA GCC TAC ATG GAG CTG AGC AGT CTG AGA TCT GAA      339
Thr Ser Ala Ser Thr Ala Tyr Met Glu Leu Ser Ser Leu Arg Ser Glu
 75                  80                  85

GAC ACG GCT GTG TAT TAC TGT GCG AGA GGG GGT AAC CGC TTT GCT TAC      387
Asp Thr Ala Val Tyr Tyr Cys Ala Arg Gly Gly Asn Arg Phe Ala Tyr
 90                  95                 100                 105

TGG GGC CAG GGA ACC CTG GTC ACC GTC TCC TCA GGTGAGTGGA TCC           433
Trp Gly Gln Gly Thr Leu Val Thr Val Ser Ser
                 110                 115
```

(2) INFORMATION FOR SEQ ID NO: 109:

(i) SEQUENCE CHARACTERISTICS:
    (A) LENGTH: 135 amino acids
    (B) TYPE: amino acid
    (D) TOPOLOGY: linear (ii) MOLECULE TYPE: protein (xi) SEQUENCE DESCRIPTION: SEQ ID NO: 109:

```
Met Asp Trp Thr Trp Arg Val Phe Phe Leu Leu Ala Val Ala Pro Gly
-19             -15             -10                     -5

Ala His Ser Gln Val Gln Leu Val Gln Ser Gly Ala Glu Val Lys Lys
             1               5                  10

Pro Gly Ala Ser Val Lys Val Ser Cys Lys Ala Ser Gly Tyr Ser Phe
        15                  20                  25

Thr Ser Tyr Tyr Ile His Trp Val Arg Gln Ala Pro Gly Gln Arg Leu
 30              35                  40                      45

Glu Trp Met Gly Tyr Ile Asp Pro Phe Asn Gly Gly Thr Ser Tyr Asn
                 50                  55                  60

Gln Lys Phe Lys Gly Arg Val Thr Ile Thr Val Asp Thr Ser Ala Ser
             65                  70                  75

Thr Ala Tyr Met Glu Leu Ser Ser Leu Arg Ser Glu Asp Thr Ala Val
             80                  85                  90

Tyr Tyr Cys Ala Arg Gly Gly Asn Arg Phe Ala Tyr Trp Gly Gln Gly
             95                 100                 105

Thr Leu Val Thr Val Ser Ser
110             115
```

(2) INFORMATION FOR SEQ ID NO: 110:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 110:

AGGCTTGAGT GGATTGGATA TATTGAC                                27

(2) INFORMATION FOR SEQ ID NO: 111:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 111:

AAGTTCAAGG GCAAGGTCAC CATTACC                                27

(2) INFORMATION FOR SEQ ID NO: 112:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 112:

GGTGCTTCCG TGAAAGTCAG CTGTAAAGCT                                              30

(2) INFORMATION FOR SEQ ID NO: 113:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 113:

AGCTTTACAG CTGACTTTCA CGGAAGCACC                                              30

(2) INFORMATION FOR SEQ ID NO: 114:

(i) SEQUENCE CHARACTERISTICS:
        (A) LENGTH: 80 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 114:

```
Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
             20                  25                  30

Pro Lys Leu Leu Ile Tyr Gly Val Pro Ser Arg Phe Ser Gly Ser Gly
         35                  40                  45

Ser Gly Thr Asp Phe Thr Phe Thr Ile Ser Ser Leu Gln Pro Glu Asp
     50                  55                  60

Ile Ala Thr Tyr Tyr Cys Phe Gly Gln Gly Thr Lys Val Glu Ile Lys
65                  70                  75                  80
```

(2) INFORMATION FOR SEQ ID NO: 115:

(i) SEQUENCE CHARACTERISTICS:
        (A) LENGTH: 107 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 115:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                 85                  90                  95
```

```
Thr Phe Gly Gln Gly Thr Lys Val Glu Ile Lys
            100                 105
```

(2) INFORMATION FOR SEQ ID NO: 116:

(i) SEQUENCE CHARACTERISTICS:
        (A) LENGTH: 87 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 116:

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Trp Val
            20                  25                  30

Arg Gln Pro Pro Gly Arg Gly Leu Glu Trp Ile Gly Arg Val Thr Met
        35                  40                  45

Leu Val Asp Thr Ser Lys Asn Gln Phe Ser Leu Arg Leu Ser Ser Val
    50                  55                  60

Thr Ala Ala Asp Thr Ala Val Tyr Tyr Cys Ala Arg Trp Gly Gln Gly
65                  70                  75                  80

Ser Leu Val Thr Val Ser Ser
            85
```

(2) INFORMATION FOR SEQ ID NO: 117:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 117:

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
        100                 105                 110

Ser Leu Val Thr Val Ser Ser
        115
```

(2) INFORMATION FOR SEQ ID NO: 118:

(i) SEQUENCE CHARACTERISTICS:
        (A) LENGTH: 119 amino acids
        (B) TYPE: amino acid
        (C) STRANDEDNESS: <Unknown>

(D) TOPOLOGY: linear (ii) MOLECULE TYPE: peptide (xi) SEQUENCE DESCRIPTION: SEQ ID NO: 118:

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser
        115

(2) INFORMATION FOR SEQ ID NO: 119:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 119:

Asp Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser
        115

(2) INFORMATION FOR SEQ ID NO: 120:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 120:

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Ser Asp
            20                  25                  30

His Ala Trp Ser Trp Val Arg Gln Pro Pro Gly Arg Gly Leu Glu Trp
            35                  40                  45

Met Gly Tyr Ile Ser Tyr Ser Gly Ile Thr Thr Tyr Asn Pro Ser Leu
            50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

(2) INFORMATION FOR SEQ ID NO: 121:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 121:

Asp Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Ser Asp
            20                  25                  30

His Ala Trp Ser Trp Val Arg Gln Pro Pro Gly Arg Gly Leu Glu Trp
            35                  40                  45

Met Gly Tyr Ile Ser Tyr Ser Gly Ile Thr Thr Tyr Asn Pro Ser Leu
            50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

(2) INFORMATION FOR SEQ ID NO: 122:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 122:

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
```

```
                20                  25                  30
His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
            115

(2) INFORMATION FOR SEQ ID NO: 123:

(i) SEQUENCE CHARACTERISTICS:
        (A) LENGTH: 80 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 123:

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
            35                  40                  45

Ser Gly Thr Asp Phe Thr Phe Thr Ile Ser Ser Leu Gln Pro Glu Asp
            50                  55                  60

Ile Ala Thr Tyr Tyr Cys Phe Gly Gln Gly Thr Lys Val Glu Ile Lys
65                  70                  75                  80

(2) INFORMATION FOR SEQ ID NO: 124:

(i) SEQUENCE CHARACTERISTICS:
        (A) LENGTH: 110 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 124:

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
            35                  40                  45

Lys Leu Leu Ile Tyr Ala Ser Asn Leu Glu Ser Gly Val Pro Ser Arg
            50                  55                  60

Phe Ser Gly Ser Gly Ser Gly Thr Asp Phe Thr Phe Thr Ile Ser Ser
65                  70                  75                  80

Leu Gln Pro Glu Asp Ile Ala Thr Tyr Tyr Cys Gln His Ser Arg Glu
                85                  90                  95
```

Asn Pro Tyr Thr Phe Gly Gln Gly Thr Lys Val Glu Ile Lys
            100                 105                 110

(2) INFORMATION FOR SEQ ID NO: 125:

(i) SEQUENCE CHARACTERISTICS:
        (A) LENGTH: 87 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 125:

Glx Val Gln Leu Val Gln Ser Gly Ala Glu Val Lys Lys Pro Gly Xaa
1               5                   10                  15

Ser Val Xaa Val Ser Cys Lys Ala Ser Gly Tyr Thr Phe Ser Trp Val
            20                  25                  30

Arg Gln Ala Pro Gly Xaa Gly Leu Glu Trp Val Gly Arg Val Thr Xaa
        35                  40                  45

Thr Xaa Asp Xaa Ser Xaa Asn Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

(2) INFORMATION FOR SEQ ID NO: 126:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 126:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Val
        35                  40                  45

Gly Tyr Ile Asp Pro Phe Asn Gly Gly Thr Ser Tyr Asn Gln Lys Phe
    50                  55                  60

Lys Gly Arg Val Thr Met Thr Leu Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
            115

(2) INFORMATION FOR SEQ ID NO: 127:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 127:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Gly Leu Glu Trp Val
            35                  40                  45

Gly Tyr Ile Asp Pro Phe Asn Gly Gly Thr Ser Tyr Asn Gln Lys Phe
50                      55                  60

Lys Gly Lys Val Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
            115

(2) INFORMATION FOR SEQ ID NO: 128:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 128:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Gly Leu Glu Trp Ile
            35                  40                  45

Gly Tyr Ile Asp Pro Phe Asn Gly Gly Thr Ser Tyr Asn Gln Lys Phe
50                      55                  60

Lys Gly Arg Val Thr Met Thr Leu Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
            115

(2) INFORMATION FOR SEQ ID NO: 129:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 129:

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Tyr Ile Asp Pro Phe Asn Gly Gly Thr Ser Tyr Asn Gln Lys Phe
    50                  55                  60

Lys Gly Lys Val Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
        115

(2) INFORMATION FOR SEQ ID NO: 130:

(i) SEQUENCE CHARACTERISTICS:
        (A) LENGTH: 87 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 130:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Arg Leu Glu Trp Met Gly Arg Val Thr Ile
        35                  40                  45

Thr Arg Asp Thr Ser Ala Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

(2) INFORMATION FOR SEQ ID NO: 131:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 131:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Arg Leu Glu Trp Met
        35                  40                  45

Gly Tyr Ile Asp Pro Phe Asn Gly Gly Thr Ser Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
        115

(2) INFORMATION FOR SEQ ID NO: 132:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 132:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Arg Leu Glu Trp Ile
        35                  40                  45

Gly Tyr Ile Asp Pro Phe Asn Gly Gly Thr Ser Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
        115

(2) INFORMATION FOR SEQ ID NO: 133:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 133:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Arg Leu Glu Trp Met
        35                  40                  45

Gly Tyr Ile Asp Pro Phe Asn Gly Gly Thr Ser Tyr Asn Gln Lys Phe
    50                  55                  60

Lys Gly Lys Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys

```
                        85                  90                  95
Ala Arg Gly Gly Asn Arg Phe Ala Tyr Trp Gly Gln Gly Thr Leu Val
            100                 105                 110

Thr Val Ser Ser
        115

(2) INFORMATION FOR SEQ ID NO: 134:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 134:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Arg Leu Glu Trp Ile
            35                  40                  45

Gly Tyr Ile Asp Pro Phe Asn Gly Gly Thr Ser Tyr Asn Gln Lys Phe
    50                  55                  60

Lys Gly Lys Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
        115
```